(12) United States Patent
Farcet et al.

(10) Patent No.: US 12,258,540 B2
(45) Date of Patent: Mar. 25, 2025

(54) ENVIRONMENTALLY COMPATIBLE DETERGENTS FOR INACTIVATION OF LIPID-ENVELOPED VIRUSES

(71) Applicant: TAKEDA PHARMACEUTICAL COMPANY LIMITED, Osaka (JP)

(72) Inventors: Jean-Baptiste Farcet, Vienna (AT); Johanna Kindermann, Maria Enzersdorf (AT); Björn Tille, Tulln (AT); Thomas R. Kreil, Klosterneuburg (AT)

(73) Assignee: TAKEDA PHARMACEUTICAL COMPANY LIMITED, Osaka (JP)

(*) Notice: Subject to any disclaimer, the term of this patent is extended or adjusted under 35 U.S.C. 154(b) by 1327 days.

(21) Appl. No.: 16/760,608

(22) PCT Filed: Oct. 30, 2018

(86) PCT No.: PCT/EP2018/079721
§ 371 (c)(1),
(2) Date: Apr. 30, 2020

(87) PCT Pub. No.: WO2019/086463
PCT Pub. Date: May 9, 2019

(65) Prior Publication Data
US 2021/0032567 A1    Feb. 4, 2021

Related U.S. Application Data

(60) Provisional application No. 62/687,023, filed on Jun. 19, 2018, provisional application No. 62/578,648, filed on Oct. 30, 2017.

(51) Int. Cl.
| | | |
|---|---|---|
| C11D 3/43 | (2006.01) | |
| C07K 14/765 | (2006.01) | |
| C07K 16/06 | (2006.01) | |
| C08G 59/14 | (2006.01) | |
| C11D 1/72 | (2006.01) | |
| C11D 3/36 | (2006.01) | |
| C12N 7/00 | (2006.01) | |

(52) U.S. Cl.
CPC .......... C11D 1/721 (2013.01); C07K 14/765 (2013.01); C07K 16/065 (2013.01); C08G 59/1444 (2013.01); C11D 3/362 (2013.01); C11D 3/43 (2013.01); C12N 7/00 (2013.01); *C12N 2710/16763* (2013.01); *C12N 2740/16063* (2013.01); *C12N 2770/24363* (2013.01)

(58) Field of Classification Search
None
See application file for complete search history.

(56) References Cited

U.S. PATENT DOCUMENTS

| | | |
|---|---|---|
| 1,970,578 A | 8/1934 | Schoeller et al. |
| 4,020,183 A | 4/1977 | Asculai et al. |
| 4,113,712 A | 9/1978 | Funakoshi |
| 4,118,478 A | 10/1978 | Prince et al. |
| 4,206,014 A | 6/1980 | Reichert et al. |
| 4,271,035 A | 6/1981 | Saito et al. |
| 4,356,169 A | 10/1982 | Simons et al. |
| 4,374,127 A | 2/1983 | Larson et al. |
| 4,452,734 A | 6/1984 | Larson et al. |
| 4,471,054 A | 9/1984 | Lattore et al. |
| 4,511,556 A | 4/1985 | Purcell et al. |
| 4,522,809 A | 6/1985 | Adamowicz et al. |
| 4,613,501 A | 9/1986 | Horowitz |
| 4,649,160 A | 3/1987 | Machin |
| 4,661,349 A | 4/1987 | Kino et al. |
| 4,673,733 A | 6/1987 | Chandra et al. |
| 4,975,217 A | 12/1990 | Brown-Skrobot et al. |
| 5,166,057 A | 11/1992 | Palese et al. |
| 5,614,405 A | 5/1997 | Eibl et al. |
| 5,639,730 A | 6/1997 | Eibl et al. |
| 5,648,472 A | 7/1997 | Gehringer et al. |
| 5,690,937 A | 11/1997 | Parkin et al. |
| 5,712,086 A | 1/1998 | Horowitz et al. |
| 5,733,885 A | 3/1998 | Eibl et al. |
| 5,770,199 A | 6/1998 | Eibl et al. |
| 5,883,256 A | 3/1999 | Schuler et al. |
| 5,952,009 A | 9/1999 | Neurath et al. |
| 5,981,163 A | 11/1999 | Horowitz et al. |
| 5,985,275 A | 11/1999 | Neurath et al. |
| 6,048,537 A | 4/2000 | Violay et al. |

(Continued)

FOREIGN PATENT DOCUMENTS

| | | |
|---|---|---|
| AU | 636907 B2 | 7/1991 |
| AU | 649728 B2 | 4/1992 |

(Continued)

OTHER PUBLICATIONS

Lu Ying et al., "Synthesis and physiochemical properties of ethoxylated lauryl benzyl alcohol", China Surfactant Detergent & Cosmetics, vol. 42, No. 2, Apr. 2012, pp. 79-83.

(Continued)

*Primary Examiner* — Sudhakar Katakam
*Assistant Examiner* — Jennifer C Sawyer
(74) *Attorney, Agent, or Firm* — TROUTMAN PEPPER LOCKE LLP

(57) ABSTRACT

The present invention relates to methods for inactivating a lipid-enveloped virus using environmentally compatible detergents, and to methods for preparing a biopharmaceutical drug using environmentally compatible detergents. The invention also provides environmentally compatible detergents.

32 Claims, 14 Drawing Sheets

(56) References Cited

U.S. PATENT DOCUMENTS

| | | |
|---|---|---|
| 6,136,321 A | 10/2000 | Barrett et al. |
| 6,162,904 A | 12/2000 | Mamidi et al. |
| 6,251,644 B1 | 6/2001 | Sowemimo-Coker et al. |
| 6,251,678 B1 | 6/2001 | Volkin et al. |
| 6,296,847 B1 | 10/2001 | Gokcen et al. |
| 6,403,098 B1 | 6/2002 | Burke et al. |
| 6,462,180 B1 | 10/2002 | Lebing et al. |
| 6,517,849 B1 | 2/2003 | Seger et al. |
| 6,616,931 B1 | 9/2003 | Burke et al. |
| 7,273,567 B1 | 9/2007 | Wellinghoff et al. |
| 7,326,555 B2 | 2/2008 | Konz, Jr. et al. |
| 7,351,415 B2 | 4/2008 | Evans et al. |
| 7,488,695 B2 | 2/2009 | Shanklin |
| 8,124,106 B2 | 2/2012 | Weggeman et al. |
| 8,263,542 B2 | 9/2012 | Futterer et al. |
| 8,603,541 B2 | 12/2013 | Weissman et al. |
| 9,534,037 B2 | 1/2017 | Roy et al. |
| 2001/0021385 A1 | 9/2001 | Volkin et al. |
| 2002/0012671 A1 | 1/2002 | Hildreth et al. |
| 2002/0018792 A1 | 2/2002 | Harichian et al. |
| 2002/0045667 A1 | 4/2002 | Baker, Jr. et al. |
| 2002/0068267 A1 | 6/2002 | Horowitz et al. |
| 2002/0068355 A1 | 6/2002 | Stadler et al. |
| 2002/0168764 A1 | 11/2002 | Coffey et al. |
| 2002/0177215 A1 | 11/2002 | Zhang et al. |
| 2003/0073651 A1 | 4/2003 | Marcelletti et al. |
| 2003/0204077 A1 | 10/2003 | Simms |
| 2003/0232018 A1 | 12/2003 | Lehmberg et al. |
| 2004/0028698 A1 | 2/2004 | Colau et al. |
| 2004/0043041 A1 | 3/2004 | Baker, Jr. et al. |
| 2004/0106184 A1 | 6/2004 | Senesac |
| 2004/0142450 A1 | 7/2004 | Seo et al. |
| 2004/0163671 A1* | 8/2004 | Fournel .................... C11D 1/72 134/40 |
| 2005/0054846 A1 | 3/2005 | Webster et al. |
| 2005/0165221 A1 | 7/2005 | Booth et al. |
| 2006/0166345 A1 | 1/2006 | Harris et al. |
| 2006/0110407 A1 | 5/2006 | Stopera et al. |
| 2006/0240511 A1 | 10/2006 | Eskling et al. |
| 2006/0275781 A1 | 12/2006 | Pham et al. |
| 2007/0128693 A1 | 6/2007 | Wong et al. |
| 2008/0003575 A1 | 1/2008 | Michalik et al. |
| 2008/0090222 A1 | 4/2008 | Ueda et al. |
| 2008/0159957 A1 | 7/2008 | Kavanaugh et al. |
| 2008/0181914 A1 | 7/2008 | Eichhorn |
| 2008/0248047 A1 | 10/2008 | Das et al. |
| 2009/0081193 A1 | 3/2009 | Sasisekharan et al. |
| 2010/0004195 A1 | 1/2010 | Sasisekharan et al. |
| 2010/0061990 A1 | 3/2010 | Sasisekharan et al. |
| 2010/0120085 A1 | 5/2010 | Hyman et al. |
| 2010/0124763 A1 | 5/2010 | Walsh et al. |
| 2010/0129857 A1 | 5/2010 | Walsh et al. |
| 2010/0129858 A1 | 5/2010 | Walsh et al. |
| 2010/0135987 A1 | 6/2010 | Hickman et al. |
| 2010/0136609 A1 | 6/2010 | Clay et al. |
| 2010/0137437 A1 | 6/2010 | Pelet et al. |
| 2011/0009520 A1 | 1/2011 | Figuly et al. |
| 2011/0038890 A1 | 2/2011 | Raviv et al. |
| 2011/0150929 A1 | 6/2011 | Akeefe et al. |
| 2011/0217330 A1 | 9/2011 | Andre et al. |
| 2012/0135454 A1 | 5/2012 | Walsh et al. |
| 2012/0148622 A1 | 6/2012 | tenOever |
| 2012/0219636 A1 | 8/2012 | Li et al. |
| 2012/0225487 A1 | 9/2012 | Weber et al. |
| 2012/0316323 A1 | 12/2012 | Nardini et al. |
| 2013/0071322 A1 | 3/2013 | Figuly |
| 2013/0224266 A1 | 8/2013 | Blais et al. |
| 2014/0073033 A1 | 3/2014 | Sene et al. |
| 2014/0248320 A1 | 9/2014 | Tsai |
| 2014/0274973 A1 | 9/2014 | Pedersen et al. |
| 2014/0309403 A1 | 10/2014 | Brown et al. |
| 2014/0335504 A1 | 11/2014 | Sasisekharan et al. |
| 2015/0065458 A1 | 3/2015 | Pelet et al. |
| 2015/0094240 A1 | 4/2015 | Kilaas et al. |
| 2015/0147329 A1 | 5/2015 | Raman et al. |
| 2015/0203529 A1 | 7/2015 | Godawat et al. |
| 2015/0284447 A1 | 10/2015 | Wan et al. |
| 2015/0301036 A1 | 10/2015 | Lee |
| 2016/0019341 A1 | 1/2016 | Harris et al. |
| 2016/0038585 A1 | 2/2016 | Dormitzer et al. |
| 2016/0045590 A1 | 2/2016 | Milner et al. |
| 2016/0075624 A1 | 3/2016 | Yang et al. |
| 2016/0075742 A1 | 3/2016 | Sasisekharan et al. |
| 2016/0130306 A1 | 5/2016 | Tharakaraman et al. |
| 2016/0186094 A1 | 6/2016 | Johns |
| 2016/0304586 A1 | 10/2016 | Pagany et al. |
| 2016/0324959 A1 | 11/2016 | Schlegl et al. |
| 2016/0333046 A1 | 11/2016 | Fisher et al. |
| 2016/0348144 A1 | 12/2016 | Wong et al. |
| 2017/0095549 A1 | 4/2017 | Suphaphiphat et al. |
| 2017/0114103 A9 | 4/2017 | Garcia-Sastre et al. |

FOREIGN PATENT DOCUMENTS

| | | |
|---|---|---|
| AU | 687153 B2 | 2/1998 |
| AU | 2004249133 B2 | 5/2009 |
| CA | 1 177 395 A | 11/1984 |
| CA | 2228031 A1 | 2/1997 |
| CA | 2 386 014 C | 4/2001 |
| CA | 2 628 379 A1 | 5/2007 |
| CA | 2 628 397 A1 | 5/2007 |
| CA | 2 907 149 A1 | 5/2007 |
| CA | 2 769 673 A1 | 2/2011 |
| CA | 2 800 272 A1 | 12/2011 |
| CA | 2 852 610 A1 | 4/2013 |
| CA | 2 897 752 A1 | 7/2014 |
| CA | 2 898 961 A1 | 7/2014 |
| CA | 2 899 731 A1 | 9/2014 |
| CA | 2 914 604 A1 | 12/2014 |
| CA | 2 603 180 A | 10/2015 |
| CN | 1208091 C | 6/2005 |
| CN | 1230526 C | 12/2005 |
| CN | 101448486 | 6/2009 |
| CN | 101553502 A | 10/2009 |
| CN | 101679912 | 4/2010 |
| CN | 101732711 A | 6/2010 |
| CN | 102464974 A | 5/2012 |
| CN | 102614508 A | 8/2012 |
| CN | 102943000 A | 2/2013 |
| CN | 104211943 A | 12/2014 |
| CN | 104324370 A | 2/2015 |
| CN | 104548084 A | 4/2015 |
| CN | 106117264 A | 11/2016 |
| CN | 106187713 A | 12/2016 |
| CN | 106187714 A | 12/2016 |
| CN | 106187828 A | 12/2016 |
| CN | 106187833 A | 12/2016 |
| CN | 109400449 | 6/2022 |
| DE | 2154996 A1 | 5/1973 |
| DE | 2554428 A1 | 6/1976 |
| DE | 2610717 A1 | 5/1977 |
| DE | 2615161 A1 | 10/1977 |
| DE | 3026044 A1 | 2/1981 |
| DE | 3005495 A1 | 8/1981 |
| EP | 0 001 365 A | 4/1979 |
| EP | 0 005 864 A1 | 12/1979 |
| EP | 0 011 168 A1 | 5/1980 |
| EP | 0 037 931 A2 | 10/1981 |
| EP | 0 041 233 A1 | 12/1981 |
| EP | 0 050 061 A2 | 4/1982 |
| EP | 0 097 003 A2 | 12/1983 |
| EP | 0 099 445 A2 | 2/1984 |
| EP | 0 131 740 A2 | 1/1985 |
| EP | 0 197 554 A2 | 10/1986 |
| EP | 0 203 909 A1 | 12/1986 |
| EP | 0 204 680 A2 | 12/1986 |
| EP | 0 239 859 A2 | 10/1987 |
| EP | 0 278 487 A2 | 8/1988 |
| EP | 0 352 835 A1 | 1/1990 |
| EP | 0 378 208 A2 | 7/1990 |
| EP | 0 415 794 A1 | 3/1991 |
| EP | 0 456 724 A1 | 11/1991 |
| EP | 0 491 125 A1 | 6/1992 |
| EP | 0 519 901 A2 | 12/1992 |

(56) References Cited

FOREIGN PATENT DOCUMENTS

| | | |
|---|---|---|
| EP | 0 522 291 A1 | 1/1993 |
| EP | 0 525 502 A1 | 2/1993 |
| EP | 0 533 492 A2 | 3/1993 |
| EP | 0 572 194 A1 | 12/1993 |
| EP | 0 583 142 A2 | 2/1994 |
| EP | 0 702 719 A1 | 3/1996 |
| EP | 0 771 567 A1 | 5/1997 |
| EP | 0 776 668 A2 | 6/1997 |
| EP | 0 864 646 A2 | 9/1998 |
| EP | 0 827 413 B1 | 8/1999 |
| EP | 1 016 711 A1 | 7/2000 |
| EP | 1 161 958 A1 | 12/2001 |
| EP | 1 364 944 A1 | 11/2003 |
| EP | 1 661 914 A1 | 5/2006 |
| EP | 0 864 646 B1 | 8/2006 |
| EP | 1 691 198 A1 | 8/2006 |
| EP | 1 780 269 A2 | 5/2007 |
| EP | 1 801 591 A2 | 6/2007 |
| EP | 1 923 071 A1 | 5/2008 |
| EP | 1 975 622 A1 | 10/2008 |
| EP | 1 637 593 B1 | 8/2010 |
| EP | 2 174 137 B1 | 11/2011 |
| EP | 2 389 942 A1 | 11/2011 |
| EP | 2 300 497 B1 | 8/2012 |
| EP | 2 545 937 A1 | 1/2013 |
| EP | 2 578 229 A1 | 4/2013 |
| EP | 2 004 702 B1 | 5/2013 |
| EP | 2 253 644 B1 | 10/2013 |
| EP | 2 650 362 A2 | 10/2013 |
| EP | 2 687 595 A1 | 1/2014 |
| EP | 2 690 110 A1 | 1/2014 |
| EP | 2 249 862 B1 | 7/2014 |
| EP | 2 801 372 A2 | 11/2014 |
| EP | 2 923 711 A1 | 9/2015 |
| EP | 2 929 887 A1 | 10/2015 |
| EP | 2 566 958 B1 | 12/2015 |
| EP | 2 442 827 B1 | 1/2016 |
| EP | 2 448 596 B1 | 1/2016 |
| EP | 3 012 330 A1 | 4/2016 |
| EP | 2 427 576 B1 | 6/2016 |
| EP | 3 040 346 A1 | 7/2016 |
| EP | 2 475 384 B1 | 8/2016 |
| EP | 2 493 501 B1 | 4/2017 |
| FR | 2193357 A5 | 2/1974 |
| FR | 2686221 A1 | 7/1993 |
| FR | 2723740 A1 | 2/1996 |
| FR | 3005265 A3 | 11/2014 |
| GB | 1041554 A | 9/1966 |
| GB | 1444962 A | 8/1978 |
| GB | 1549123 A | 8/1979 |
| GB | 1567547 A | 5/1980 |
| GB | 2052983 A | 2/1981 |
| GB | 2158080 A | 11/1985 |
| IE | 58530 B1 | 10/1993 |
| JP | S5265591 A | 5/1977 |
| JP | S5567672 A | 5/1980 |
| JP | S5795917 A | 6/1982 |
| JP | S6041770 A | 3/1985 |
| JP | H02184842 A | 7/1990 |
| JP | H02272068 A | 11/1990 |
| JP | H03168737 A | 7/1991 |
| JP | 2002085057 A | 3/2002 |
| JP | 3293620 B2 | 6/2002 |
| JP | 3545418 B2 | 7/2004 |
| JP | 2011225578 A | 11/2011 |
| JP | 2016204536 A | 12/2016 |
| KR | 20110091678 A | 8/2011 |
| WO | 87/01128 A | 2/1987 |
| WO | 90/04401 A | 5/1990 |
| WO | 92/08981 A1 | 5/1992 |
| WO | 92/16201 A1 | 10/1992 |
| WO | 93/17723 A1 | 9/1993 |
| WO | 94/13329 A1 | 6/1994 |
| WO | 94/17834 A1 | 8/1994 |
| WO | 94/26287 A1 | 11/1994 |
| WO | 95/02324 A1 | 1/1995 |
| WO | 95/16030 A1 | 6/1995 |
| WO | 95/25574 A1 | 9/1995 |
| WO | 96/04555 A1 | 2/1996 |
| WO | 96/28025 A1 | 9/1996 |
| WO | 96/33725 A1 | 10/1996 |
| WO | 96/35710 A1 | 11/1996 |
| WO | 96/36369 A1 | 11/1996 |
| WO | 97/04815 A1 | 2/1997 |
| WO | 97/46667 A1 | 12/1997 |
| WO | 98/06744 A1 | 2/1998 |
| WO | 99/33486 A1 | 7/1999 |
| WO | 99/34791 A1 | 7/1999 |
| WO | 00/69262 A1 | 11/2000 |
| WO | 00/71142 A1 | 11/2000 |
| WO | 00/74722 A2 | 12/2000 |
| WO | 00/76534 A1 | 12/2000 |
| WO | 00/78141 A1 | 12/2000 |
| WO | 00/78275 A2 | 12/2000 |
| WO | 00/78792 A1 | 12/2000 |
| WO | 01/16321 A1 | 3/2001 |
| WO | 01/28338 A2 | 4/2001 |
| WO | 01/44441 A1 | 6/2001 |
| WO | 01/49296 A1 | 7/2001 |
| WO | 01/53443 A1 | 7/2001 |
| WO | 01/53444 A1 | 7/2001 |
| WO | 01/83794 A2 | 11/2001 |
| WO | 02/00266 A2 | 1/2002 |
| WO | 02/24244 A2 | 3/2002 |
| WO | 02/28426 A1 | 4/2002 |
| WO | 02/48176 A1 | 6/2002 |
| WO | 02/067983 A1 | 9/2002 |
| WO | 02/074336 A2 | 9/2002 |
| WO | 02/092139 A1 | 11/2002 |
| WO | 03/000243 A1 | 1/2003 |
| WO | 03/000381 A1 | 1/2003 |
| WO | 03/020107 A2 | 3/2003 |
| WO | 03/053477 A1 | 7/2003 |
| WO | 03/062461 A1 | 7/2003 |
| WO | 2004/004677 A1 | 1/2004 |
| WO | 2004/007533 A1 | 1/2004 |
| WO | 2004015004 | 2/2004 |
| WO | 2004/030608 A2 | 4/2004 |
| WO | 2004/050904 A1 | 6/2004 |
| WO | 2004/105729 A2 | 12/2004 |
| WO | 2004/113377 A1 | 12/2004 |
| WO | 2005/009462 A2 | 2/2005 |
| WO | 2005/014648 A1 | 2/2005 |
| WO | 2005/016240 A2 | 2/2005 |
| WO | 2005/027872 A2 | 3/2005 |
| WO | 2005/049077 A2 | 6/2005 |
| WO | 2005/054275 A2 | 6/2005 |
| WO | 2005/065708 A2 | 7/2005 |
| WO | 2004/092360 A3 | 8/2005 |
| WO | 2005/070454 A2 | 8/2005 |
| WO | 2005/104745 A2 | 11/2005 |
| WO | 2005/105070 A2 | 11/2005 |
| WO | 2005/107797 A1 | 11/2005 |
| WO | 2006/003926 A1 | 1/2006 |
| WO | 2006/011161 A2 | 2/2006 |
| WO | 2006/050489 A2 | 5/2006 |
| WO | 2006/062835 A2 | 6/2006 |
| WO | 2006/062897 A2 | 6/2006 |
| WO | 2006/082115 A1 | 8/2006 |
| WO | 2007/014244 A2 | 2/2007 |
| WO | 2007/017669 A1 | 2/2007 |
| WO | 2007/022718 A1 | 3/2007 |
| WO | 2007/052055 A1 | 5/2007 |
| WO | 2007/052056 A1 | 5/2007 |
| WO | 2007/052058 A1 | 5/2007 |
| WO | 2007/052060 A1 | 5/2007 |
| WO | 2007/052155 A2 | 5/2007 |
| WO | 2007/052163 A2 | 5/2007 |
| WO | 2007/068907 A2 | 6/2007 |
| WO | 2007/085969 A2 | 8/2007 |
| WO | 2007/110776 A1 | 10/2007 |
| WO | 2007/120705 A2 | 10/2007 |
| WO | 2007/144772 A2 | 12/2007 |
| WO | 2008/009309 A1 | 1/2008 |

(56) References Cited

FOREIGN PATENT DOCUMENTS

| | | |
|---|---|---|
| WO | 2008/032219 A2 | 3/2008 |
| WO | 2008/045860 A2 | 4/2008 |
| WO | 2008/051186 A2 | 5/2008 |
| WO | 2008/068631 A2 | 6/2008 |
| WO | 2008/076371 A2 | 6/2008 |
| WO | 2008/096093 A1 | 8/2008 |
| WO | 2008/096126 A1 | 8/2008 |
| WO | 2008/096136 A1 | 8/2008 |
| WO | 2008/128939 A1 | 10/2008 |
| WO | 2008/137747 A1 | 11/2008 |
| WO | 2008/147982 A1 | 12/2008 |
| WO | 2009/001217 A2 | 12/2008 |
| WO | 2009/029695 A1 | 3/2009 |
| WO | 2009/068992 A1 | 6/2009 |
| WO | 2009/081172 A1 | 7/2009 |
| WO | 2009/087560 A1 | 7/2009 |
| WO | 2009/089121 A2 | 7/2009 |
| WO | 2009/115917 A2 | 9/2009 |
| WO | 2009/131606 A2 | 10/2009 |
| WO | 2009/131995 A1 | 10/2009 |
| WO | 2009/132244 A1 | 10/2009 |
| WO | 2009/150532 A1 | 12/2009 |
| WO | 2009/156430 A1 | 12/2009 |
| WO | 2010/009388 A1 | 1/2010 |
| WO | 2010/036938 A2 | 4/2010 |
| WO | 2010/059232 A1 | 5/2010 |
| WO | 2010/092476 A1 | 8/2010 |
| WO | 2010/092477 A1 | 8/2010 |
| WO | 2010/092479 A2 | 8/2010 |
| WO | 2010/125461 A1 | 11/2010 |
| WO | 2010/128396 A2 | 11/2010 |
| WO | 2010/133964 A1 | 11/2010 |
| WO | 2010/136896 A1 | 12/2010 |
| WO | 2010/138736 A2 | 12/2010 |
| WO | 2010/148111 A1 | 12/2010 |
| WO | 2011/003100 A2 | 1/2011 |
| WO | 2011/011753 A1 | 1/2011 |
| WO | 2011/012726 A2 | 2/2011 |
| WO | 2011/030218 A1 | 3/2011 |
| WO | 2011/031850 A1 | 3/2011 |
| WO | 2011/048560 A1 | 4/2011 |
| WO | 2011/051235 A1 | 5/2011 |
| WO | 2011/072097 A1 | 6/2011 |
| WO | 2011/121020 A1 | 10/2011 |
| WO | 2011/121031 A1 | 10/2011 |
| WO | 2011/138229 A1 | 11/2011 |
| WO | 2011/138682 A2 | 11/2011 |
| WO | 2011/145081 A1 | 11/2011 |
| WO | 2011/149472 A1 | 12/2011 |
| WO | 2011/151723 A2 | 12/2011 |
| WO | 2011/151726 A2 | 12/2011 |
| WO | 2012/012773 A1 | 1/2012 |
| WO | 2012/047941 A2 | 4/2012 |
| WO | 2012/061239 A2 | 5/2012 |
| WO | 2012/082931 A1 | 6/2012 |
| WO | 2012/118321 A2 | 9/2012 |
| WO | 2012/119724 A1 | 9/2012 |
| WO | 2012/160199 A1 | 11/2012 |
| WO | 2013/006569 A2 | 1/2013 |
| WO | 2013/006797 A1 | 1/2013 |
| WO | 2013/016211 A1 | 1/2013 |
| WO | 2013/036907 A1 | 3/2013 |
| WO | 2013/126904 A1 | 8/2013 |
| WO | 2013/135274 A1 | 9/2013 |
| WO | 2013/139655 A1 | 9/2013 |
| WO | 2014/004103 A1 | 1/2014 |
| WO | 2014/013024 A1 | 1/2014 |
| WO | 2014/025771 A2 | 2/2014 |
| WO | 2014/057455 A2 | 4/2014 |
| WO | 2014/086732 A2 | 6/2014 |
| WO | 2014/119953 A1 | 8/2014 |
| WO | 2014/167582 A2 | 10/2014 |
| WO | 2015/021423 A2 | 2/2015 |
| WO | 2015/021806 A1 | 2/2015 |
| WO | 2015/047105 A1 | 4/2015 |
| WO | 2015/048330 A2 | 4/2015 |
| WO | 2015/061584 A1 | 4/2015 |
| WO | 2015/071177 A1 | 5/2015 |
| WO | 2015/073633 A1 | 5/2015 |
| WO | 2015/100344 A1 | 7/2015 |
| WO | 2015/110941 A2 | 7/2015 |
| WO | 2015/126462 A1 | 8/2015 |
| WO | 2015/158776 A1 | 10/2015 |
| WO | 2015/192127 A2 | 12/2015 |
| WO | 2016/063299 A2 | 4/2016 |
| WO | 2016/087941 A1 | 6/2016 |
| WO | 2016/089206 A2 | 6/2016 |
| WO | 2016/100922 A2 | 6/2016 |
| WO | 2016/100926 A1 | 6/2016 |
| WO | 2016/145307 A1 | 9/2016 |
| WO | 2016/157208 A1 | 10/2016 |
| WO | 2016/196846 A2 | 12/2016 |
| WO | 2016/201127 A1 | 12/2016 |
| WO | 2017/004153 A1 | 1/2017 |
| WO | 2017/053374 A1 | 3/2017 |
| WO | 2017/053413 A1 | 3/2017 |
| WO | 2017/156355 A1 | 9/2017 |
| WO | 2019086463 | 5/2019 |

OTHER PUBLICATIONS

Strancar, A. et al., J. Chromatogr. A, 1994, 658, 475-481.
Jonges, M. et al., J. Clin. Microbiol., 2010, 48, 928-940.
Gaik Sui Kee, A thesis submitted to University College London for the degree of Doctor of Philosophy By, Jul. 2009.
Farcet et al., "Antiviral Molecules Inspired by Sea Gods and Mermaids", Advanced Science News, pp. 1-4 (Dec. 13, 2019). https://www.advancedsciencenews.com/antiviral-molecules-inspired-by-sea-gods-and-mermaids-2/.
International Search Report and Written Opinion mailed Apr. 3, 2019 in connection with PCT/EP18/079721.
Li Y. et al., "Microcalorimetric Study on Micellization of Nonionic Surfactants with a Benze Ring or Adamante in Their Hydrophobic Chains" Journal of Physical Chemistry Part B: Condensed Matter, Materials, Surfaces, Interfaces & Biophysical, vol. 109, No. 33, Aug. 1, 2005, pp. 16070-16074.
Conley L., "Evaluation of eco-friendly zwitterionic detergents for enveloped virus inactivation: Eco-Friendly Detergents for Enveloped Virus Inactivation" Biotechnology and Bioengineering, vol. 114, No. 4, Apr. 1, 2017, pp. 813-820.
Tiller G.E. et al., "Hydrogenation of Triton X-1 00 Eliminates Its Fluorescence and Ultraviolet Light Absorption while Preserving Its Detergent Properties", Analytical Biochemistry, vol. 141, Jan. 1, 1984, pp. 262-266.
A.R.Baiguzina, L.I.Galamova, R.I.Khusnutdinov "Synthesis of alkyl-tretbutyl ethers in the presence of zeolite catalysts," Bulletin of Bashkir University 2020 vol. 25.No. 4, p. 748-753.
Papulov Yu.G. "Relationship between properties of substances and the structure of molecules: mathematical modeling" Uspekhi sovremennogo estestvozanya, 2006, N 2, pp. 75-76.
Office Action issued Nov. 25, 2022 in connection with Colombian Application No. NO2020/0006181.
Roberts, Peter L. et al.: "Virus inactivation by solvent/detergent treatment using Triton X-100 in a high purity factor VIII." Biologicals 36 (2008): 330-335.
Yan, Guobing, Yan Zhang and Jianbo Wang: "Recent advances in the synthesis of aryl nitrile compounds." Advanced Synthesis & Catalysis 359 (2017): 4068-4105.
Watts, Henry and Robert Bridges: "Fowne's Manual of Chemistry. Theoretical and Practical." (1878): p. 446.
Brochure "Global Assessment of the Sate-of-the-Science of Endocrine Disruptors" (WHO/PCS/EDC/02.2), published by the International Programme on Chemical Safety of the World Health Organisation, 2002.
Brusentsova et al., "Relative activity of alkenyl-gem-dichlorocyclopropanes in the reactions of hydrogenation and alkylation"; Russian Journal of Applied Chemistry (2009); vol. 82(6); pp. 1029-1032.

(56) References Cited

OTHER PUBLICATIONS

Casimiro-Garcia et al., "Effects of modifications of the linker in a series of phenylpropanoic acid derivatives: Synthesis, evaluation as PPARα/γ dual agonists, and X-ray crystallographic studies"; Bioorganic & Medicinal Chemistry (2008); vol. 16(9); pp. 4883-4907.
Cantillo et al., "A Scalable Procedure for Light-Induced Benzylic Brominations in Continuous Flow"; Journal of Organic Chemistry (2014); vol. 79(1); pp. 223-229.
Casey Joseph et al., "Detergent interaction with band 3, a model polytopic membrane protein"; Biochemistry (1993); vol. 32; pp. 1172-1179.
Chen et al, Organic Letters (2012); vol. 14(12); pp. 2992-2995.
Chen et al., Chinese Chemical Letters (1992); vol. 3(4); pp. 257-258.
Di Serio et al., "Comparison of Different Reactor Types Used in the Manufacture of Ethoxylated, Propoxylated Products"; Ind. Eng. Chem. Res. (2005); vol. 44(25); pp. 9482-9489.
Dichtelmüller et al., "Robustness of solvent/detergent treatment of plasma derivatives: a data collection from Plasma Protein Therapeutics Association member companies"; Transfusion (2009); vol. 49(9); pp. 1931-1943.
Dong et al., Colloids and Surfaces, A: Physicochemical and Engineering Aspects (2014); vol. 444; pp. 257-268.
ECHA, SVHC Support Document—4-(1,1,3,3-Tetramethylbutyl)Phenol, Ethoxylated, Dec. 12, 2012.
Gaunt et al., Journal of Organic Chemistry (1998); vol. 63(13); pp. 4172-4173.
Guo et al., Hebei Daxue Xuebao, Ziran Kexueban (1990); vol. 10(4); pp. 27-31.
Handlon et al., Synlett (2005); vol. (1); pp. 111-114.
Huebener et al., "Anellated hemicyanine dyes with large symmetrical solvatochromism of absorption and fluorescence"; Journal of Physical Chemistry B (2003); vol. 107(31); pp. 7896-7902.
Khanal et al., "Solid Phase Stepwise Synthesis of Polyethylene Glycols"; Chemistry—A European Journal (2017); vol. 23(60); pp. 15133-15142.
Khusnutdinov et al., "Alkylation of aromatic compounds with 1-bromoadamantane in the presence of metal complex catalysts"; Russian Journal of Organic Chemistry (2015); vol. 51(11); pp. 1545-1550.
Machin et al., Journal of Medicinal Chemistry (1983); vol. 26(11); pp. 1570-1576.
Mamedov et al., Azerbaidzhanskii Khimicheskii Zhurnal (1964); vol. (3); pp. 75-82.
Mondini et al., "Magnetic nanoparticles conjugated to chiral imidazolidinone as recoverable catalyst"; Journal of Nanoparticle Research (2013); vol. 15(11); 2025/1-2025/12, 12 pp.
Nakhate et al., ACS Sustainable Chemistry & Engineering (2016); vol. 4(4); pp. 1963-1973.
Nutaitis et al., Organic Preparations and Procedures International (1985); vol. 17(1); pp. 11-16.
Partearroyo et al., "Surfactant-induced cell toxicity and cell lysis"; Biochemical Pharmacology (Sep. 1990); vol. 40; pp. 1323-1328.
Poelsler et al., "A new liquid intravenous immunoglobulin with three dedicated virus reduction steps: virus and prion reduction capacity"; Vox Sanguinis (2008); vol. 94; pp. 184-192.
Simons et al., "Solubilization of the Membrane Proteins from Semliki Forest Virus with Triton X100"; J. Mol. Biol. (1973); vol. 80; pp. 119-133.
Srikrishna et al., Tetrahedron (1995); vol. 51(11); pp. 3339-3344.
Sun et al., Journal of the Textile Institute, Part 1: Fibre Science and Textile Technology (1998); vol. 89(4); pp. 677-685.
Sun, C. & Baird, M., "The Determination of Alkyl Phenol Ethoxylates in Wool-scouring Effluent"; J. Text. Inst. (1998); 89:4; pp. 677-685.
Teduka et al., Synlett (2005); vol. (6); pp. 923-926.
Tsuda et al., Makromolekulare Chemie (1973); vol. 167; pp. 183-190.
Tiller et al., "Hydrogenation of Triton X-100 eliminates its fluorescence and ultraviolet light absorption while preserving its detergent properties"; Analytical Biochemistry (Aug. 1984); vol. 141; pp. 262-266.
Ueno et al., "Synthesis and Structure-Activity Relationships of Novel Selective Factor Xa Inhibitors with a Tetrahydroisoquinoline Ring"; Journal of Medicinal Chemistry (2005); vol. 48(10); pp. 3586-3604.
Vogel et al., Vogel's Textbook of Practical Organic Chemistry ((5th Edition, 1989).
Wang et al., Youtian Huaxue (2009); vol. 26(4); pp. 357-361.
Wang et al., Jingxi Huagong (2007); vol. 24(2); pp. 145-148.
Wang et al., "Synthesis and surface properties of several nonionic-anionic surfactants with straight chain alkyl-benzyl hydrophobic group", Colloids and Surfaces, A: Physicochemical and Engineering Aspects (2007); vol. 302(1-3); pp. 532-539.
Zhang et al., Angewandte Chemie, International Edition (2016); vol. 55(5); pp. 1872-1875.
Conley et al., "Evaluation of Eco-Friendly Zwitterionic Detergents for Enveloped Virus Inactivation", Biotechnoloy and Bioengineering, vol. 114, No. 4, pp. 813-820, Apr. 2017.
Farcet et al., "Development of a Triton X-100 replacement for effective virus inactivation in biotechnology processes", Wiley, Engineering Reports, 2019;1:e12078, pp. 1-10. https://doi.org/10.1002/eng2.12078.
Halogenation Reagents, 6 pages, www.TCIchemicals.com; R5105E Jul. 13, 2018.
International Search Report and Written Opinion issued in International Application No. PCT/EP2018/079721, mailed Apr. 3, 2019.
Search results A Feb. 9, 2018.
Search results B Feb. 9, 2018.
Search results C Feb. 9, 2018.
Search results D Feb. 9, 2018.
Search results E Feb. 9, 2018.
Li et al., "Microcalorimetric Study on Micellization of Nonionic Surfactants with a Benzene Ring or Adamantane in Their Hydrophobic Chains", J. Phys. Chem. B 2005, vol. 109, No. 33, pp. 16070-16075.
Office Action issued Aug. 29, 2022 in connection with Chinese Application No. 201880083488.5.
Search Report issued Oct. 13, 2022 in connection with Chinese Application No. 201880083488.5.
Brown et al.; Bioisosteres in Medicinal Chemistry. New York: Wiley & Sons; 2012.
Flick; Industrial Surfactants Elsevier Science, 2nd edn., 1988, Elsevier Science; 1988.
Fu et al.; Perfluorooctanesulfonic acid catalyzed Friedel-crafts alkylation with olefins in gas-liquid phase, Chinese Chemical Letters, 4(4), 307-10; 1993.
Howard; Handbook of Environmental Fate and Exposure Data for Organic Chemicals, vol. IV. Solvents 2., CRC Press, 1993.
Mannhold et al.; Bioisosteres in Medicinal Chemistry, John Wiley & Sons, 2012.
Unger at al.; Virus inactivation during the freeze-drying processes as used for the manufacture of plasma-derived medicinal products. Transfusion. 2009;49:1924-30.
Hearing Notice issued Nov. 2, 2023 in connection with Indian Application No. 202017019999.
ECHA; 12 new substances added to the Authorisation List, https://echa.europa.eu/en/-/reach-authorisation-list-updated, (accessed Apr. 25, 2019).
"ECHA; Support document for identification of 4-(1,1,3,3-tetramethylbutyl)phenol, ethoxylated as substances ofvery high concern because, due to their degradation to a substance of very high concern (4-(1,1,3,3-tetramethylbutyl) phenol) with endocrine disrupting properties, they cause probable serious effects to theenvironment which give rise to an equivalent level of concern to those of CMRs and PBTs/vPvBs, adopted onDec. 12, 2012."
Bernard et al., "Atmospheric chemistry of benzyl alcohol: kinetics and mechanism of reaction with OH radicals," Environmental Science & Technology, 2013, 47, pp. 3182-3189.
Burger A., "Isosterism and bioisosterism in drug design," Progress in Drug Research, 1991;37, pp. 287-371.

(56) References Cited

OTHER PUBLICATIONS

Burnouf T., "Modern plasma fractionation," Transfusion Medicine Reviews, 2007, vol. 21, No. 2, pp. 101-117.

Casimiro-Garcia A. et al., "Effects of modifications of the linker in a series of phenylpropanoic acid derivatives: Synthesis, evaluation as PPARa/y dual agonists, and X-ray crystallographic studies," Bioorganic & Medicinal Chemistry, 2008, vol. 16, No. 9, pp. 4883-4907.

CPMP / EMA; Note for Guidance on Virus Validation Studies: The Design, Contribution and Interpretation of Studies Validating the Inactivation and Removal of Viruses (CPMP/BWP/268/95/rev), 1996.

EMA; Guideline on plasma-derived medicinal products (EMA/CHMP/BWP/706271/2010), 2011.

Farcet J. et al., "Development of a Triton X-100 replacement for effective virus inactivation in biotechnology processes," Engineering Reports, 2019; pp. 1-5.

Farcet J. et al., "Synthesis of 'Nereid', a new phenol-free detergent to replace Triton X-100 in virus inactivation," Journal of Medicinal Virology, 2021; 93, pp. 3880-2889.

FDA; BAM R86: Triton X-100. 1998. https://www.fda.gov/food/laboratory-methods-food/bam-r86-triton-x-100. (Accessed Nov. 25, 2020).

Guha R., "On exploring structure-activity relationships," Methods Mol Biol. 2013; 993, pp. 81-94.

Hirose K. et al., "Highly Selective and High-Yielding Rotaxane Synthesis via Aminolysis of Prerotaxanes Consisting of a Ring Component and a Stopper Unit," Organic Letters, 9(16), pp. 2969-2972; 2007.

Horowitz et al., "Inactivation of viruses in labile blood derivatives. I. Disruption of lipid-enveloped viruses by tri(n-butyl)phosphate detergent combinations," Transfusion, 1985, 25, pp. 516-522.

Jobling S. et al., "Inhibition of testicular growth in rainbow trout (*Oncorhynchus mykiss*) exposed to estrogenic alkylphenolic chemicals," Environmental Toxicology and Chemistry, 1996, vol. 15, No. 2, pp. 194-202.

Kiasat et al., "Investigation of Friedel-Crafts Alkylation in the Presence of Supported Sulfonic Acid on Silica Gel," e-Journal of Chemistry, 9(4), pp. 1875-1884; 2012.

Lee W. Y. et al., "New aromatic biscorands : regioselective synthesis of common-nuclear-bis-o-xylyl crowns," Synlett, (2), pp. 157-159; 1992.

Luo et al., "Identification and characterization of a Triton X-100 replacement for virus inactivation," Biotechnology Progress, 2020:e3036, pp. 1-11.

Nicolson G. L., "The Fluid-mosaic model of membrane structure: still relevant to understanding the structure, function and dynamics of biological membranes after more than 40 years," Biochimica et Biophysica Acta, 2014, 1838, pp. 1451-1466.

Sankar M. et al., "The benzaldehyde oxidation paradox explained by the interception of peroxy radical by benzyl alcohol," Nature Communications, 2014, pp. 1-5, 3332.

Suarez et al., "Benzylic Brominations with N-Bromosuccinimide in (Trifluoromethyl)benzene," Synthesis, Nov. 2009, pp. 1807-1810.

Brochure; "Halogenation Reagents", TCI Chemistry, www.TCIchemicals.com, 2022.

White et al., "Environmentally persistent alkylphenolic compounds are estrogenic," Endocrinology, 1994, 135, pp. 175-182.

WHO; Concise International Chemical Assessment Document 26. Benzoic Acid and Sodium Benzoate. 2000.

Wieser et al., "Virus filtration and flow variation: an approach to evaluate any potential impact on virus retention," PDA Journal of Pharmaceutical Science and Technology, 2016, 70, pp. 325-331.

Yamauchi et al., "Selenium and Tellurium Tetrachlorides as Reagents for the Conversion of Alcohols to Alkyl Chlorides," Bulletin of the Chemical Society of Japan, 59(11), pp. 3617-3620; 1986.

Yoshioka et al., "Degradations of phenol, benzoic acid and their derivatives by microbial populations in sea water," Mircrobes and Environments, 1997; 12(4), pp. 117-123.

Zupp et al., "Microwave-assisted silica-supported aluminum chloride-catalyzed Friedel-Crafts alkylation," Tetrahedron Letters, 53(39), pp. 5343-5346; 2012.

International Search Report and Written Opinion mailed Sep. 11, 2021 in connection with PCT/IB2021/057190.

ICH harmonised Tripartite Guideline Viral Safety Evaluation of Biotechnology Products derived from Cell Lines of Human or Animal Origin Q5A(R1), 1999.

Office Action issued Aug. 6, 2024 in connection with Application No. NC2020/0006181.

Guo et al., "Selective liquid phase oxidation of toluene with air" Applied Catalysis A: General 282 (2005) 55-59.

\* cited by examiner

FIG. 7

A  BVDV

B  BVDV

A

B

A  X-MuLV

B  X-MuLV

ENVIRONMENTALLY COMPATIBLE DETERGENTS FOR INACTIVATION OF LIPID-ENVELOPED VIRUSES

CROSS REFERENCE TO RELATED APPLICATIONS

This application is a 371 National Stage of PCT/EP2018/079721, filed Oct. 30, 2018, which claims priority pursuant to 35 U.S.C. § 119(e) to U.S. Provisional Patent Application Nos. 62/578,648, filed Oct. 30, 2017 and 62/687,023, filed Jun. 19, 2018, which are all hereby incorporated by reference in their entirety.

FIELD OF THE INVENTION

The present invention relates to methods for inactivating a lipid-enveloped virus using environmentally compatible detergents, and to methods for preparing a biopharmaceutical drug using environmentally compatible detergents. The invention also provides environmentally compatible detergents.

BACKGROUND

The use of biopharmaceutical drugs has continued to increase in importance as a method of treating many diseases, disorders, or conditions that affect an individual's health. Biopharmaceutical drugs are typically obtained by purification from a biological fluid or through recombinant production in host cells such as mammalian cell lines. However, in such biopharmaceutical production processes, viral contamination poses a significant problem. Viral contamination can be introduced to the biopharmaceutical production process by the biological fluids to be purified, or through the use of animal-derived products. In contrast to bacterial contamination, viral contamination is difficult to detect. However, if viral contamination goes unnoticed and infectious virus is incorporated into the formulation of the biopharmaceutical drug, it poses a significant health risk to patients. Therefore, viral inactivation is of paramount importance in biopharmaceutical production.

In many biopharmaceutical production processes, detergents are used for virus inactivation. Often, these detergents are combined with solvents in a so-called solvent/detergent (S/D) treatment. The detergent Triton X-100 has been used for many years for S/D treatment of commercial products.

However, recent ecological studies have suggested that Triton X-100 and its break-down products can potentially behave as endocrine disrupters in aquatic organisms, raising concerns from an environmental impact perspective (see "ECHA Support document for identification of 4-(1,1,3,3-tetramethylbutyl)phenol, ethoxylated as substances of very high concern because, due to their degradation to a substance of very high concern (4-(1,1,3,3-tetramethylbutyl)phenol) with endocrine disrupting properties, they cause probable serious effects to the environment which give rise to an equivalent level of concern to those of CMRs and PBTs/vPvBs", adopted on 12 Dec. 2012). As a consequence, alternative, environmentally compatible detergents for viral inactivation are required.

DESCRIPTION OF THE INVENTION

The present invention meets the above-described needs and solves the above-mentioned problems in the art by providing the embodiments described below:

The toxic activity of Triton-X100 arises from the phenol moiety that has the ability to dock in certain endocrine receptors of marine life organisms. Consistently, based on in silico predictions of endocrine disruptor activity, for none of the non-phenolic polyoxyethylene ether detergents according to the present invention any evidence has been found that they are active as endocrine disruptors.

The present inventors have surprisingly found that environmentally compatible, non-phenolic polyoxyethylene ether detergents such as Triton X-100 reduced, Triton N-101 reduced and Brij C10 efficiently inactivate lipid-enveloped viruses in S/D treatment. The inventors have also synthesized an environmentally compatible, non-phenolic polyoxyethylene ether detergent that efficiently inactivates lipid-enveloped viruses in S/D and single-detergent treatment. Hence, the inventors found that environmentally compatible, non-phenolic polyoxyethylene ether detergents can be used in the methods for inactivating lipid-enveloped viruses of the present invention.

Accordingly, the present invention provides environmentally compatible, non-phenolic polyoxyethylene ether detergents as well as improved means for inactivating lipid-enveloped viruses by providing the preferred embodiments described below:

1. A compound of the following general Formula (VIII):

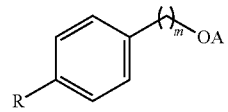

Formula (VIII)

wherein
R represents a hydrocarbon group having a linear chain of 2 to 12 carbon atoms and one or more methyl groups as substituents on said linear chain,
m represents an integer of 1 to 4, and
A represents a polyoxyethylene residue.
2. The compound of item 1, wherein A represents a polyoxyethylene residue comprising 4 to 16 oxyethylene units, preferably 9 or 10 oxyethylene units.
3. The compound of item 1 or 2, wherein m equals 1.
4. The compound of any of items 1 to 3, wherein R represents a hydrocarbon group having a linear chain of 2 to 6 carbon atoms and one or more methyl groups as substituents on said linear chain.
5. The compound of any of items 1 to 4, wherein R represents a hydrocarbon group having a linear chain of 2 to 6 carbon atoms and 2 to 4 methyl groups as substituents on said linear chain.
6. The compound of any of items 1 to 5, wherein R represents a hydrocarbon group having a linear chain of 4 carbon atoms and 4 methyl groups as substituents on said linear chain.
7. The compound of any of items 1 to 6, wherein R represents a 2,4,4-trimethyl-pent-2-yl group.
8. The compound of item 1 wherein the compound of Formula (VIII) is the following compound:

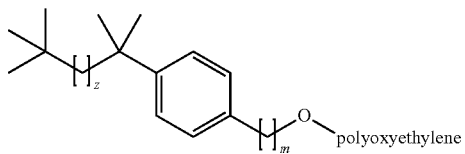

wherein m and z are integers that are independently selected from the following groups:
m=1 to 4
z=1 to 5.
9. The compound of item 8 wherein m is equal to 1.
10. The compound of item 1 wherein the compound of Formula (VIII) is the following compound:

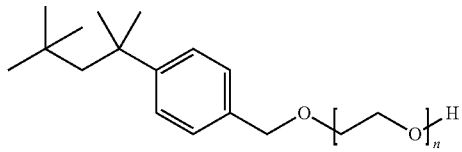

wherein n is an integer between 4 and 16, preferably wherein n is equal to 9 or 10.
11. The compound of any of items 1 to 10 with the proviso that 29-[4-(1,1,3,3-tetramethylbutyl)phenyl]-3,6,9,12,15,18,21,24,27-nonaoxanonacosan-1-ol having the following structural formula is excluded:

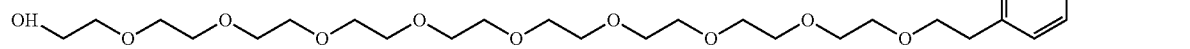

12. A method for inactivating a virus having a lipid envelope, the method comprising the following steps:
   a) Adding a detergent to a liquid to prepare a mixture of said detergent and said liquid; and
   b) Incubating said mixture to inactivate said virus;
   wherein said detergent is a polyoxyethylene ether, and wherein said detergent is a non-phenolic detergent.
13. The method of item 12, wherein said detergent is environmentally compatible.
14. The method of item 12 or 13, wherein said detergent is a non-ionic detergent.
15. The method of any of items 12 to 14, wherein said detergent is the compound of any of items 1 to 11.
16. The method of any of items 12 to 14, wherein said detergent is a polyoxyethylene alkyl ether.
17. The method of item 16, wherein said polyoxyethylene alkyl ether is a polyoxyethylene cycloalkyl ether.
18. The method of item 17, wherein the cycloalkyl moiety of said polyoxyethylene cycloalkyl ether is an alkyl-substituted cycloalkyl moiety.
19. The method of item 18, wherein said alkyl-substituted cycloalkyl moiety is a branched-alkyl-substituted cycloalkyl moiety.
20. The method of any of items 17 to 19, wherein said polyoxyethylene cycloalkyl ether is a polyoxyethylene cyclohexyl ether.
21. The method of any of items 17 to 20, wherein said polyoxyethylene cycloalkyl ether is not a heterocyclic polyoxyethylene cycloalkyl ether.
22. The method of any of items 12 to 14 and 16 to 21, wherein said detergent has the following structure according to Formula (I):

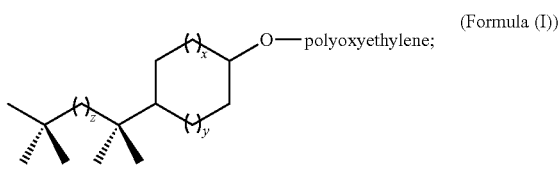

(Formula (I))

wherein x, y and z are integers that are independently selected from the following groups:
x=0 to 5
y=0 to 5
z=0 to 20
23. The method of item 22, wherein said detergent has the following structure according to Formula (II):

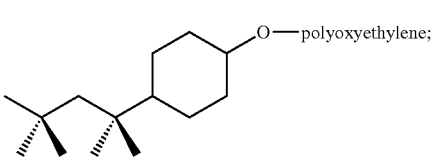

(Formula (II))

24. The method of item 23 wherein said detergent has the following structure according to Formula (III):

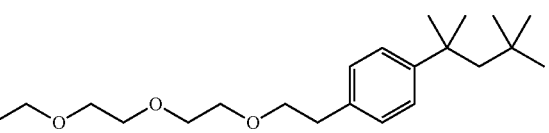

(Formula (III))

wherein n is an integer between 4 and 16.
25. The method of item 24, wherein n is equal to 9 or 10.
26. The method of item 22, wherein said detergent has the following structure according to Formula (IV):

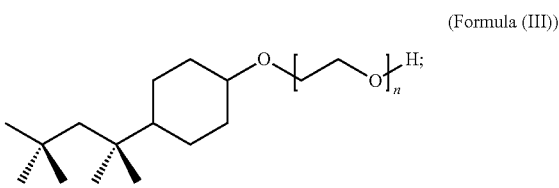

(Formula (IV))

27. The method of item 26, wherein said detergent has the following structure according to Formula (V):

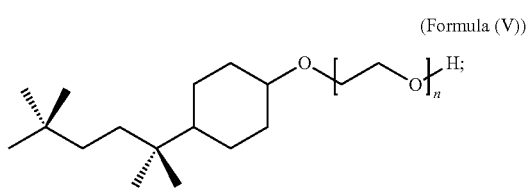
(Formula (V))

wherein n is an integer between 4 and 16.
28. The method of item 27, wherein n is equal to 9 or 10.
29. The method of any of items 12 to 14 and 16, wherein said detergent is a linear polyoxyethylene alkyl ether.
30. The method of item 29, wherein said detergent is a linear polyoxyethylene hexadecyl ether.
31. The method of item 30, wherein said detergent has the following structure according to Formula (VI):

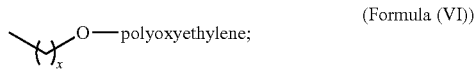
(Formula (VI))

wherein x equals 15.
32. The method of item 31, wherein said detergent has the following structure according to Formula (VII):

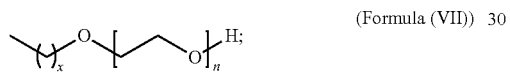
(Formula (VII))

wherein x equals 15 and wherein n is an integer between 5 and 15.
33. The method of item 32, wherein n is equal to 10.
34. The method of any of items 12 to 33, wherein said detergent is suitable for the inactivation of said virus.
35. The method of any of items 12 to 34, wherein in step a), no organic solvent is added to said liquid.
36. The method of any of items 12 to 34, wherein step a) further comprises adding a solvent to said liquid, and wherein in step a), a solvent/detergent mixture for inactivation of said virus is prepared by adding said detergent and said solvent to said liquid.
37. The method of item 36, wherein said solvent is an organic solvent.
38. The method of item 36 or 37, wherein said solvent is Tri-n-butyl phosphate.
39. The method of any one of items 12 to 38, wherein in step a), no further detergent other than said detergent is added.
40. The method of any one of items 12 to 38, wherein in the method, no further detergent other than said detergent is added.
41. The method of any of items 12 to 38, wherein step a) further comprises adding a further detergent to said liquid.
42. The method of item 41, wherein said further detergent is polysorbate 80.
43. The method of any of items 12 to 42, wherein said liquid comprises a biological medicinal product.
44. The method of any of items 12 to 43, wherein said liquid comprises a biopharmaceutical drug.
45. The method of item 44, wherein said biopharmaceutical drug is not a viral vaccine.
46. The method of any of items 44 or 45, wherein said biopharmaceutical drug is a blood factor, immunoglobulin such as monoclonal antibody, replacement enzyme, vaccine, gene therapy vector, growth factor or a growth factor receptor.
47. The method of any of items 44 to 46, wherein said biopharmaceutical drug is a therapeutic protein.
48. The method of any of items 44 to 47, wherein said biopharmaceutical drug is a blood factor, and wherein said blood factor is factor I (fibrinogen), factor II (prothrombin), Tissue factor, factor V, factor VII or VIIa, factor VIII, factor IX, factor X, factor X, factor XII, factor XIII, von Willebrand Factor (VWF), prekallikrein, high-molecular-weight kininogen (HMWK), fibronectin, antithrombin III, heparin cofactor II, protein C, protein S, protein Z, plasminogen, alpha 2-antiplasmin, tissue plasminogen activator (tPA), urokinase, plasminogen activator inhibitor-1 (PAI1), or plasminogen activator inhibitor-2 (PAI2).
49. The method of any of items 44 to 48, wherein said biopharmaceutical drug is factor VIII, preferably recombinant human factor VIII.
50. The method any of items 44 to 47, wherein said biopharmaceutical drug is an immunoglobulin, and wherein said immunoglobulin is an immunoglobulin from human plasma or a monoclonal antibody.
51. The method of any of items 12 to 50, wherein prior to step a) or between step a) and step b), said method further comprises a step of filtering said liquid or mixture with a depth filter.
52. The method of any of items 12 to 51, wherein in step b), said mixture is incubated for at least 1 hour.
53. The method of any of items 12 to 52, wherein in step b), said mixture is incubated at a temperature of between 0° C. and 10° C., or wherein said mixture is incubated at a temperature of between 16° C. and 25° C.
54. The method of any of items 44 to 53, further comprising, after step b), a step of
c) Purifying said biopharmaceutical drug.
55. The method of item 54, wherein said purifying comprises separating said biopharmaceutical drug from said detergent.
56. The method of item 54 or 55, wherein said purifying comprises separating said biopharmaceutical drug from said further detergent.
57. The method of any of items 54 to 56, wherein said purifying of said biopharmaceutical drug comprises purifying said biopharmaceutical drug by at least one chromatographic purification.
58. The method of any of items 54 to 57, wherein said at least one chromatographic purification is by anion exchange chromatography and/or by cation exchange chromatography.
59. A method for preparing a biopharmaceutical drug, said method comprising the method according to any one of items 44 to 58, wherein said biopharmaceutical drug is as defined in any one of said items 44 to 58.
60. The method of item 59, further comprising, after said method of any one of items 44 to 58, a step of preparing a pharmaceutical formulation comprising said biopharmaceutical drug.
61. Use of a detergent as defined in any one of items 12 to 34 in a method for the inactivation of a virus having a lipid envelope.
62. The use of item 61, wherein in said use, no further detergent other than said detergent is used.

63. The use of item 61 or 62, wherein in said use, no organic solvent is used.
64. The use of item 61, wherein said method for said inactivation of said virus is a method using a solvent/detergent treatment, said solvent/detergent treatment comprising the use of said detergent as defined in any one of items 12 to 34.
65. The use of any of items 61 to 64, wherein said virus inactivation is an inactivation of virus in a liquid comprising a biopharmaceutical drug as defined in any one of items 44 to 50.
66. A composition comprising a detergent as defined in any one of items 12 to 34.
67. A detergent as defined in any one of items 12 to 34.
68. The composition of item 66, further comprising a biopharmaceutical drug as defined in any one of items 44 to 50.
69. The composition of item 66 or 68, wherein the composition does not comprise any organic solvent.
70. The composition of item 66 or 68, further comprising an organic solvent as defined in any one of items 37 and 38.
71. The composition of any of items 66 or 68 to 70, wherein the composition does not comprise any further detergent other than said detergent.
72. The composition of any of items 66 or 68 to 70, further comprising a further detergent as defined in any one of items 41 and 42.
73. A kit for virus inactivation, comprising the detergent of item 67 or the composition of any of the preceding items, and further comprising a chromatography resin for a chromatographic purification as defined in any one of items 57 to 58.
74. The kit of item 73, further comprising a depth filter.
75. A method for synthesizing a compound of the following general Formula (VIII),

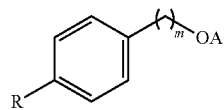

Formula (VIII)

wherein
R represents a hydrocarbon group having a linear chain of 2 to 12 carbon atoms and one or more methyl groups as substituents on said linear chain,
m represents an integer of 1 to 4, and
A represents a polyoxyethylene residue,
wherein the method comprises the steps of
A) Converting a phenol of the following general Formula (IX) wherein R is as defined above

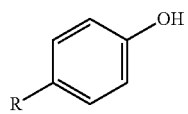

Formula (IX)

into an alcohol of the of the following general Formula (X) wherein R and m are as defined above

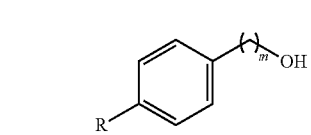

Formula (X)

and
(B) converting the alcohol of the general Formula (X) into a polyoxyethylene ether of the general Formula (VIII) as defined above.
76. A method for synthesizing a compound of the following general Formula (VIII),

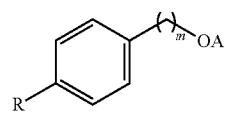

Formula (VIII)

wherein
R represents a hydrocarbon group having a linear chain of 2 to 12 carbon atoms and one or more methyl groups as substituents on said linear chain,
m represents an integer of 1 to 4, and
A represents a polyoxyethylene residue,
wherein the method comprises the steps of
(1) reacting toluene so as to obtain a substituted toluene of the following general Formula (XI) wherein R is as defined above

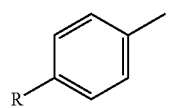

Formula (XI)

(2) converting the substituted toluene of the general Formula (XI) into a compound of the following general Formula (XII), wherein R and m are as defined above and X is selected from the group comprising a hydroxyl group, a bromine atom, an iodine atom and a chlorine atom

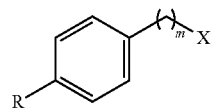

Formula (XII)

and
(3) converting the compound of the general Formula (XII) into a polyoxyethylene ether of the general Formula (VIII) as defined above.
77. A method for synthesizing a compound of the following general Formula (VIIIa),

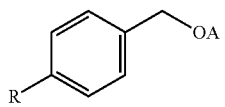

Formula (VIIIa)

wherein
R represents a hydrocarbon group having a linear chain of 2 to 12 carbon atoms and one or more methyl groups as substituents on said linear chain, and
A represents a polyoxyethylene residue,
wherein the method comprises the steps of
(I) converting benzyl alcohol into a compound of the following general Formula (XIII), wherein R is as defined above

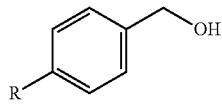

Formula (XIII)

and
(II) converting the compound of the general Formula (XIII) into a polyoxyethylene ether of the general Formula (VIIIa) as defined above.

78. The method of any of items 75 to 77, wherein A represents a polyoxyethylene residue comprising 4 to 16 oxyethylene units.
79. The method of item 78, wherein A represents a polyoxyethylene residue comprising 8 to 10 oxyethylene units.
80. The method of item 78, wherein A represents a polyoxyethylene residue comprising 9 or 10 oxyethylene units.
81. The method of any of items 75, 76 and 78 to 80, wherein m equals 1.
82. The method of any of items 75 to 81, wherein R represents a hydrocarbon group having a linear chain of 2 to 6 carbon atoms and one or more methyl groups as substituents on said linear chain.
83. The method of any of items 75 to 82, wherein R represents a hydrocarbon group having a linear chain of 2 to 6 carbon atoms and 2 to 4 methyl groups as substituents on said linear chain.
84. The method of any of items 75 to 83, wherein R represents a hydrocarbon group having a linear chain of 4 carbon atoms and 4 methyl groups as substituents on said linear chain.
85. The method of any of items 75 to 84, wherein R represents a 2,4,4-trimethyl-pent-2-yl group.
86. The method of any of items 75 to 77 wherein the compound of Formula (VIII) is the following compound:

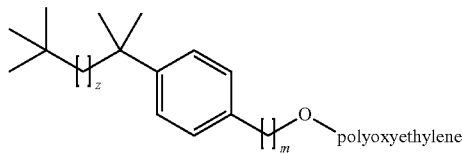

wherein m and z are integers that are independently selected from the following groups:
m=1 to 4
z=1 to 5.
87. The method of item 86 wherein m is equal to 1.
88. The method of any of items 75 to 77 wherein the compound of Formula (VIII) is the following compound:

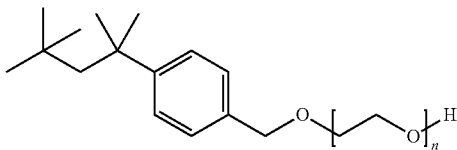

wherein n is an integer between 4 and 16, preferably wherein n is equal to 9 or 10.
89. The method of any of items 76 and 78 to 88, wherein the converting in step (2) is a radical reaction using AIBN (Azobis(isobutyronitrile) as a radical initiator.
90. The method of any of items 76 and 78 to 89, wherein X is a bromine atom.
91. The method of any of items 76 and 78 to 90, wherein the converting in step (2) uses N-bromosuccinimide (NBS) as a reagent.
92. The method of any of items 76 and 78 to 91, wherein the converting in step (3) uses TBME (methyl-tert-butylether) as a solvent.
93. The method of any of items 76 and 78 to 92, wherein the converting in step (3) takes place for at least 2 hours, preferably at ambient temperature.
94. The method of any of items 76 and 78 to 93, wherein the converting in step (3) takes place for not more than 5 hours, preferably at ambient temperature.
95. The method of any of items 76 and 78 to 94, wherein the converting in step (3) takes place for 3 hours, preferably at ambient temperature.
96. The method of any of items 75 to 95, wherein the method is carried out at a scale which yields at least 100 g, at least 1 kg, at least 10 kg, at least 100 kg or at least 1000 kg of said compound of said Formula (VIII).

0.02% Polysorbate 80, 0.01%-0.02% TnBP (side-by-side comparison with same concentration of Triton X-100). Virus inactivation over time is indicated by the virus reduction factor (RF) for two runs with HIV (A and B, respectively). Virus inactivation of S/D treatment using Brij C10 was compared to virus inactivation of S/D treatment using Triton X-100 ("TX-100").

Figure 4:
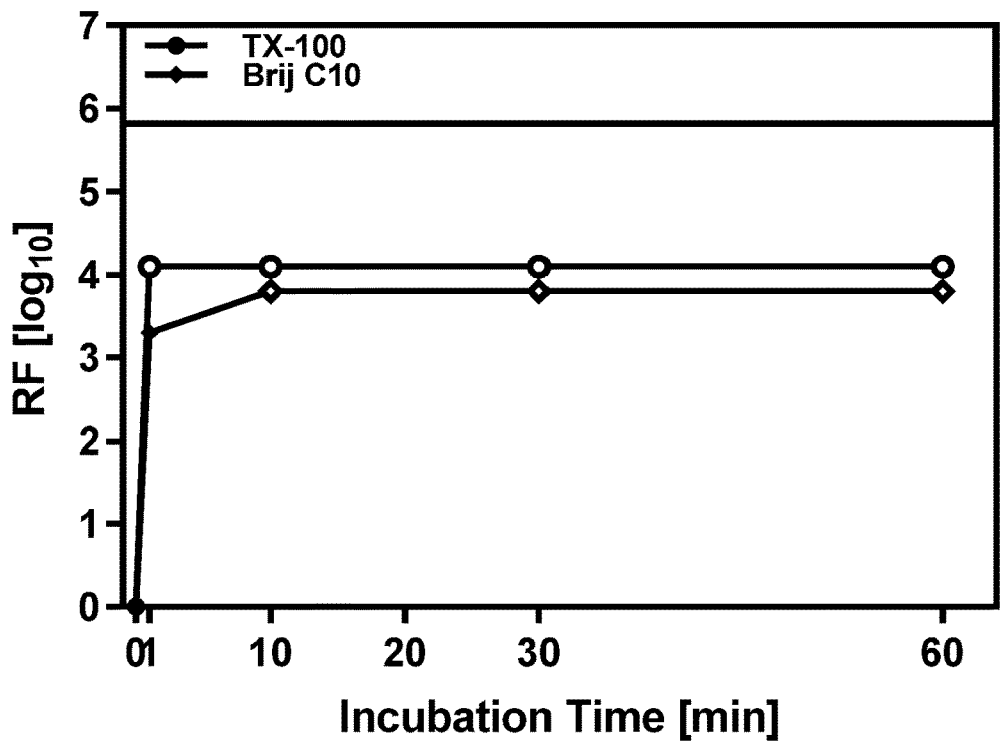
Figure 4:
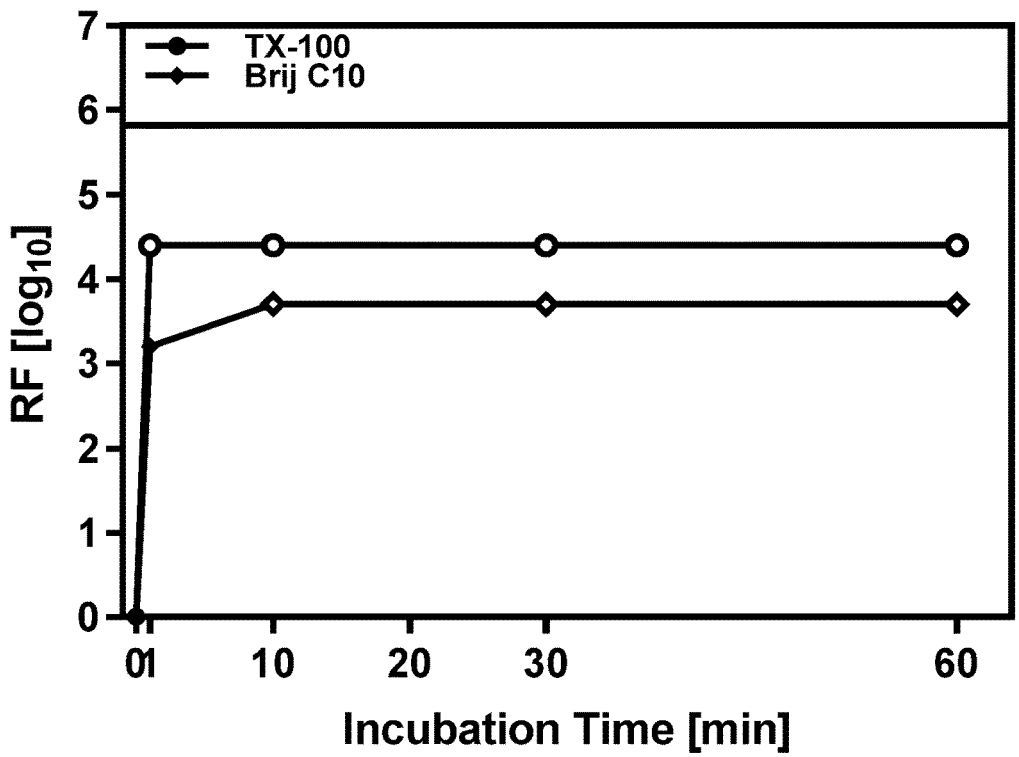

FIG. 4: Virus inactivation efficiency of low concentrations of Brij C10 in S/D treatment of IVIG-containing liquid at 17° C.±1° C. A three-component mixture was used to give final concentrations of 0.04%-0.06% Brij C10, 0.01%-0.02% Polysorbate 80, 0.01%-0.02% TnBP (side-by-side comparison with same concentration of Triton X-100). Virus inactivation over time is indicated by the virus reduction factor (RF) for two runs with PRV (A and B, respectively). Virus inactivation of S/D treatment using Brij C10 was compared to virus inactivation of S/D treatment using Triton X-100 ("TX-100").

Figure 5:
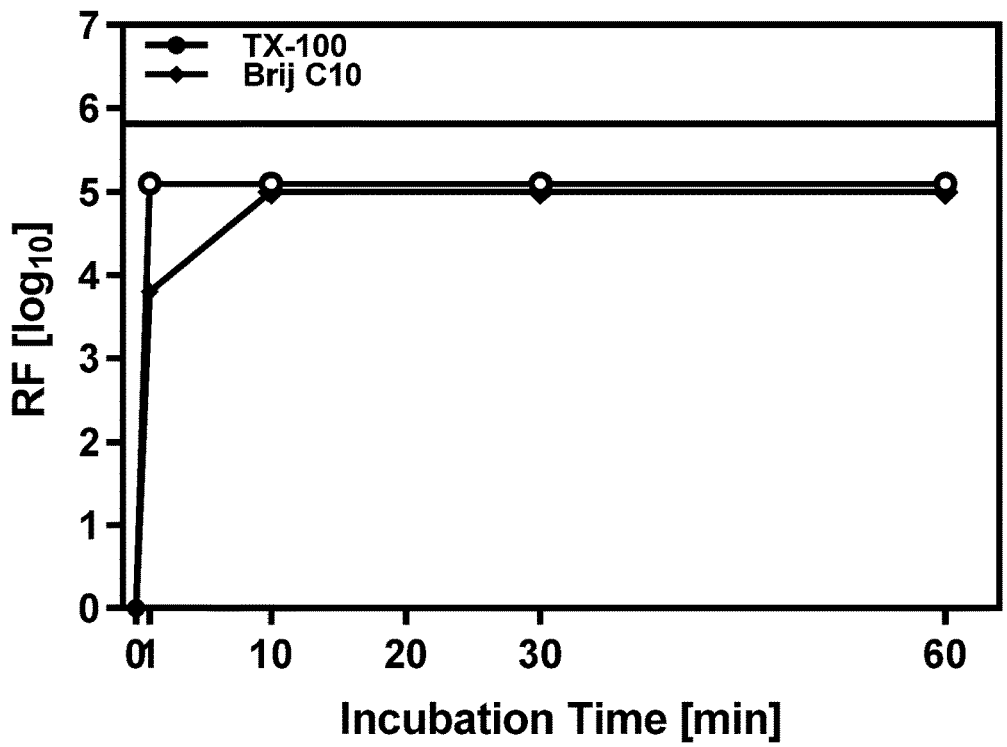
Figure 5:
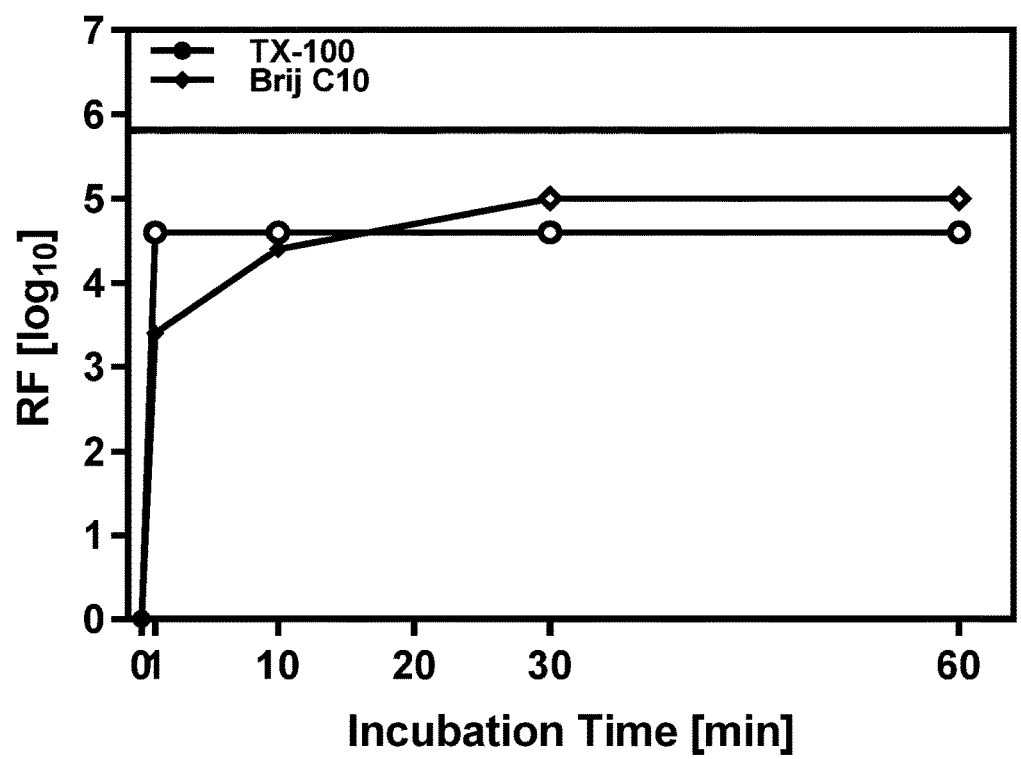

FIG. 5: Virus inactivation efficiency of low concentrations of Brij C10 in S/D treatment of IVIG-containing liquid at 17° C.±1° C. A three-component mixture was used to give final concentrations of 0.04%-0.06% Brij C10, 0.01%-0.02% Polysorbate 80, 0.01%-0.02% TnBP (side-by-side comparison with same concentration of Triton X-100). Virus inactivation over time is indicated by the virus reduction factor (RF) for two runs with BVDV (A and B, respectively). Virus inactivation of S/D treatment using Brij C10 was compared to virus inactivation of S/D treatment using Triton X-100 ("TX-100").

Figure 6:
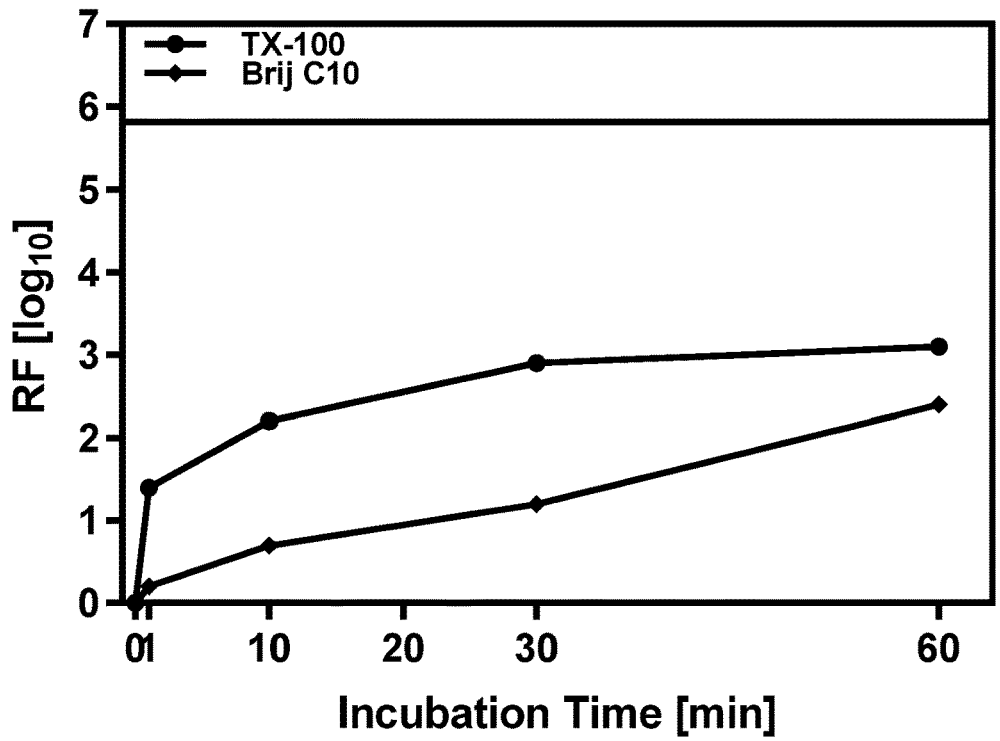
Figure 6:
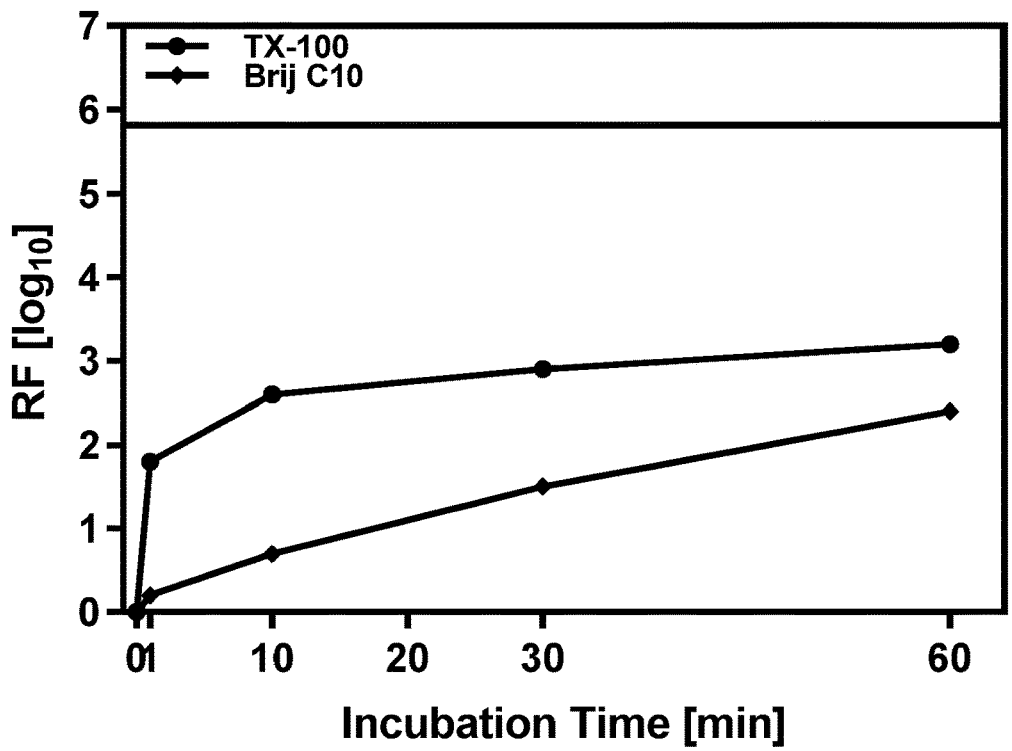

FIG. 6: Virus inactivation efficiency of low concentrations of Brij C10 in S/D treatment of human serum albumin (HSA)-containing liquid at 1° C.±1° C. A three-component mixture was used to give final concentrations of 0.08%-0.1% Brij C10, 0.02%-0.03% Polysorbate 80, 0.02%-0.03% TnBP (side-by-side comparison of Triton X-100). Virus inactivation over time is indicated by the virus reduction factor (RF) for two runs with X-MuLV (A and B, respectively). Virus inactivation of S/D treatment using Brij C10 was compared to virus inactivation of S/D treatment using Triton X-100 ("TX-100").

Figure 7:
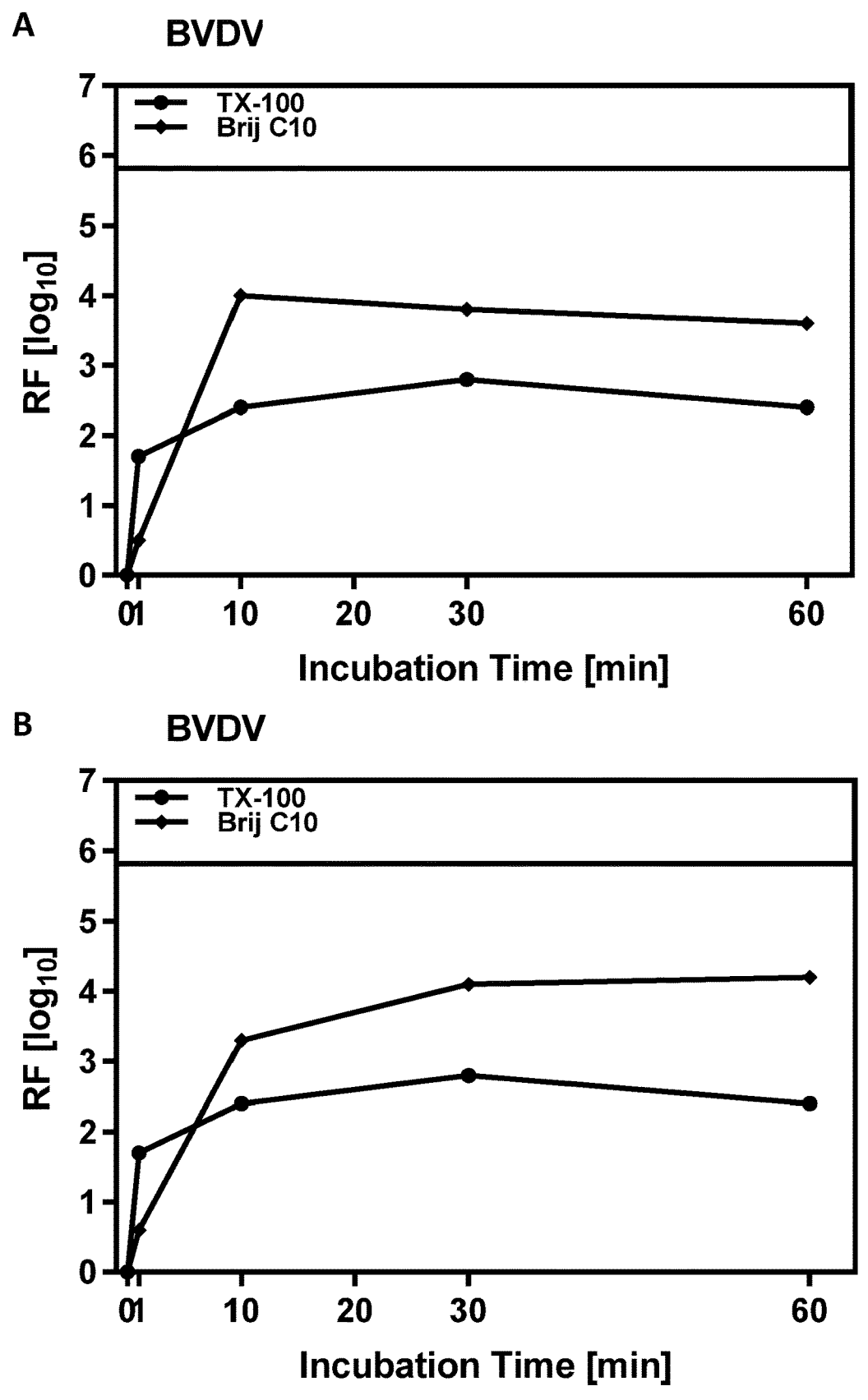

FIG. 7: Virus inactivation efficiency of low concentrations of Brij C10 in S/D treatment of HSA-containing liquid at 1° C.±1° C. A three-component mixture was used to give final concentrations of 0.08%-0.1% Brij C10, 0.02%-0.03% Polysorbate 80, 0.02%-0.03% TnBP (comparison with existing data for Triton X-100). Virus inactivation over time is indicated by the virus reduction factor (RF) for two runs with BVDV (A and B, respectively). Virus inactivation of S/D treatment using Brij C10 was compared to virus inactivation of S/D treatment using Triton X-100 ("TX-100").

Figure 8:
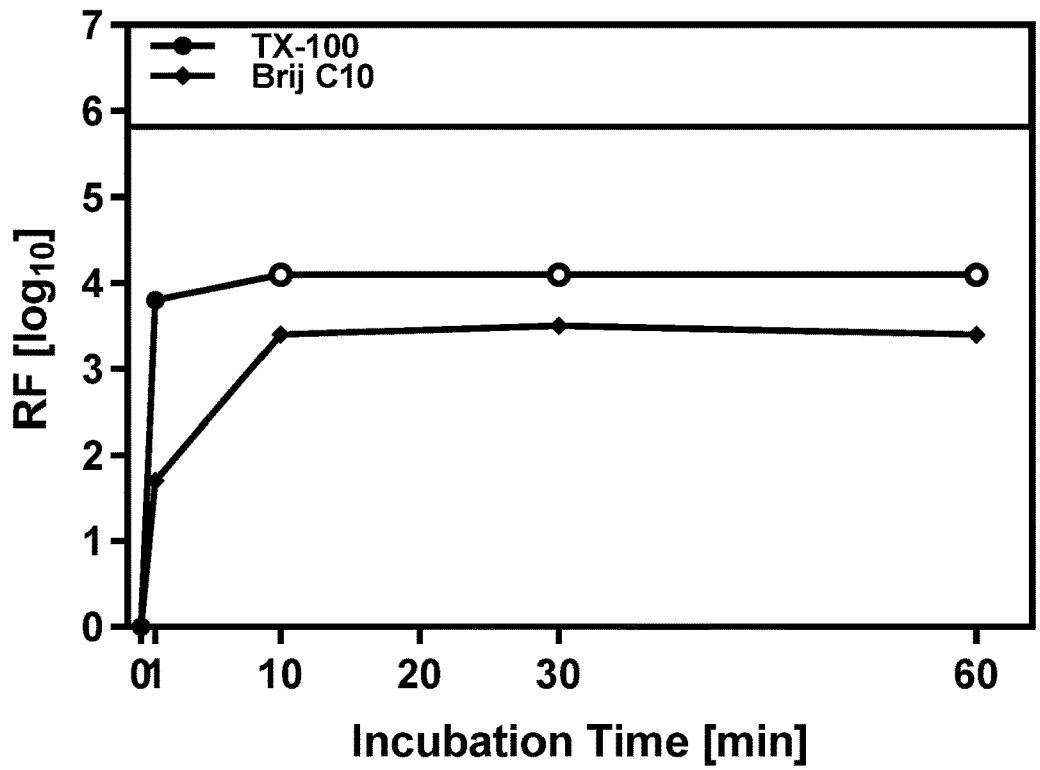
Figure 8:
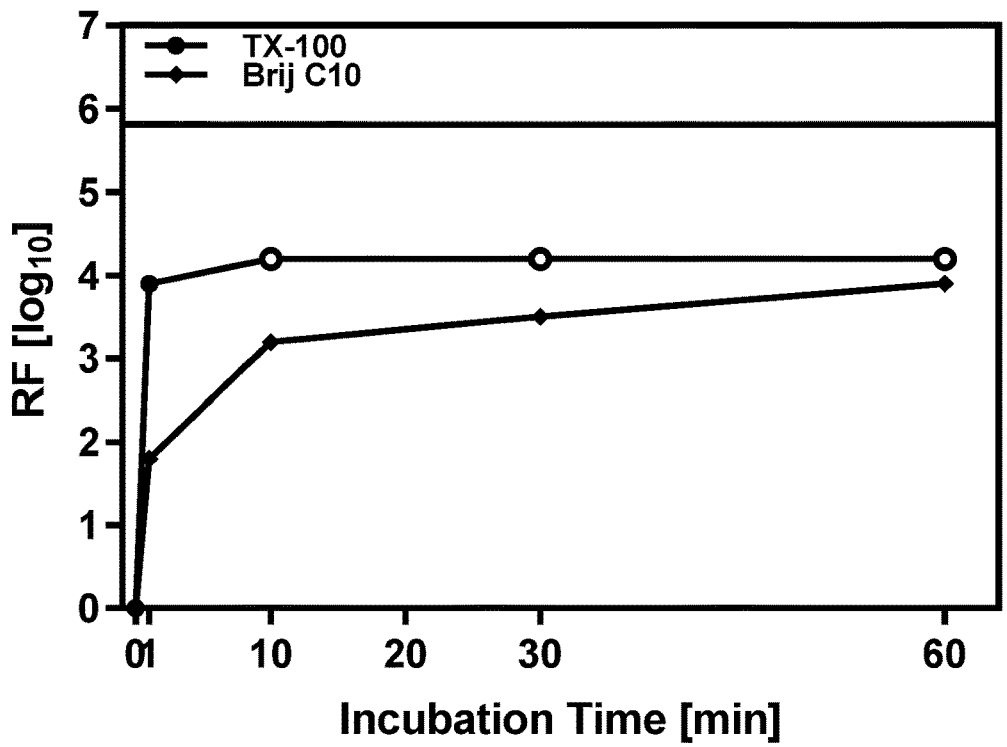

FIG. 8: Virus inactivation efficiency of low concentrations of Brij C10 in S/D treatment of HSA-containing liquid at 19° C.±1° C. A three-component mixture was used to give final concentrations of 0.08%-0.1% Brij C10, 0.02%-0.03% Polysorbate 80, 0.02%-0.03% TnBP (side-by-side comparison with same concentration of Triton X-100). Virus inactivation over time is indicated by the virus reduction factor (RF) for two runs with X-MuLV (A and B, respectively). Virus inactivation of S/D treatment using Brij C10 was compared to virus inactivation of S/D treatment using Triton X-100 ("TX-100").

Figure 9:
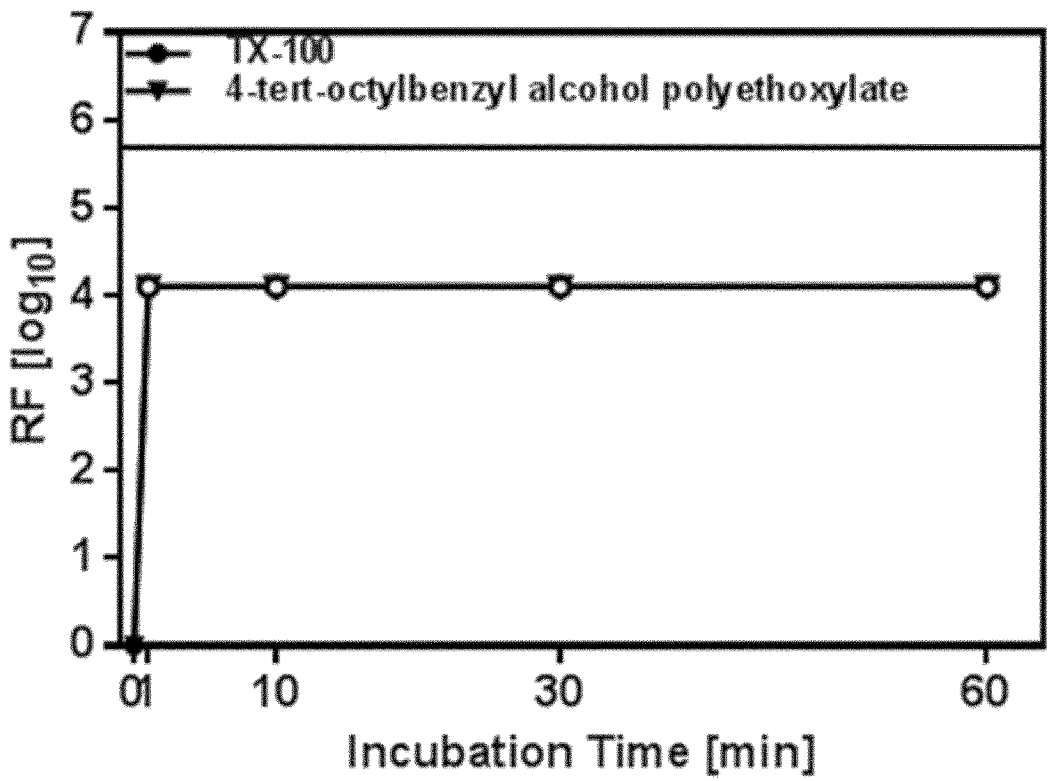
Figure 9:
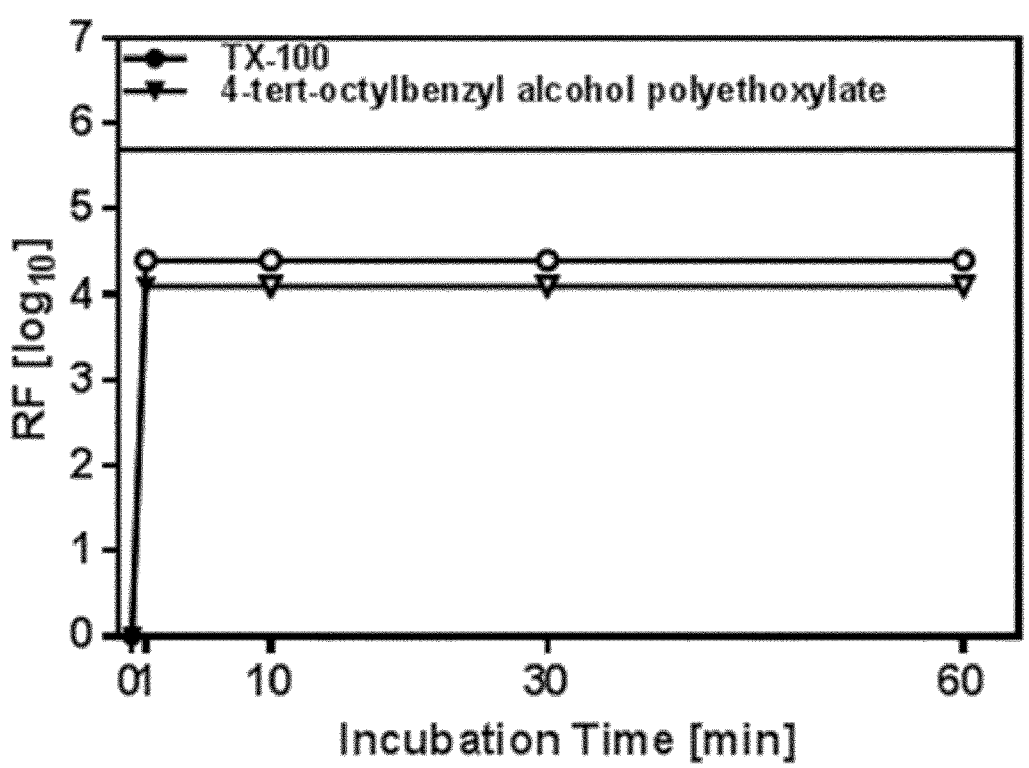

FIG. 9: Virus inactivation efficiency of low concentrations of 4-tert-octylbenzyl alcohol polyethoxylate in S/D treatment of IVIG-containing liquid at 17° C.±1° C. A three-component mixture was used to give final concentrations of 0.04%-0.06% 4-tert-octylbenzyl alcohol polyethoxylate, 0.01%-0.02% Polysorbate 80, 0.01%-0.02% TnBP (side-by-side comparison with same concentration of Triton X-100). Virus inactivation over time is indicated by the virus reduction factor (RF) for two runs with PRV (A and B, respectively). Virus inactivation of S/D treatment using 4-tert-octylbenzyl alcohol polyethoxylate was compared to virus inactivation of S/D treatment using Triton X-100 ("TX-100"). Note that in (A), both detergents show identical inactivation kinetics. Filled symbols show values with remaining infectivity, non-filled symbols show reduction factors below the limit of detection.

Figure 10:
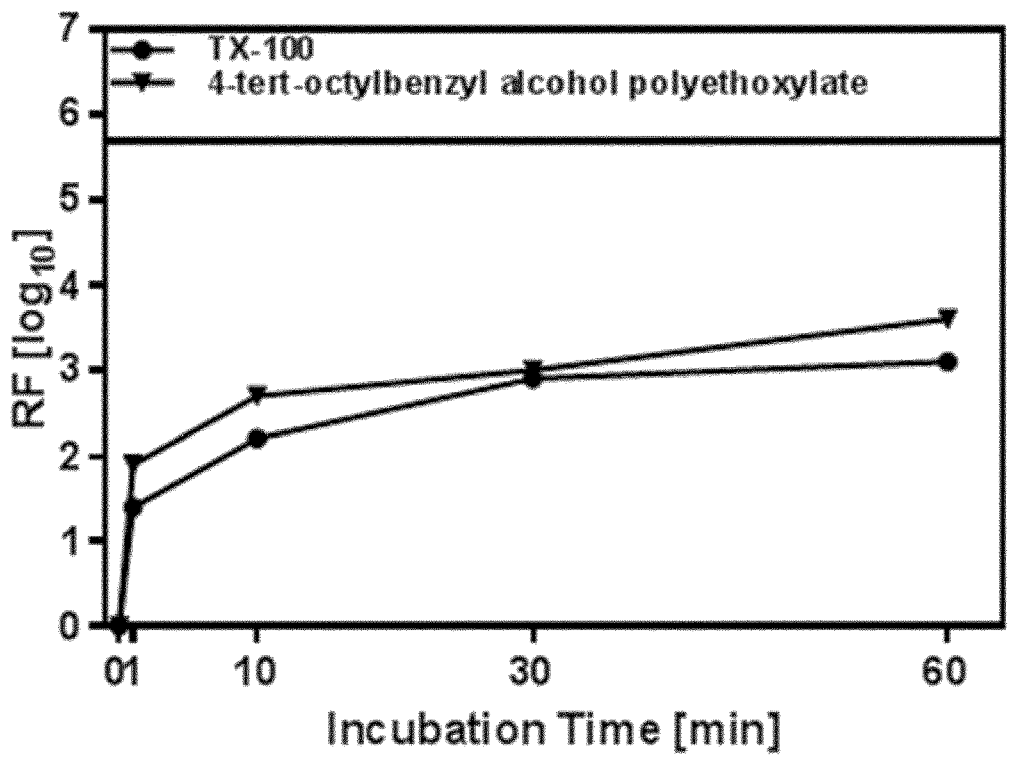
Figure 10:
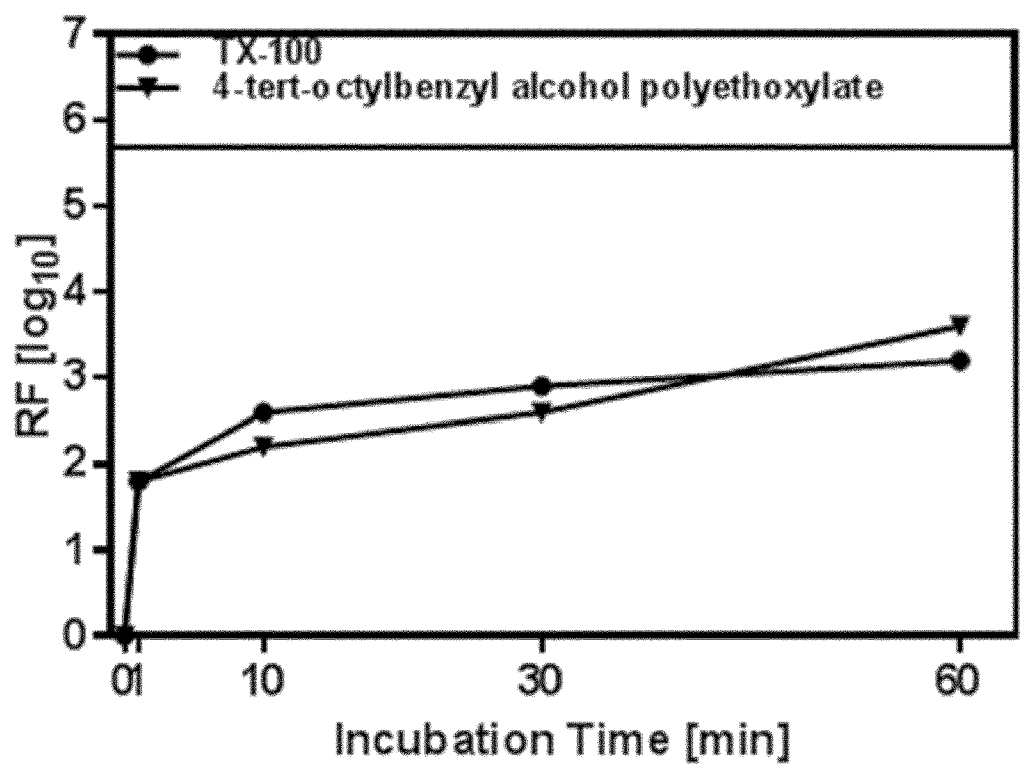

FIG. 10: Virus inactivation efficiency of low concentrations of 4-tert-octylbenzyl alcohol polyethoxylate in S/D treatment of human serum albumin (HSA)-containing liquid at 1° C.±1° C. A three-component mixture was used to give final concentrations of 0.08%-0.1% 4-tert-octylbenzyl alcohol polyethoxylate, 0.02%-0.03% Polysorbate 80, 0.02%-0.03% TnBP (side-by-side comparison with same concentration of Triton X-100). Virus inactivation over time is indicated by the virus reduction factor (RF) for two runs with X-MuLV (A and B, respectively). Virus inactivation of S/D treatment using 4-tert-octylbenzyl alcohol polyethoxylate was compared to virus inactivation of S/D treatment using Triton X-100 ("TX-100"). Filled symbols show values with remaining infectivity, non-filled symbols show reduction factors below the limit of detection.

Figure 11:
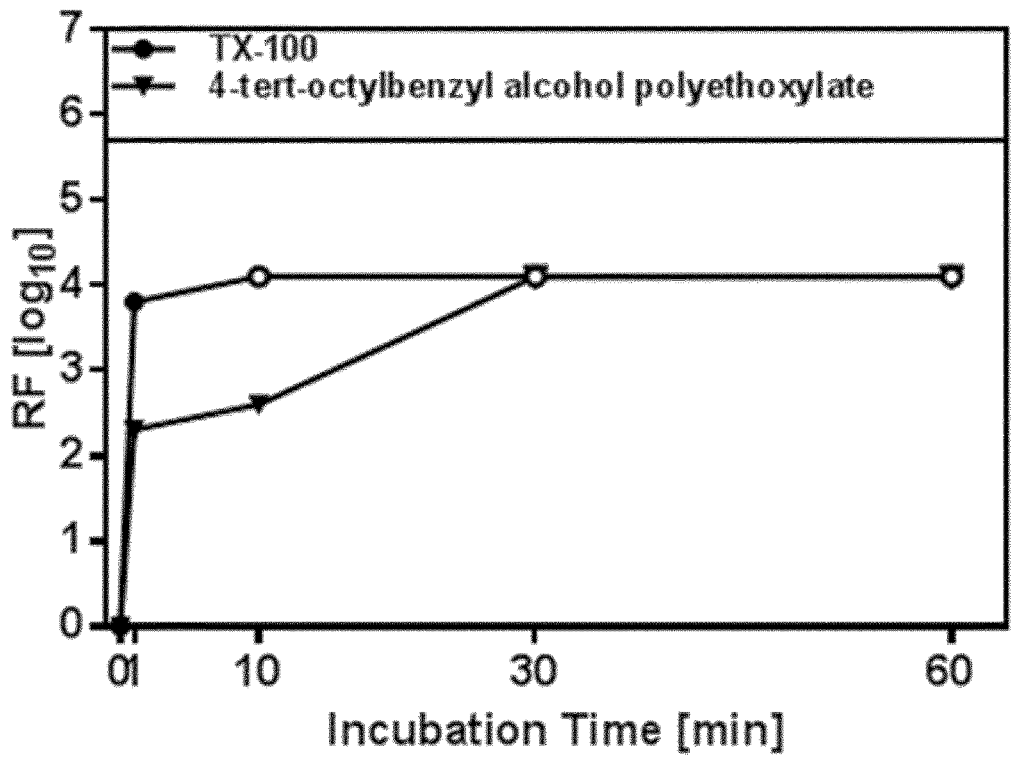
Figure 11:
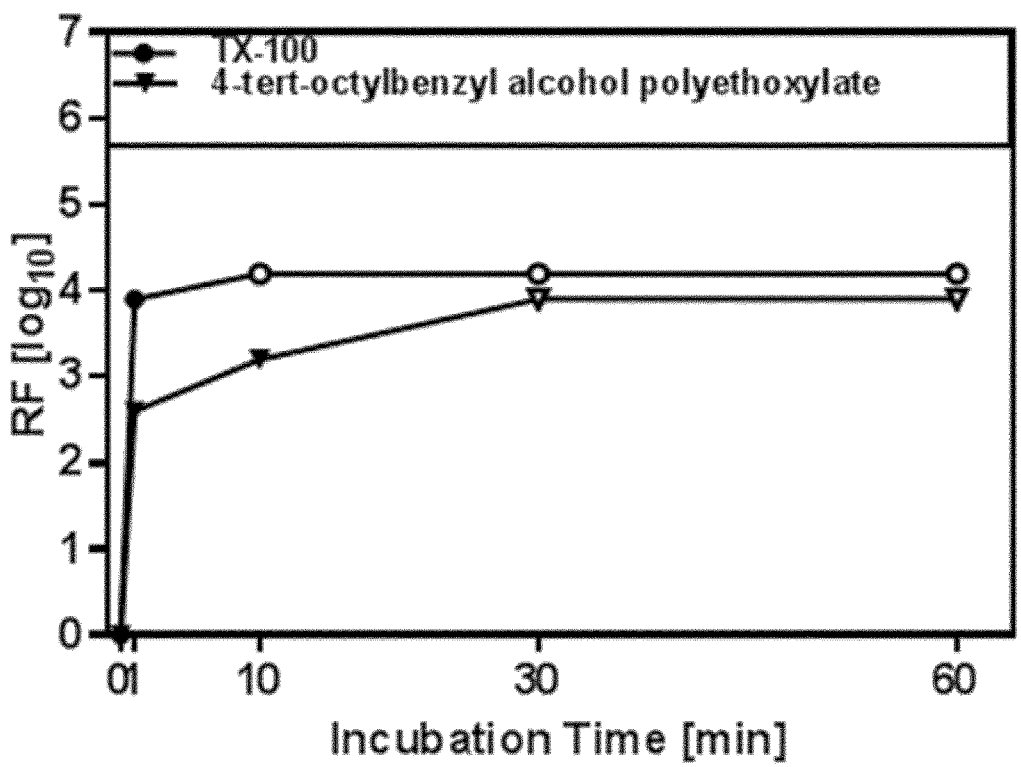

FIG. 11: Virus inactivation efficiency of low concentrations of 4-tert-octylbenzyl alcohol polyethoxylate in S/D treatment of HSA-containing liquid at 19° C.±1° C. A three-component mixture was used to give final concentrations of 0.08%-0.1% 4-tert-octylbenzyl alcohol polyethoxylate, 0.02%-0.03% Polysorbate 80, 0.02%-0.03% TnBP (side-by-side comparison with same concentration of Triton X-100). Virus inactivation over time is indicated by the virus reduction factor (RF) for two runs with X-MuLV (A and B, respectively). Virus inactivation of S/D treatment using 4-tert-octylbenzyl alcohol polyethoxylate was compared to virus inactivation of S/D treatment using Triton X-100 ("TX-100"). Filled symbols show values with remaining infectivity, non-filled symbols show reduction factors below the limit of detection.

Figure 12:
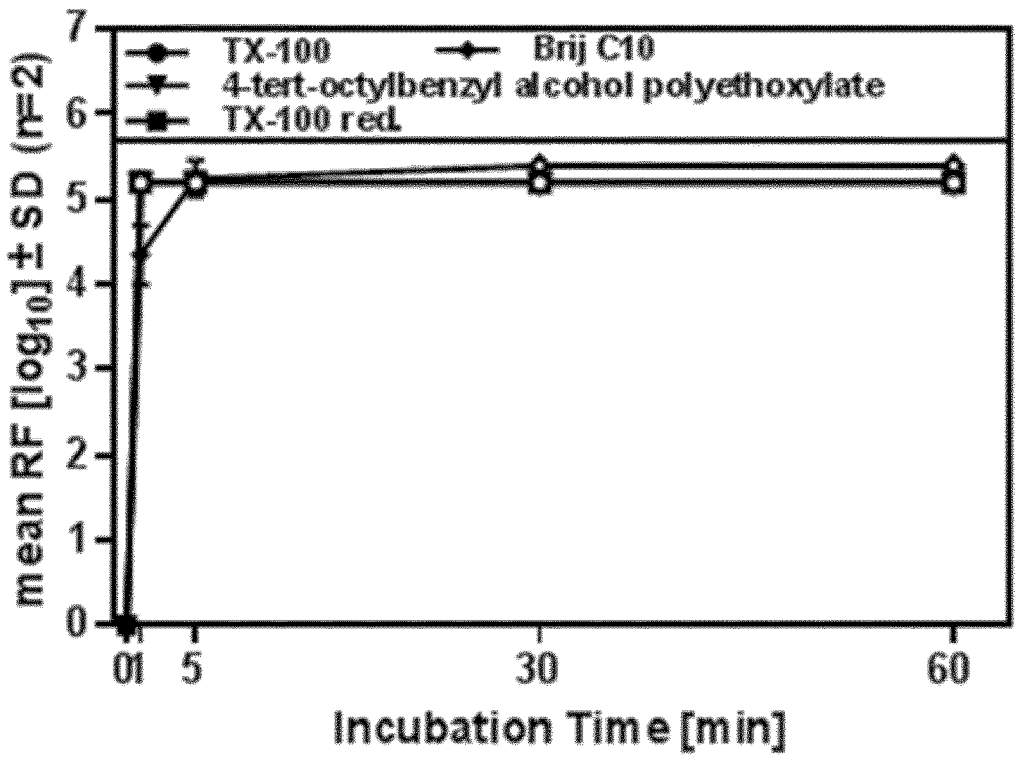
Figure 12:
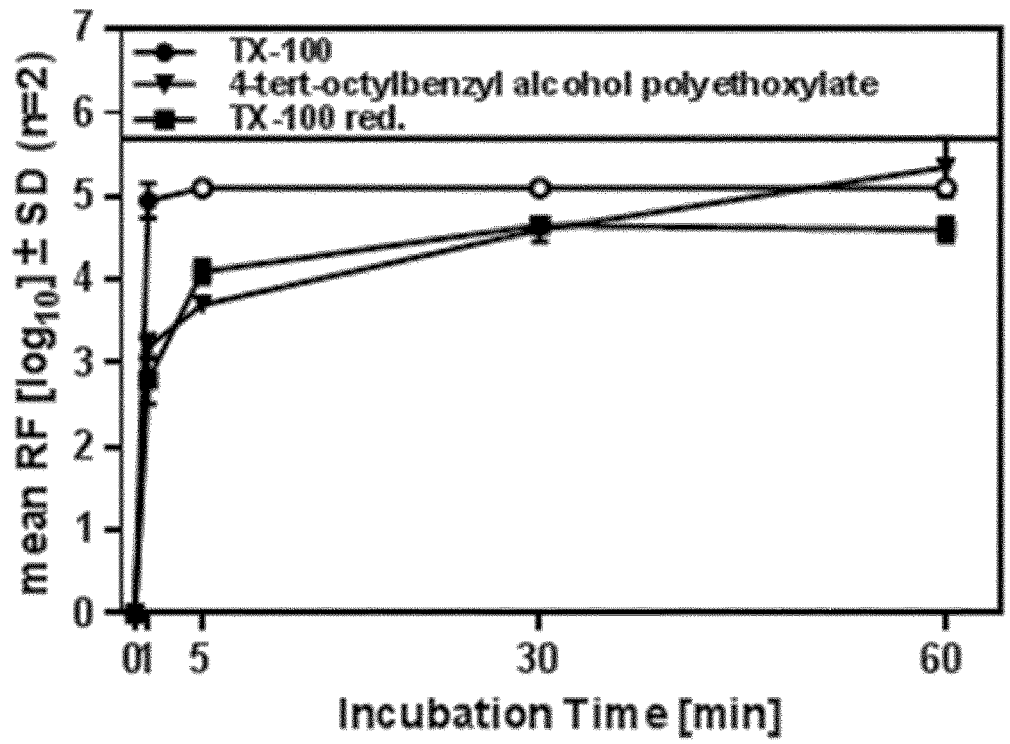

FIG. 12: (A) Virus inactivation efficiency of low concentrations of 4-tert-octylbenzyl alcohol polyethoxylate or Triton X-100 reduced or Brij C10 in detergent treatment of buffer containing HSA at 14° C.±1° C. A single-detergent treatment was used to give final concentrations of 0.09%-0.11% 4-tert-octylbenzyl alcohol polyethoxylate or Triton X-100 reduced or Brij C10 (side-by-side comparison with same concentration of Triton X-100). Virus inactivation over time is indicated by the mean virus reduction factor (RF) for two runs with BVDV. Virus inactivation of single-detergent treatment using 4-tert-octylbenzyl alcohol polyethoxylate or Triton X-100 reduced ("TX-100 red.") or Brij C10 was compared to virus inactivation of single-detergent treatment using Triton X-100 ("TX-100"). Note that 4-tert-octylbenzyl alcohol polyethoxylate and Triton X-100 reduced have the same inactivation kinetics as Triton X-100. Filled symbols show values with remaining infectivity, non-filled symbols show reduction factors below the limit of detection. (B) Virus inactivation efficiency of low concentrations of 4-tert-octylbenzyl alcohol polyethoxylate or Triton X-100 reduced in detergent treatment of buffer containing HSA at 14° C.±1° C. A single-detergent treatment was used to give final concentrations of 0.02%-0.04% 4-tert-octylbenzyl alcohol polyethoxylate or Triton X-100 reduced (side-by-side comparison with same concentration of Triton X-100). Virus inactivation over time is indicated by the mean virus reduction factor (RF) for two runs with BVDV. Virus inactivation of single-detergent treatment using 4-tert-octylbenzyl alcohol polyethoxylate or Triton X-100 reduced ("TX-100 red.") was compared to virus inactivation of single-detergent treatment using Triton X-100 ("TX-100"). Filled symbols show values with remaining infectivity, non-filled symbols show reduction factors below the limit of detection.

Figure 13:
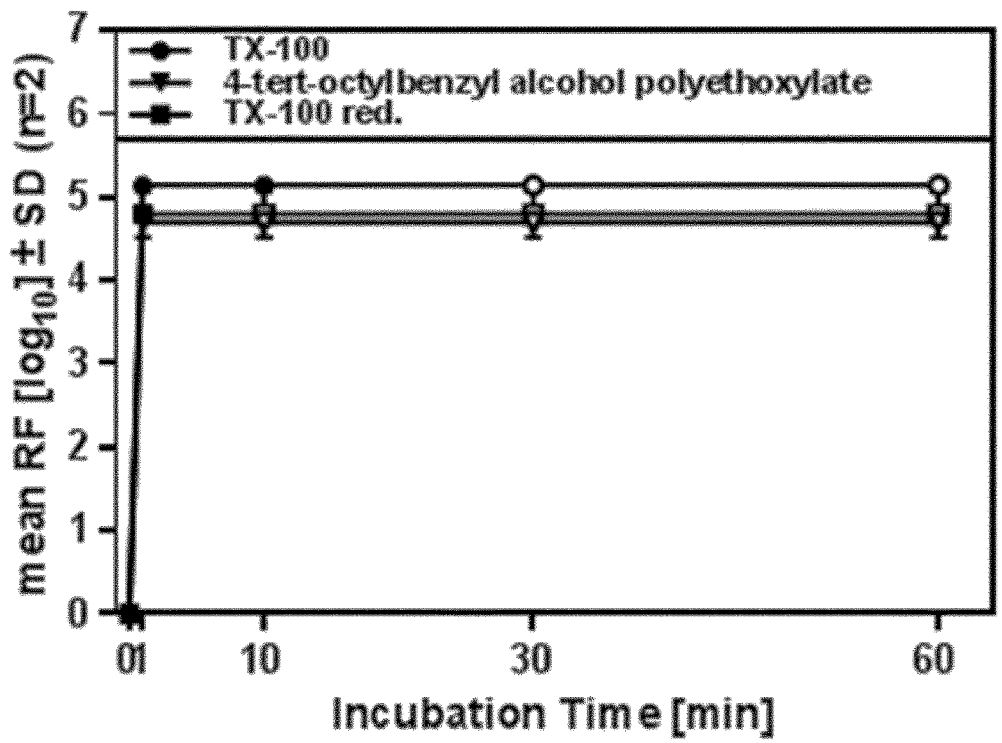
Figure 13:
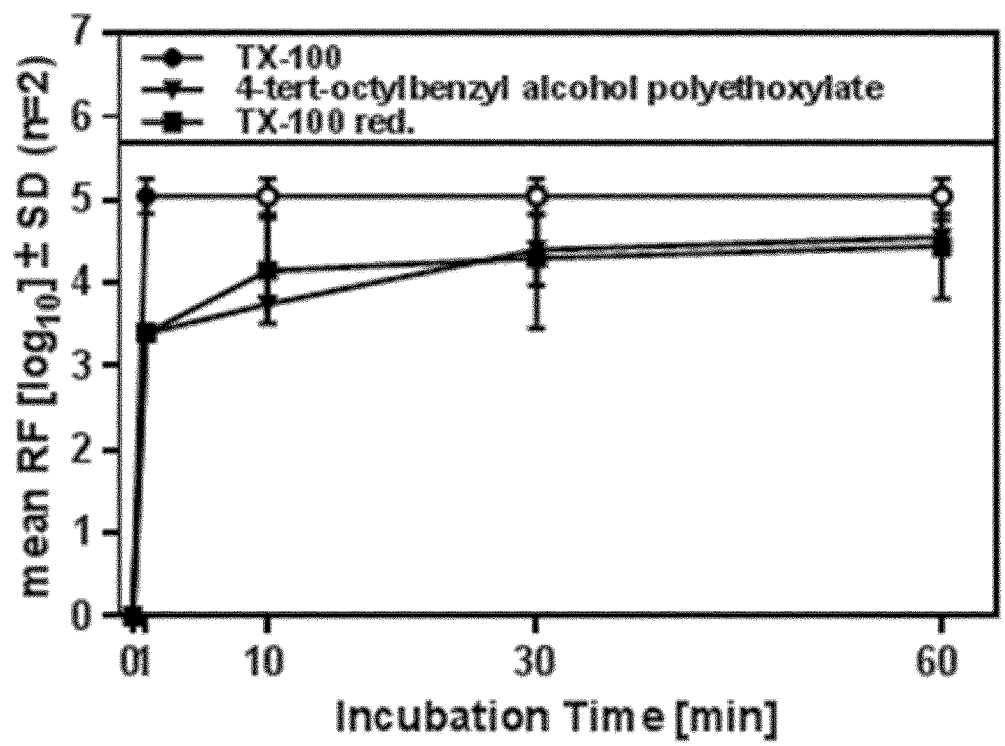

FIG. 13: (A) Virus inactivation efficiency of low concentrations of 4-tert-octylbenzyl alcohol polyethoxylate or Triton X-100 reduced in detergent treatment of IVIG-containing liquid at 17° C.±1° C. A single-detergent treatment was used to give final concentrations of 0.09%-0.11% 4-tert-octylbenzyl alcohol polyethoxylate or Triton X-100 reduced (side-by-side comparison with same concentration of Triton X-100). Virus inactivation over time is indicated by the mean virus reduction factor (RF) for two runs with BVDV. Virus inactivation of single-detergent treatment using 4-tert-octylbenzyl alcohol polyethoxylate or Triton X-100 reduced ("TX-100 red.") was compared to virus inactivation of single-detergent treatment using Triton X-100 ("TX-100"). Filled symbols show values with remaining infectivity, non-filled symbols show reduction factors below the limit of detection. (B) Virus inactivation efficiency of low concentrations of 4-tert-octylbenzyl alcohol polyethoxylate or Triton X-100 reduced in detergent treatment of IVIG-containing liquid at 17° C.±1° C. A single-detergent treatment was used to give final concentrations of 0.02%-0.04% 4-tert-octylbenzyl alcohol polyethoxylate or Triton X-100 reduced (side-by-side comparison with same concentration of Triton X-100). Virus inactivation over time is indicated by the mean virus reduction factor (RF) for two runs with BVDV. Virus inactivation of single-detergent treatment using 4-tert-octylbenzyl alcohol polyethoxylate or Triton X-100 reduced ("TX-100 red.") was compared to virus inactivation of single-detergent treatment using Triton X-100 ("TX-100"). Filled symbols show values with remaining infectivity, non-filled symbols show reduction factors below the limit of detection.

Figure 14:
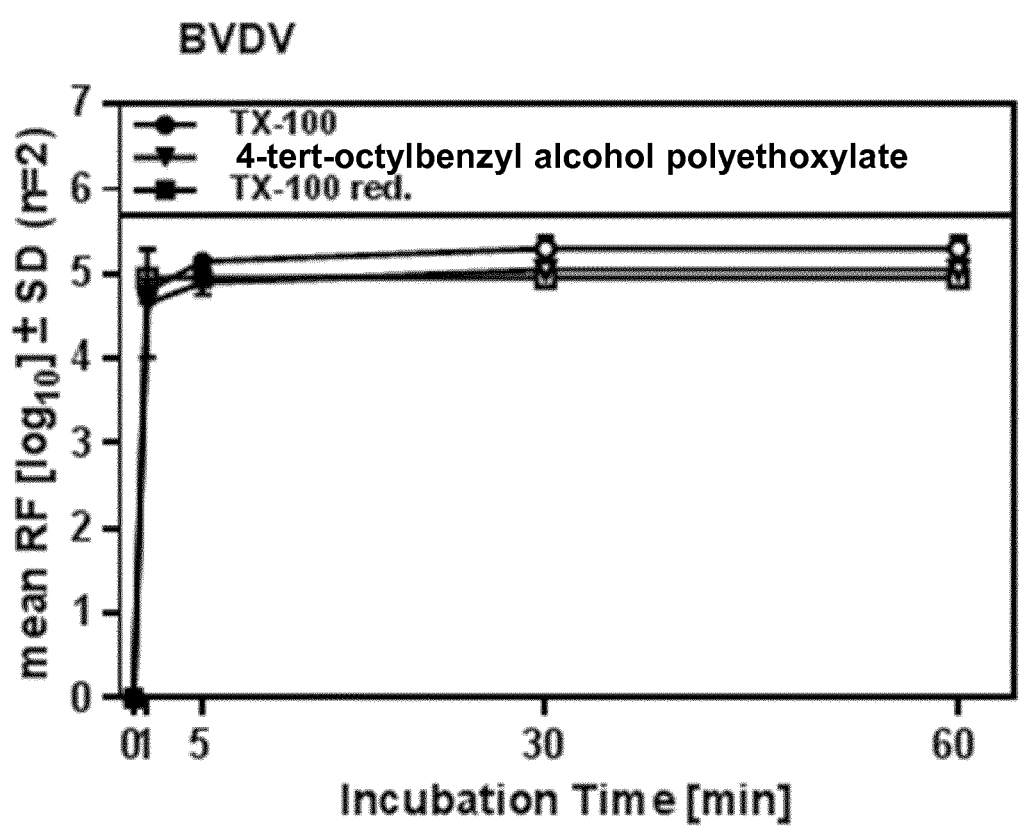

FIG. 14: Virus inactivation efficiency of low concentrations of 4-tert-octylbenzyl alcohol polyethoxylate or Triton X-100 reduced in detergent treatment of Factor VIII-containing liquid at 23° C.±1° C. A single-detergent treatment was used to give final concentrations of 0.09%-0.11% 4-tert-octylbenzyl alcohol polyethoxylate or Triton X-100 reduced (side-by-side comparison with same concentration of Triton X-100). Virus inactivation over time is indicated by the mean virus reduction factor (RF) for two runs with BVDV. Virus inactivation of single-detergent treatment using 4-tert-octylbenzyl alcohol polyethoxylate or Triton X-100 reduced ("TX-100 red.") was compared to virus inactivation of single-detergent treatment using Triton X-100 ("TX-100"). Filled symbols show values with remaining infectivity, non-filled symbols show reduction factors below the limit of detection.

DETAILED DESCRIPTION OF THE INVENTION

Unless otherwise defined below, the terms used in the present invention shall be understood in accordance with their common meaning known to the person skilled in the art.

All publications, patents and patent applications cited herein are hereby incorporated by reference in their entirety for all purposes.

Definitions

The terms "virus having a lipid envelope", "lipid-enveloped virus" and "enveloped virus" are used interchangeably herein, and have the meaning known to a person skilled in the art. For example, lipid-enveloped viruses can be Herpesviridae such as pseudorabies virus (PRV), herpes simplex virus, varicella-zoster virus, cytomegalovirus or Epstein-Barr virus; Hepadnaviridae such as hepatitis B virus; Togaviridae such as sindbis virus, rubella virus or alphavirus; Arenaviridae such as Imphocytic choriomeningitis virus; Flaviviridae such as West Nile virus, bovine viral diarrhea virus (BVDV), dengue virus, hepatitis C virus or yellow fever virus; Orthomyxoviridae such as influenza virus A, influenza virus B, influenza virus C, isavirus or thogotovirus; Paramyxoviridae such as sendai virus, measles virus, mumps virus, respiratory syncytial virus, Rinderpest virus or canine distemper virus; Bunyaviridae such as California encephalitis virus or hantavirus; Rhabdoviridae such as vesicular stomatitis virus or rabies virus; Filoviridae such as Ebola virus or Marburg virus; Coronaviridae such as corona virus or severe acute respiratory syndrome (SARS) coronavirus; Bornaviridae such as Borna disease virus; or Arteriviridae such as arterivirus or equine arteritis virus; Retroviridae such as Human Immunodeficiency Virus (HIV), Human T-lymphotropic virus 1 (HTLV-1) or xenotropic murine leukemia virus (X-MuLV); Poxviridae such as vaccinia virus or Orthopoxvirus variolae (Variolavirus).

The term "inactivating a virus having a lipid envelope" as used herein refers to disrupting the ability of the lipid-enveloped virus to infect cells. As will be understood by a person skilled in the art, the ability of a lipid-enveloped virus to infect cells, i.e. the infectivity of a lipid-enveloped virus, is typically assessed by determining the number of infectious virus particles in a liquid. Hence, the term "inactivating a virus having a lipid envelope" or "inactivating a lipid-enveloped virus" as used herein refers to reducing the number of infectious virus particles in a solution.

Herein the term "Log 10 reduction value" or "LRV" is used interchangeably with the term "virus reduction factor", "reduction factor", "RF" or "R". In one embodiment, the "Log 10 reduction value" or "LRV" can be used as a measure of the reduction of infectious virus particles in a liquid. As used herein, the "Log 10 reduction value" or "LRV" is defined as the logarithm (base 10) of the ratio of infectious virus particles before virus inactivation to infectious virus particles after virus inactivation. The LRV value is specific to a given type of virus. It is evident for a skilled person in the art that any Log 10 reduction value (LRV) above zero is beneficial for improving the safety of methods and processes such as biopharmaceutical production methods and processes. The Log 10 reduction value (LRV) that is achieved by the methods according to the present invention is determined as known to a person skilled in the art. For example, the LRV can be determined by determining the number of infectious virus particles in a liquid before and after subjecting the liquid to the method for virus inactivation according to the present invention.

The skilled person will be aware of numerous methods to measure infectious virus particles in a liquid. For example, and without limitation, infectious virus particle concentrations in a liquid can preferably be measured by plaque assay or by the $TCID_{50}$ assay, more preferably by the $TCID_{50}$ assay. A "$TCID_{50}$ assay" as used herein refers to a tissue culture infectious dose assay. The $TCID_{50}$ assay is an endpoint dilution test, wherein the $TCID_{50}$ value represents the viral concentration necessary to induce cell death or pathological changes in 50% of cell cultures inoculated.

The term "surfactant" as used herein refers to compounds that lower the surface tension between two liquids or between a liquid and a solid. Surfactants may act as detergents, wetting agents, emulsifiers, foaming agents, and dispersants.

In connection with the invention, terms such as "adding to", "add to" or "added to" in connection with a first- and second-mentioned solvent, detergent and/or liquid encompass a situation where the first-mentioned solvent, detergent and/or liquid is added to the second-mentioned solvent, detergent and/or liquid. However, these terms are also meant to encompass a situation where the second-mentioned solvent, detergent and/or liquid is added to the first-mentioned solvent, detergent and/or liquid. Thus, terms such as "adding to", "add to" or "added to" are not meant to specify whether the first-mentioned solvent, detergent and/or liquid is to be added to the second-mentioned solvent, detergent and/or liquid, or vice versa.

As will be known to a person skilled in the art, the term "detergent" is used according to its general meaning known in the art and includes in particular surfactants that can permeabilize lipid membranes. For example, the detergents Triton X-100 and deoxycholate have been suggested to solubilize amphipathic membrane proteins by binding to the hydrophobic segments of proteins (see Simons et al., 1973). Detergents are classified into three broad groups, depending on their electrical charge. Anionic detergents comprise an anionic, i.e. a negatively charged, hydrophilic group. Exemplary anionic detergents are tetradecyltrimethylammonium bromide, dodecyltrimethylammonium bromide, sodium laureth sulphate, sodium dodecyl sulphate (SDS), cetrimide and hexadecyltrimethylammonium bromide. Cationic detergents comprise a cationic, i.e. a positively charged, hydrophilic group. Exemplary cationic detergents are benzalkonium chloride, cetyl trimethlammonium bromide (CTAB), cetylpyridinium chloride (CPC) and benzethonium chloride (BZT). The term "non-ionic detergents" as used herein refers to detergents having no positive or negative charge. Exemplary non-ionic detergents are sorbitan esters (sorbitan monolaurate, sorbitan monopalmitate, sorbitan monostearate, sorbitan tristearate, sorbitan monooleate, Sorbitan trioleate), polysorbates (polyoxyethylene (20) sorbitan monolaurate (Polysorbate 20), polyoxyethylene (20) sorbitan monopalmitate, polyoxyethylene (20) Sorbitan monostearate, polyoxyethylene (20) sorbitan tristearate, polyoxyethylene (20) Sorbitan trioleate, Polyoxyethylen(20)-sorbitan-monooleate (Tween 80/Polysorbate 80)), poloxamers (poloxamer 407, poloxamer 188) and cremophor. Detergents in accordance with the invention are as specified in the preferred embodiments and include, without limitation, Triton N-101 reduced, Triton X-100 reduced and Brij C10.

The term "non-phenolic" as used herein is interchangeably used with the term "phenol-free". A non-phenolic detergent as used in the present invention refers to a detergent that does not contain any phenol functional groups. The term "aromatic" has the meaning known to a person skilled in the art. A detergent that is not aromatic as used in the present invention refers to a detergent that does not contain any aromatic rings.

The term "environmentally compatible" as used herein has the meaning known to a person skilled in the art. In a preferred embodiment of the invention, with regard to detergents, the term "environmentally compatible" indicates that the detergent does not behave as an endocrine disrupter. Endocrine disruptors are exogenous substances that alter function(s) of the endocrine system and consequently cause adverse health effects in an intact organism or its progeny, or (sub)populations. The skilled person will be aware of various methods to identify endocrine disruptors. Further information on endocrine disruptors and their evaluation can be found, e.g., in the "ECHA Support document for identification of 4-(1,1,3,3-tetramethylbutyl)phenol, ethoxylated as substances of very high concern because, due to their degradation to a substance of very high concern (4-(1,1,3,3-tetramethylbutyl)phenol) with endocrine disrupting properties, they cause probable serious effects to the environment which give rise to an equivalent level of concern to those of CMRs and PBTs/vPvBs", adopted on 12 Dec. 2012, which is hereby incorporated in its entirety and for all purposes; or in the brochure "Global Assessment of the Sate-of-the-Science of Endocrine Disruptors" (WHO/PCS/EDC/02.2), which is hereby incorporated in its entirety and for all purposes, published by the International Programme on Chemical Safety of the World Health Organisation.

The term "solvent" as used herein has the meaning known to a person skilled in the art. In a preferred embodiment of the invention, organic solvents are used in the methods of the present invention. Particularly useful organic solvents create an environment promoting contact between a detergent and the lipoprotein envelope of a lipid-enveloped virus. As such, an organic solvent that promotes such contact is preferably used in the methods of the present invention, including, without limitation, an ether, an alcohol, an alkylphosphate like a dialkylphosphate or a trialkylphosphate, or any combination thereof.

Ether solvents useful in the methods disclosed herein include those having the formula R1-O-R2, wherein, R1 and R2 are independently C1-C18 alkyl or C1-C18 alkenyl which can contain an oxygen or sulfur atom, preferably C1-C18 alkyl or C1-C18 alkenyl. Non-limiting examples of ethers include dimethyl ether, diethyl ether, ethyl propyl ether, methyl-butyl ether, methyl isopropyl ether and methyl isobutyl ether. Alcohol solvents useful in the method disclosed herein include those having C1-C8 alkyl groups or C1-C8 alkenyl groups. Non-limiting examples of alcohols include methanol, ethanol, propanol, isopropanol, n-butanol, isobutanol, n-pentanol and the isopentanols. Alkylphosphate solvents useful in the method disclosed herein include those having C1-C18 alkyl groups or C1-C18 alkenyl groups, either of which may contain an oxygen or sulfur atom. Non-limiting examples of alkylphosphates include dialkylphosphates like di-(n-butyl)phosphate, di-(t-butyl)phosphate, di-(n-hexyl)phosphate, di-(2-ethylhexyl)phosphate, di-(n-decyl)phosphate, or ethyl di(n-butyl) phosphate; and trialkylphosphates like tri-(n-butyl)phosphate, tri-(t-butyl) phosphate, tri-(n-hexyl)phosphate, tri-(2-ethylhexyl)phosphate, or tri-(n-decyl)phosphate.

The term "biological medicinal product" as used herein is known in the art and refers to a product, the active substance of which is a biological substance, e.g. a biological substance which is produced by mammalian cells or microorganisms. As used herein, the biological medicinal product used in the methods of the invention is not limited to the final manufactured product but preferably also includes intermediate products at any stage of the manufacturing process.

The term "biopharmaceutical drug" as used herein has the meaning known to a person skilled in the art. Biopharmaceutical drugs include both recombinant biopharmaceutical drugs and biopharmaceutical drugs from other sources such as biopharmaceutical drugs obtained from human plasma.

As used herein the term "depth filter" has the meaning known in the art. In particular, such a filter (e.g., gradient-density depth filter) achieves filtration within the depth of the filter material. A common class of such filters is those that comprise a random matrix of fibers bonded (or otherwise fixed), to form a complex, tortuous maze of flow channels. Particle separation in these filters generally results from entrapment by or adsorption to, the fiber matrix. The most frequently used depth filter media for bioprocessing of cell culture broths and other feedstocks are cellulose fibers, a filter aid such as DE, and a positively charged resin binder. Depth filter media, unlike absolute filters, retain particles throughout the porous media allowing for retention of particles both larger and smaller than the pore size. Particle retention is thought to involve both size exclusion and adsorption through hydrophobic, ionic and other interactions.

The term "purifying a biopharmaceutical drug" as used herein has the meaning known to a person skilled in the art, and refers to separating the biopharmaceutical drug from other substances that may be comprised in the mixture of the present invention. In a preferred embodiment of the invention, the term "purifying a biopharmaceutical drug" refers to separating the biopharmaceutical drug from the detergent of the present invention.

The term "chromatography" is used according to its meaning known in the art. It includes any chromatography technique which separates an analyte of interest (e.g. a target molecule such as a biopharmaceutical drug) from other molecules present in a mixture. Usually, the analyte of interest is separated from other molecules as a result of differences in rates at which the individual molecules of the mixture migrate through a stationary medium under the influence of a moving phase, or in bind and elute processes.

The terms "chromatography resin" and "chromatography media" are used interchangeably herein and refer to any kind of phase (e.g., a solid phase) which separates an analyte of interest (e.g., a target molecule such as a biopharmaceutical drug) from other molecules present in a mixture. Usually, the analyte of interest is separated from other molecules as a result of differences in rates at which the individual molecules of the mixture migrate through a stationary solid phase under the influence of a moving phase, or in bind and elute processes. Examples of various types of chromatography media include, for example, cation exchange resins, cation exchange membranes, affinity resins, anion exchange resins, anion exchange membranes, hydrophobic interaction resins and ion exchange monoliths.

The term "pharmaceutical formulation" as used herein has the meaning known to a person skilled in the art and refers to any formulation that is suitable for administration to a patient. Pharmaceutical formulations can be prepared according to methods known in the art. For example, for any biopharmaceutical drug that is present in the formulation, a skilled person will be able to choose and add preferred additional ingredients including buffers, stabilizers, surfactants, anti-oxidants, chelating agents and/or preservatives etc.

The term "solvent/detergent mixture" as used herein has the meaning known to the person skilled in the art. In a preferred embodiment, the solvent/detergent mixture used in accordance with the invention contains at least one solvent other than water and at least one detergent. The solvent used in accordance with the invention is preferably an organic solvent, and is most preferably tri-n-butyl phosphate. The number of different solvents and/or detergents contained in the mixture is not particularly limited. For example, the solvent/detergent mixture can be composed of tri-n-butyl phosphate, Polysorbate 80 and a polyoxyethylene ether detergent according to the present invention.

It is to be understood that the term "between" when used to indicate a numerical range in the present invention includes the indicated lower and upper limits of the respective range. For example, when a temperature is indicated to be between 0° C. and 10° C., this includes the temperatures of 0° C. and 10° C. Similarly, when a variable x is indicated to be an integer between, e.g., 4 and 16, this includes the integers 4 and 16.

It is to be understood that the term "1 hour" as used herein is not limited to exactly 60 minutes. As used herein, the term "1 hour" is to be understood to relate to 60 minutes±5 minutes, preferably 60 minutes±2 minutes.

Embodiments

The method for inactivating a virus having a lipid envelope according to the present invention comprises the step of adding a detergent to a liquid to prepare a mixture of said detergent and said liquid and a step of incubating said mixture to inactivate said virus. As described above, the term "inactivating a virus having a lipid envelope" as used herein refers reducing the concentration of infectious virus particles in a solution. In the method for inactivating a virus having a lipid envelope according to the present invention, it is preferable that the method achieves at least a 1 Log 10 reduction value (LRV) for at least one virus, or at least a 2 Log 10 reduction value (LRV) for at least one virus, or at least a 3 Log 10 reduction value (LRV) for at least one virus, or at least a 4 Log 10 reduction value (LRV) for at least one virus, or at least a 5 Log 10 reduction value (LRV) for at least one virus, or at least a 6 Log 10 reduction value (LRV) for at least one virus, or at least a 7 Log 10 reduction value (LRV) for at least one virus, or at least a 8 Log 10 reduction value (LRV) for at least one virus, most preferably at least a 4 Log 10 reduction value (LRV) for at least one virus. Of course, it is evident for a skilled person in the art that any Log 10 reduction value (LRV) for at least one virus is beneficial, because it improves the safety of e.g. the biopharmaceutical production process. The LRVs referred to in accordance with the invention are LRVs of an enveloped virus.

It is to be understood that although the methods of the present invention are generally for inactivating lipid-enveloped viruses, the detergents in accordance with the present invention may also inactivate non-enveloped viruses, for example if such non-enveloped viruses acquire a lipid envelope at some stage during their replication cycle. Thus, the term "inactivating a virus having a lipid envelope" is not meant to exclude the possibility that in the methods of the invention, non-enveloped viruses can also be inactivated in addition to viruses having a lipid envelope.

In the method for inactivating a virus having a lipid envelope according to the present invention a detergent is added to a liquid to prepare a mixture of said detergent and said liquid, and said mixture is incubated to inactivate said virus. It is to be understood that said liquid of the method of the present invention may be any kind of liquid or a mixture of several liquids, including a solution, a suspension, or a mixture of several suspensions and/or solutions. For example, and without limitation thereto, said liquid in accordance with the present invention may be blood or may contain blood or a blood fraction, may be plasma or may contain plasma or a plasma fraction, may be serum or may contain serum or a serum fraction, may be cell culture medium or may contain cell culture medium, may be a buffer or may contain a buffer. The liquid may also be a process intermediate, e.g. a process intermediate in the preparation of a biopharmaceutical drug.

The liquid in accordance with the present invention may contain a virus having a lipid envelope, or it may be suspected to contain a virus having a lipid envelope (e.g. in case it is blood or contains blood or a blood fraction, plasma or contains plasma or a plasma fraction, serum or contains serum or a serum fraction, or if it contains a biopharmaceutical drug produced in cell culture). In a preferred embodiment of the present invention in accordance with all other embodiments of the invention, said liquid in accordance with the present invention contains virus having a lipid envelope. The origin of said virus having a lipid envelope in said liquid in accordance with the present invention is not particularly limited. For example, the virus may originate from human blood that may be used to prepare the liquid in accordance with the present invention, or from human plasma that may be used to prepare the liquid in accordance with the present invention, or from human serum that may be used to prepare the liquid in accordance with the present invention, or from cell culture medium that may be used to prepare the liquid in accordance with the present invention. In particular, if the virus originates from cell culture medium that is used to prepare the liquid in accordance with the present invention, the virus may originate from animal-derived components of said cell culture medium, such as bovine serum albumin.

In the method for inactivating a virus having a lipid envelope according to the present invention, a detergent is added to a liquid to prepare a mixture of said detergent and said liquid. Said detergent is a polyoxyethylene ether.

Polyoxyethylene ethers are known to a person skilled in the art and have the following structure according to Formula A:

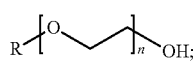

(Formula A)

wherein n is equal to or higher than one.

As will be clear to a person skilled in the art, polyoxypropylene ethers can have very similar properties as the polyoxyethylene ethers in accordance with the present invention. Thus, in accordance with all other embodiments of the invention, e.g. in the methods for inactivating a virus having a lipid envelope of the present invention, the polyoxyethylene ethers may be replaced by polyoxypropylene ethers.

Polyoxypropylene ethers are also known to a person skilled in the art and have the following structure according to Formula B:

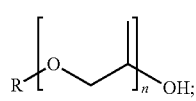

(Formula B)

wherein n is equal to or higher than one.

As referred to herein, a "polyoxyethylene ether" in accordance with the invention is preferably a polyoxyethylene ether according to its common meaning in the art. Alternatively, a polyoxyethylene ether in accordance with the invention may also be a polyoxyether, where a part of, preferably the majority of the total number of polyoxyether molecules are polyoxyethylene ether molecules, but where another part of, preferably the minority of the total number of polyoxyether molecules are mixed polymers comprising oxyethylene and oxypropylene units and/or polymers comprising oxypropylene units. In this case, the term "the majority of the total number of polyoxyether molecules are polyoxyethylene ether molecules" means that at least 50% of the total number of polyoxyether molecules are polyoxyethylene ether molecules. Preferably, at least 60% of the total number of polyoxyether molecules are polyoxyethylene ether molecules. More preferably, at least 70% of the total number of polyoxyether molecules are polyoxyethylene ether molecules. Still more preferably, at least 80% of the total number of polyoxyether molecules are polyoxyethylene ether molecules. Still more preferably, at least 90% of the total number of polyoxyether molecules are polyoxyethylene ether molecules. Most preferably, at least 95% of the total number of polyoxyether molecules are polyoxyethylene ether molecules. Yet alternatively, a polyoxyethylene ether in accordance with the invention may also be a mixed polyoxyether, comprising a majority (e.g. at least 60%, preferably at least 70%, more preferably at least 80%, still more preferably at least 90%, and most preferably at least 95%) of oxyethylene units and a minority of oxypropylene units.

The detergents for use in accordance with the methods of the present invention are non-phenolic. In another embodiment in accordance with all other embodiments of the invention, the detergents for use in in accordance with the methods of the present invention are not aromatic.

The polyoxyethylene ether detergents in accordance with the present invention can be synthetized by ethoxylation reaction. Ethoxylation is an industrial process performed upon alcohols (alternatively amines can be used) in order to generate alcohol ethoxylates (aka polyoxyethylene ethers). The reaction proceeds by passing ethylene oxide through the alcohol at high temperature (e.g., around 180° C.) and under high pressure (e.g., under 1-2 bar of pressure), with a base (such as potassium hydroxide, KOH) serving as a catalyst. The process is highly exothermic.

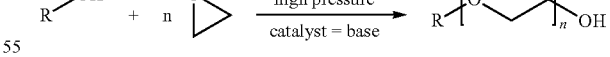

The reaction leads to the formation of a product with a wide polydispersity of repeat unit length (the value of n in the equation above is an average polymer length).

On a laboratory scale, polyoxyethylene ether detergents can be produced by first forming a good leaving group (such as Cl, Br, I, OMs or OTf) from the hydroxyl group of the alcohol and then reacting this substrate with a mono deprotonated polyethylenglycol. Alternatively, a good leaving group (such as Cl, Br, I, OMs or OTf) can be installed on the polyethylenglycol chain that is reacted in a second step with a deprotonated alcohol.

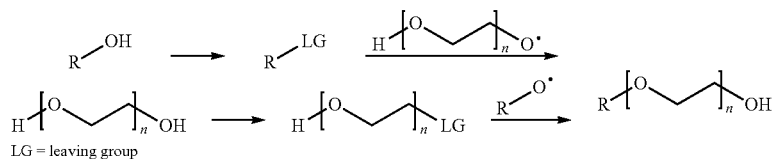

LG = leaving group

Exemplary methods for the synthesis of polyoxyethylene ethers are described in detail, e.g., in U.S. Pat. No. 1,970,578 and Di Serio et al. (2005), which are herewith incorporated by reference in their entirety for all purposes.

While TX-100, Triton N-101 reduced, Triton X-100 reduced and Brij C10 are polyoxyethylene alkyl ethers (=ethoxylation reaction is performed with ethylene oxide gas), it is also possible to perform a similar reaction on an industrial scale using propylene oxide (=propoxylation). The only difference would be methyl group substitution in the PEG chain:

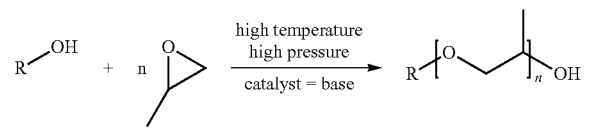

Ethoxylation and propoxylation can also be combined in the same process and lead to a mixed product, such as a mixed polymer polyoxyether comprising oxyethylene and oxypropylene units.

The toxic activity of Triton-X100 arises from the phenol moiety that has the ability to dock in certain endocrine receptors of marine life organisms. By inserting a methylene group between the aromatic ring and the PEG chain, the phenol functionality of Triton-X100 is no longer present in the new structure. In addition, once the PEG chain breaks down after being released in in the environment the revealed benzyl alcohol will easily oxidize to the corresponding benzoic acid. This metabolite has a completely different polarity and geometric structure than a phenol derivative, which will prevent any inhibition in the endocrine receptors.

Based on the above considerations, the present inventors synthesized non-phenolic polyoxyethylene ethers and tested their antiviral activity (see Examples 4 to 10). Thus, the present invention also provides non-phenolic polyoxyethylene ethers of the following general Formula (VIII):

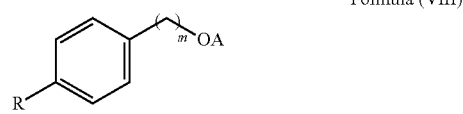

Formula (VIII)

In Formula (VIII) R represents a hydrocarbon group having a linear chain of 2 to 12 carbon atoms and one or more methyl groups as substituents on said linear chain, m represents an integer of 1 to 4, and A represents a polyoxyethylene residue, optionally with the proviso that 29-[4-(1,1,3,3-tetramethylbutyl)phenyl]-3,6,9,12,15,18,21,24,27-nonaoxanonacosan-1-ol having the following structural formula is excluded.

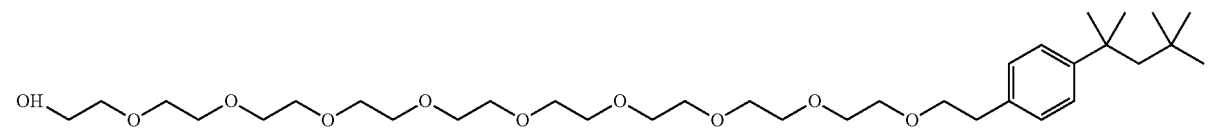

In Formula (VIII) R represents a hydrocarbon group having a linear chain of 2 to 12, preferably 2 to 8, more preferably 2 to 6 and most preferably 4 carbon atoms and one or more, preferably 2 to 6, and most preferably 4 methyl group(s) as substituent(s) on said linear chain.

Preferably R represents a hydrocarbon group having a linear chain of 2 to 12, preferably 2 to 8, more preferably 2 to 6 and most preferably 4 carbon atoms and 2 methyl group(s) as substituent(s) on said linear chain; a hydrocarbon group having a linear chain of 2 to 12, preferably 2 to 8, more preferably 2 to 6 and most preferably 4 carbon atoms and 4 methyl group(s) as substituent(s) on said linear chain; or a hydrocarbon group having a linear chain of 2 to 12, preferably 2 to 8, more preferably 2 to 6 and most preferably 4 carbon atoms and 6 methyl group(s) as substituent(s) on said linear chain.

Most preferably R represents a 2,4,4-trimethyl-pent-2-yl group.

In Formula (VIII) m represents an integer of 1 to 4, preferably an integer of 1 to 2, and most preferably an integer of 1.

In Formula (VIII) A represents a polyoxyethylene residue, preferably a polyoxyethylene residue comprising 2-20 oxyethylene units, more preferably a polyoxyethylene residue comprising 4 to 16 oxyethylene units, even more preferably a polyoxyethylene residue comprising 8 to 12 oxyethylene units, and most preferably a polyoxyethylene residue comprising 9 or 10 oxyethylene units A preferred embodiment of the compound of general Formula (VIII) is a compound wherein R represents a hydrocarbon group having a linear chain of 2 to 6 carbon atoms and 2 to 4 methyl groups as substituents on said linear chain; m represents an integer of 1 to 2; and A represents a polyoxyethylene residue comprising 8 to 12 oxyethylene units.

Another preferred embodiment of the compound of general Formula (VIII) is a compound wherein R represents a hydrocarbon group having a linear chain of 2 to 6 carbon atoms and 2 to 4 methyl groups as substituents on said linear chain; m represents an integer of 1; and A represents a polyoxyethylene residue comprising 8 to 12 oxyethylene units.

A specific preferred embodiment of the compound of general Formula (VIII) is the following compound:

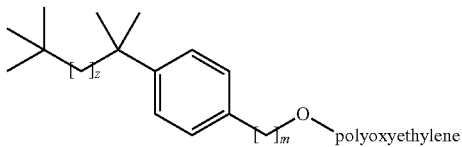

wherein m and z are integers that are independently selected from the following groups:
m=1 to 4, preferably wherein m equals 1;
z=1 to 5.

Another specific preferred embodiment of the compound of general Formula (VIII) is the following compound:

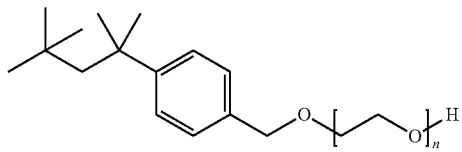

4-tert-octylbenzyl alcohol polyethoxylate wherein n is an integer between 4 and 16, preferably wherein n is equal to 9 or 10.

The compound of Formula (VIII) can be synthesized by commonly known synthetic methods, such as those described in Vogel's Textbook of Practical Organic Chemistry (5th Edition, 1989, A. I. Vogel, A. R. Tatchell, B. S. Furnis, A. J. Hannaford, P. W. G. Smith). For example, 4-tert-octylbenzyl alcohol polyethoxylate can be prepared by converting a phenol comprising a substituent corresponding to group R of general formula (VIII) into the corresponding benzoic acid or homobenzoic acid, reducing the acid group to an alcohol group and reacting the alcohol to form a polyethylene glycol ether (also known as polyoxyethylene ether; POE ether). Herein, ethylene oxide or a suitable polyethylene glycol can serve as a basis for introducing the polyethylene glycol ether functionality (Scheme 1; representative examples of experimental procedures that are effective for carrying out individual transformations can be found, for example, in Bioorganic & Medicinal Chemistry, 16(9), 4883-4907, 2008; Journal of Medicinal Chemistry, 48(10), 3586-3604, 2005; Journal of Physical Chemistry B, 107(31), 7896-7902; 2003; Journal of Nanoparticle Research, 15(11), 2025/1-2025/12, 12 pp., 2013; and PCT Int. Appl., 2005016240, 24 Feb. 2005).

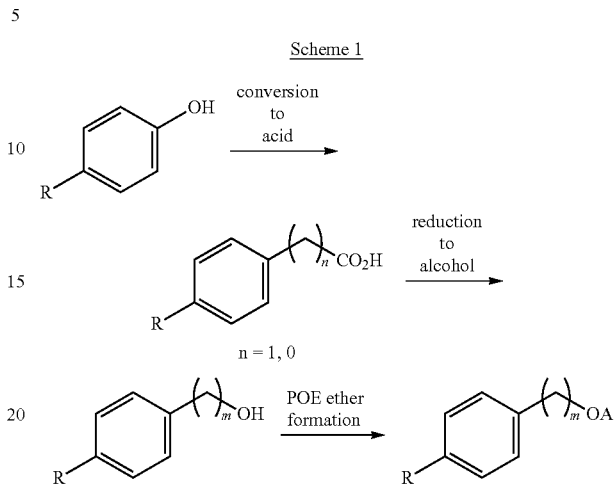

Alternatively, the compound of General Formula (VIII) can be accessed through the alkylation of toluene, followed by functionalization of the benzylic methyl group and further reaction to form a polyethylene glycol ether (Scheme 2; representative examples of experimental procedures that are effective for carrying out individual transformations can be found, for example, in Russian Journal of Applied Chemistry, 82(6), 1029-1032, 2009; Journal of Organic Chemistry, 79(1), 223-229, 2014; and Chemistry—A European Journal, 23(60), 15133-15142, 2017)). The direct alkylation of benzyl alcohol to obtain a suitable intermediate for introducing the polyethylene glycol ether functionality also is envisaged (Scheme 3; representative examples of experimental procedures for corresponding transformations can be found, for example, in Russian Journal of Organic Chemistry, 51(11), 1545-1550, 2015).

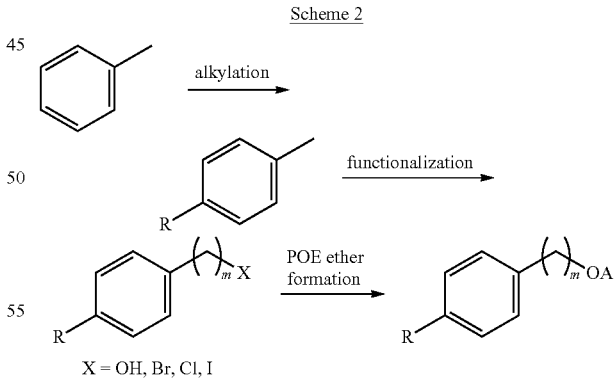

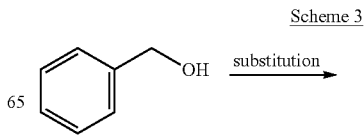

-continued

[Scheme: benzyl alcohol with R substituent undergoes POE ether formation to give R-substituted benzyl polyoxyethylene ether with $m$ repeat units ending in OA]

[Structures: Poly(ethylene glycol) (PEG): HO-(CH₂CH₂O)$_n$-OH shown as HO-[O]$_n$-OH; Methoxypolyethylene glycol (mPEG): H₃C-O-(CH₂CH₂O)$_n$-OH]

The above polyoxyethylene ethers with the structure according to Formula (VIII) can be used in the methods for inactivating a virus having a lipid envelope according to the present invention.

As described above, and as will be clear to a person skilled in the art, the synthesis of polyoxyethylene ethers usually yields products with a wide polydispersity of polyoxytheylene repeat unit lengths. Hence, when the number of polyoxytheylene repeat units is indicated for the polyoxyethylene ethers of the present invention, this number refers to the average polyoxytheylene repeat unit length. The average polyoxytheylene repeat unit length refers to the average number of polyoxytheylene repeat units of all polyoxyethylene ether molecules of a sample. For example, in one embodiment of the method for inactivating a virus having a lipid envelope of the present invention, a detergent is added to a liquid to prepare a mixture of said detergent and said liquid, wherein said detergent can be a polyoxyethylene ether that has the following structure according to Formula (III):

(Formula (III))

[Structure of Formula (III): 4-(2,4,4-trimethylpentan-2-yl)cyclohexyl polyoxyethylene ether with $n$ repeat units terminated by H]

wherein n is equal to 10.

In this embodiment of the method for inactivating a virus having a lipid envelope of the present invention, n=10 in the above Formula (III) will be the average number of polyoxytheylene repeat units of all polyoxyethylene ether molecules that are added to the liquid in accordance with the present invention.

The polyoxyethylene ether detergents used in the methods for inactivating a virus having a lipid envelope according to the present invention have an average number of polyoxytheylene repeat units of 2 to 100, 2 to 50, 2 to 20, or 4 to 16, or 9 or 10. Preferably, the average number of polyoxytheylene repeat units is 4 to 16, more preferably 9 or 10, and most preferably 10.

As will be clear to a person skilled in the art, in the polyoxyethylene/polyoxypropylene ether detergents in accordance with the present invention a methyl group may be attached to the terminal hydroxyl group of the polyoxyethylene/polyoxypropylene moiety (i.e., the terminal hydroxyl group may be blocked). Such blocking of the terminal hydroxyl group may facilitate synthesis. This is particularly useful for compounds not made through ethoxylation or propoxylation, such as compounds made in accordance with Scheme 1 or Scheme 2 above. Structures with a methyl-blocked polyoxyethylene/polyoxypropylene moiety are usually referred as mPEG derivatives, as illustrated by the following exemplary structures:

As will be clear to a person skilled in the art, also the synthesis of polyoxypropylene ethers usually yields products with a wide polydispersity of polyoxypropylene repeat unit lengths. Hence, when the number of polyoxypropylene repeat units is indicated for the polyoxypropylene ethers in accordance with the present invention, this number refers to the average polyoxypropylene repeat unit length. As described for polyoxyethylene ethers above, the average polyoxypropylene repeat unit length refers to the average number of polyoxypropylene repeat units of all polyoxypropylene ether molecules of a sample.

The polyoxypropylene ether detergents used in accordance with the present invention have an average number of polyoxypropylene repeat units of 2 to 100, 2 to 50, 2 to 20, or 5 to 15, or 9 or 10. Preferably, the average number of polyoxypropylene repeat units is 5 to 15, more preferably 9 or 10, and most preferably 10.

In one embodiment of the present invention, the polyoxyethylene ether that is used in the methods for inactivating a virus having a lipid envelope according to the present invention has the following structure according to Formula (II):

(Formula (II))

[Structure of Formula (II): 4-(2,4,4-trimethylpentan-2-yl)cyclohexyl-O-polyoxyethylene]

In a preferred embodiment of the present invention, the compound represented by the above Formula (II) is the commercially available Triton X-100 reduced (CAS No. 92046-34-9).

In one embodiment of the present invention, the polyoxyethylene ether that is used in the methods for inactivating a virus having a lipid envelope according to the present invention has the following structure according to Formula (IV):

(Formula (IV))

[Structure of Formula (IV): 4-(2,4,4-trimethylpentyl)cyclohexyl-O-polyoxyethylene]

In a preferred embodiment of the present invention, the compound represented by the above Formula (IV) is the commercially available Triton N-101 reduced (CAS No. 123359-41-1).

In one embodiment of the present invention, the polyoxyethylene ether that is used in the methods for inactivating a virus having a lipid envelope according to the present invention has the following structure according to Formula (VI):

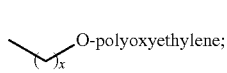
(Formula (VI))

wherein x equals 15.

In a preferred embodiment of the present invention, the compound represented by the above Formula (VI) is the commercially available Brij C10 (CAS No. 9004-95-9).

In accordance with all other embodiments of the invention, in the methods for inactivating a virus having a lipid envelope of the present invention, the polyoxyethylene ethers may also be replaced by monooxyethylene ethers. In a preferred embodiment of the invention, said monooxyethylene ethers have the following structure according to Formula C:

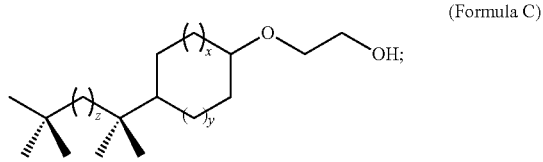
(Formula C)

wherein x, y and z are integers that are independently selected from the following groups:

x=0 to 5
y=0 to 5
z=0 to 20

Preferably, said monooxyethylene ethers have the following structure according to Formula D:

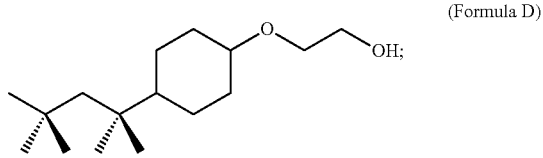
(Formula D)

or the following structure according to Formula E:

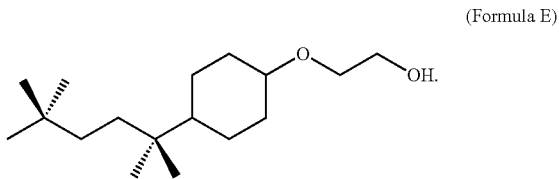
(Formula E)

In accordance with all other embodiments of the invention, the present invention also provides monooxyethylene ethers corresponding to the polyoxyethylene ethers provided by the present invention. In a preferred embodiment of the invention, said monooxyethylene ethers have the following structure according to Formula F:

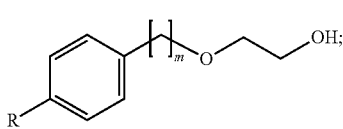
(Formula F)

wherein R represents a hydrocarbon group having a linear chain of 2 to 12 carbon atoms and one or more methyl groups as substituents on said linear chain; m represents an integer of 1 to 4, and A represents a polyoxyethylene residue.

In another preferred embodiment, the monooxyethylene ether of Formula F is the following compound:

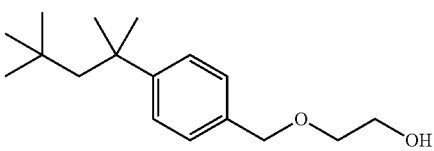 [SMILES: CC(C)(C)CC(C)(C)c1ccc(COCCO)cc1]

The above monooxyethylene ethers with the structures according to Formula F can be used in the methods for inactivating a virus having a lipid envelope according to the present invention.

In the methods for inactivating a virus having a lipid envelope according to the present invention, a detergent is added to a liquid to prepare a mixture of said detergent and said liquid. In one embodiment of the invention, the polyoxyethylene ether detergents are added to the liquid to yield a final concentration of about 0.03% (w/w) to 10% (w/w), preferably about 0.05% (w/w) to 10% (w/w), more preferably 0.1% (w/w) to 10% (w/w), even more preferably about 0.5% (w/w) to 5% (w/w), most preferably about 0.5% (w/w) to 2% (w/w) polyoxyethylene ether detergent in the liquid.

In a preferred embodiment of the methods for inactivating a virus having a lipid envelope of the present invention, the polyoxyethylene ethers that are used in the methods are suitable for the inactivation of said virus having a lipid envelope. Inactivation as used herein refers to disrupting the ability of the lipid-enveloped virus to infect cells. As will be clear to a person skilled in the art, the ability of a lipid-enveloped virus to infect cells, i.e. the infectivity of a lipid-enveloped virus, is typically assessed by determining the number of infectious virus particles in a solution. Exemplary methods for determining the number of infectious virus particles in a solution are described herein.

In one embodiment, in the method for inactivating a virus having a lipid envelope of the present invention, the step of adding a detergent and a solvent to a liquid is carried out in a way that a solvent/detergent mixture for inactivation of said virus is prepared. Preferably, said solvent is an organic solvent and even more preferably, said solvent is tri-n-butyl phosphate. It is understood that the concentration of the detergent and the type and concentration of solvent can appropriately be chosen by a skilled person, by taking into account, for instance, the potential viruses present in the liquid, the desired LRV, the properties of the biopharmaceutical drug that may be present in the liquid and the characteristics of the manufacturing process of the biopharmaceutical drug that may be present in the liquid (e.g. at which temperature the inactivation will be carried out). Typically, the final concentrations of an organic solvent and a single detergent during the incubation in accordance with the invention is about 0.01% (w/w) to about 5% (w/w) of organic solvent and about 0.05% (w/w) to about 10% (w/w) of detergent, preferably about 0.1% (w/w) to about 5% (w/w) of organic solvent and about 0.1% (w/w) to about 10% (w/w) of detergent, more preferably about 0.1% (w/w) to about 1% (w/w) of organic solvent and about 0.5% (w/w) to about 5% (w/w) of detergent, most preferably about 0.1% (w/w) to about 0.5% (w/w) of organic solvent and about 0.5% (w/w) to about 2% (w/w) of detergent.

In another embodiment, in the method for inactivating a virus having a lipid envelope of the present invention, the step of adding a detergent (and optionally also a solvent) to a liquid is carried out in a way that a further detergent is added to the liquid. Preferably, said further detergent is polyoxyethylene (80) sorbitan monooleate (also known as, e.g., Polysorbate 80 or TWEEN 80). Preferably, said solvent is an organic solvent and even more preferably, said solvent is tri-n-butyl phosphate. It is understood that the concentration of the detergent in accordance with the present invention, the type and concentration of the further detergent as well as the type and concentration of the solvent can appropriately be chosen by a skilled person, by taking into account, for instance, the potential viruses present in the liquid, the desired LRV, the properties of the biopharmaceutical drug that may be present in the liquid and the characteristics of the manufacturing process of the biopharmaceutical drug that may be present in the liquid (e.g. at which temperature the inactivation will be carried out). Typically, the final concentration of an organic solvent is about 0.01% (w/w) to about 5% (w/w), the final concentration of the detergent in accordance with the present invention is about 0.05% (w/w) to about 10% (w/w), and the final concentration of the further detergent is about 0.01% (w/w) to about 5% (w/w). Preferably, the final concentration of an organic solvent is about 0.1% (w/w) to about 5% (w/w), the final concentration of the detergent in accordance with the present invention is about 0.1% (w/w) to about 10% (w/w), and the final concentration of the further detergent is about 0.1% (w/w) to about 5% (w/w). More preferably, the final concentration of an organic solvent is about 0.1% (w/w) to about 1% (w/w), the final concentration of the detergent in accordance with the present invention is about 0.5% (w/w) to about 5% (w/w), and the final concentration of the further detergent is about 0.1% (w/w) to about 1% (w/w). Most preferably, the final concentration of an organic solvent is about 0.1% (w/w) to about 0.5% (w/w), the final concentration of the detergent in accordance with the present invention is about 0.5% (w/w) to about 2% (w/w), and the final concentration of the further detergent is about 0.1% (w/w) to about 0.5% (w/w).

In another embodiment in accordance with the invention, only one detergent is used. For example, in one embodiment of the method of the invention, in step a) no further detergent other than the detergent of the invention is added. In another embodiment of the method of the invention, in the method no further detergent other than the detergent of the invention is added. In another embodiment in accordance with the invention, in the use of a detergent of the invention in a method for the inactivation of a virus having a lipid envelope, no further detergent other than the detergent of the invention is used. One advantage of these embodiments is that a single detergent can more easily be removed in subsequent (method) steps. For example, a single detergent can be removed more easily as compared to the three components used in a standard solvent/detergent (S/D) treatment, which typically include two detergents and one solvent, in particular an organic solvent. Thus, in another embodiment in accordance with the invention, the composition comprising a detergent of the invention does not comprise any further detergent other than said detergent.

In another embodiment in accordance with the invention, no organic solvent is used. For example, in one embodiment of the method of the invention, in step a) no organic solvent is added. In another embodiment in accordance with the invention, in the use of a detergent of the invention in a method for the inactivation of a virus having a lipid envelope, no organic solvent is used. In another embodiment in accordance with the invention, the composition comprising a detergent of the invention does not comprise any organic solvent.

As outlined above, the method for inactivating a virus having a lipid envelope according to the present invention is particularly useful in biopharmaceutical production processes, wherein the absence of active (i.e., infectious) virus from the final product has to be ensured in order to guarantee patient safety. Hence, in one embodiment, in the methods for inactivating a virus having a lipid envelope according to the present invention, a detergent is added to a liquid that comprises a biological medicinal product or a biopharmaceutical drug, preferably a biopharmaceutical drug. In a preferred embodiment of the present invention, said biopharmaceutical drug is not a viral vaccine. Biopharmaceutical drugs in accordance with the invention are not particularly limited. They include both recombinant biopharmaceutical drugs and biopharmaceutical drugs from other sources such as biopharmaceutical drugs obtained from human plasma. Biopharmaceutical drugs in accordance with the invention include, without limitation, blood factors, immunoglobulins, replacement enzymes, vaccines, gene therapy vectors, growth factors and their receptors. In a preferred embodiment, the biopharmaceutical drug is a therapeutic protein. Preferred blood factors include factor I (fibrinogen), factor II (prothrombin), Tissue factor, factor V, factor VII and factor VIIa, factor VIII, factor IX, factor X, factor XI, factor XII, factor XIII, von Willebrand Factor (VWF), prekallikrein, high-molecular-weight kininogen (HMWK), fibronectin, antithrombin III, heparin cofactor II, protein C, protein S, protein Z, plasminogen, alpha 2-antiplasmin, tissue plasminogen activator (tPA), urokinase, plasminogen activator inhibitor-1 (PAI1), and plasminogen activator inhibitor-2 (PAI2). Factor VIII is a particularly preferred blood factor, and recombinant Factor VIII is even more preferred. The blood factors that can be used in accordance with the present invention are meant to include functional polypeptide variants and polynucleotides that encode the blood factors or encode such functional variant polypeptides. Preferred immunoglobulins include immunoglobulins from human plasma, monoclonal antibodies and recombinant antibodies. The biopharmaceutical drugs in accordance with the invention are preferably the respective human or recombinant human proteins or functional variants thereof.

As indicated above, the biopharmaceutical drug in accordance with the present invention may also be a gene therapy vector, including a viral gene therapy vector. As will be clear to a person skilled in the art, the methods for inactivating a virus having a lipid envelope of the present invention generally do not inactivate non-enveloped viruses. Thus, in a preferred embodiment, where the biopharmaceutical drug in accordance with the present invention is a viral gene therapy vector, such viral gene therapy vector is based on a non-enveloped virus. In a preferred embodiment, such viral gene therapy vector is based on adeno-associated virus (AAV).

In accordance with all other embodiments of the present invention, the method for inactivating a virus having a lipid envelope of the present invention may comprise, after the step of incubating said mixture to inactivate said virus, a step of purifying said biopharmaceutical drug. Preferably, said purifying comprises separating said biopharmaceutical drug from said detergent(s). The skilled person will be aware of various methods to separate a biopharmaceutical drug from detergent(s). Such methods can be selected by a person skilled in the art taking into account the properties of the biopharmaceutical drug, the source from which it is obtained (e.g. recombinantly or from other sources such as from human plasma) and the desired biopharmaceutical application (e.g. whether it will be administered subcutaneously or intravenously, etc.). For example, a biopharmaceutical drug may be separated from detergent(s) using chromatography, such as anion exchange chromatography or cation exchange chromatography. In one embodiment, said purifying from said detergent(s) comprises more than one chromatographic purifications.

In accordance with all other embodiments of the present invention, the method for inactivating a virus having a lipid envelope of the present invention may comprise a step of filtering said mixture, preferably with a depth filter. This step of filtering can be carried out before the step of adding a detergent to a liquid to prepare a mixture of said detergent and said liquid. Alternatively, this step of filtering can be carried out between the step of adding a detergent to a liquid to prepare a mixture of said detergent and said liquid and the step of incubating said mixture to inactivate said virus.

In another embodiment in accordance with all other embodiments of the present invention, in the methods for inactivating a virus having a lipid envelope, the step of incubating said mixture to inactivate said virus can be carried out in a way that said mixture is incubated for at least 10 min, for at least 30 min, for at least 1 hour, for at least 2 hours, for at least 4 hours, for at least 12 hours or for at least 24 hours.

In another embodiment in accordance with all other embodiments of the present invention, in the step of incubating said mixture to inactivate said virus, said mixture is incubated at a low temperature, such as a temperature between 0° C. and 15° C., between 0° C. and 10° C., between 0° C. and 8° C., between 0° C. and 6° C., between 0° C. and 4° C., or between 0° C. and 2° C., preferably between 0° C. and 10° C. In an alternative embodiment in accordance with all other embodiments of the present invention, in the step of incubating said mixture to inactivate said virus, said mixture is incubated at or close to room temperature, such as a temperature between 16° C. and 25° C., between 18° C. and 24° C., or between 20° C. and 23° C.

It is to be understood that the way in which the steps of the method of the present invention are to be carried out is not particularly limited. In particular, the method steps may be carried out in a batch-wise fashion. Alternatively, the method steps may also be carried out in a semi-continuous or continuous fashion.

As outlined above, the method for inactivating a virus having a lipid envelope according to the present invention is particularly useful in biopharmaceutical production processes. Thus, the present invention also relates to a method for preparing a biopharmaceutical drug, said method comprising the method steps of the method for inactivating a virus having a lipid envelope in accordance with the present invention and any embodiments thereof. Preferably, the method for preparing a biopharmaceutical drug in accordance with the present invention comprises a step of preparing a pharmaceutical formulation comprising said biopharmaceutical drug, which is performed subsequent to the steps of the method for inactivating a virus having a lipid envelope according to the present invention. Such pharmaceutical formulation can be prepared in accordance with known standards for the preparation of pharmaceutical formulation. For example, the formulation can be prepared in a way that it can be stored and administered appropriately, e.g. by using pharmaceutically acceptable components such as carriers, excipients or stabilizers. Such pharmaceutically acceptable components are not toxic in the amounts used when administering the pharmaceutical formulation to a patient.

The present inventors have surprisingly found that the polyoxyethylene ether detergents according to the present invention are particularly useful for inactivating virus having a lipid envelope. Thus, the present invention also relates to the use of the disclosed polyoxyethylene ether detergents according to the present invention in any method for the inactivation of a virus having a lipid envelope. Preferably, said method for said inactivation of said virus is a method using a solvent/detergent treatment, wherein said solvent/detergent treatment comprises the use of said detergent of the present invention. In another embodiment, said virus inactivation is an inactivation of virus in a liquid comprising a biopharmaceutical drug.

Since the present inventors have surprisingly found that the non-phenolic polyoxyethylene ether detergents according to the present invention are particularly useful for inactivating virus having a lipid envelope, the present invention also relates to the polyoxyethylene ether detergents according to the present invention, and to a composition comprising a polyoxyethylene ether detergent according to the present invention. In another embodiment, the composition comprising a polyoxyethylene ether detergent according to the present invention additionally comprises a biopharmaceutical drug and/or an organic solvent and/or a further detergent.

The present invention also provides a kit for virus inactivation, comprising a polyoxyethylene ether detergent according to the present invention or the composition comprising a polyoxyethylene ether detergent according to the present invention, and further comprising a chromatography resin for a chromatographic purification. In another embodiment, said kit further comprises a depth filter.

The present invention provides non-phenolic polyoxyethylene ethers. As described above, these polyoxyethylene ethers can be used in the methods for inactivating a virus having a lipid envelope according to the present invention. However, these non-phenolic polyoxyethylene ethers, as well as all other non-phenolic polyoxyethylene ethers in accordance with the present invention, can also be used for various other purposes, e.g. for those in which Triton X-100 is commonly used. For example, the non-phenolic polyoxyethylene ethers in accordance with the present invention can be used in the laboratory. In the laboratory they can be used, e.g., to lyse cells to extract protein or organelles, or to permeabilize the membranes of living cells; to permeabilize unfixed (or lightly fixed) eukaryotic cell membranes; to solubilize membrane proteins in their native state in conjunction with zwitterionic detergents such as CHAPS; as part of the lysis buffer (usually in a 5% solution in alkaline lysis buffer) in DNA extraction; to reduce surface tension of aqueous solutions during immunostaining (usually at a concentration of 0.1-0.5% in TBS or PBS Buffer); to restrict colony expansion in *Aspergillus nidulans* in microbiology; to decellularize animal-derived tissues; or to remove SDS from SDS-PAGE gels prior to renaturing the proteins within the gel. In another embodiment, the non-phenolic polyoxyethylene ethers in accordance with the present invention can be used in the electronic industry, e.g. as a wetting agent for the slats to improve and speed up some procedures and operations. In another embodiment, the non-phenolic polyoxyethylene ethers in accordance with the present invention can have medical uses, e.g. they can be used as a substitute for the spermicide Nonoxinol 9, or as a pharmaceutical excipient, or as an ingredient in influenza vaccine (Fluzone). In further embodiments, the non-phenolic polyoxyethylene ethers in accordance with the present invention can be used in several types of cleaning compounds, ranging from heavy-duty industrial products to gentle detergents; they can be used as an ingredient in homemade vinyl record cleaning fluids together with distilled water and isopropyl alcohol; they can be used during the cleaning of diamond blades; they can be used in formulations for polymerization of emulsions; they can be used in tires; they can be used in washing and cleaning agents; they can be used in industry as starting chemical for the production of polymers or glues; they can be used in household or industrial cleaners, in paints or coatings, in pulp or paper, on the oilfield, in textiles, in agrochemicals, in metalworking fluids; they can be used for the dispersion of carbon materials for soft composite materials; or they can be used in the plating of metal.

In the following, the present invention will be illustrated by examples, without being limited thereto.

EXAMPLES

As outlined above, recent ecological studies have raised environmental concerns regarding the use of Triton X-100 in biopharmaceutical production processes. Based on structural considerations, the present inventors have identified candidate detergents as useful alternatives to Triton X-100 which have not been associated with negative environmental impact. In particular, the present inventors have surprisingly identified polyoxyethylene ethers as suitable alternatives to Triton X-100 for inactivating lipid-enveloped viruses by solvent/detergent (S/D) treatment during biopharmaceutical production. In the following experiments, the suitability of exemplary candidate detergents for S/D treatment was tested on intravenous immunoglobulin (IVIG)- and human serum albumin (HSA)-containing liquids. Additionally, in the following experiments 4-tert-octylbenzyl alcohol polyethoxylate was synthesized, and the suitability of 4-tert-octylbenzyl alcohol polyethoxylate and other polyoxyethylene ethers for S/D treatment as well as single-detergent treatment was tested on various test items.

Example 1: HIV and PRV Inactivation Using Triton X-100 Reduced or Triton N-101 Reduced in Liquids Comprising Intravenous Immunoglobulin The suitability of Triton X-100 reduced or Triton N-101 reduced for S/D treatment to inactivate the lipid-enveloped viruses human immunodeficiency virus (HIV) and pseudorabies virus (PRV) in liquids comprising intravenous immunoglobulin (IVIG) was tested and compared to Triton X-100. To this end, virus was added to liquids comprising IVIG. The virus-containing liquids comprising IVIG were then incubated with S/D mixtures comprising low concentrations of Triton X-100 reduced, Triton N-101 reduced or Triton X-100 for various time periods, and the remaining infectivity of the viruses was determined. Triton X-100 reduced, Triton N-101 reduced and Triton X-100 were used at low concentrations in order to evaluate the kinetics of virus inactivation, i.e., the efficiency of virus inactivation (expressed by the RF) over time. As will be clear to a person skilled in the art, in commercial production processes such as biopharmaceutical production, the detergents of the invention including Triton X-100 reduced or Triton N-101 reduced can be used at significantly higher concentrations, which will accelerate the kinetics of virus inactivation and is also expected to increase the achieved LRV.

Materials

Liquid Comprising IVIG

A liquid comprising IVIG (IVIG-containing liquid) was frozen on dry ice and stored at ≤−60° C. until use within one year after the date of collection.

Viruses

Pseudorabies virus (PRV; Family Herpesviridae; enveloped; dsDNA; Ø=120-200 nm) was used as a model for large enveloped DNA viruses.

Human immunodeficiency virus (HIV; Family Retroviridae; enveloped; ssRNA; Ø=80-100 nm) was used as a relevant target virus and a model for other lipid-enveloped RNA (ribonucleic acid) viruses like HIV-2.

TABLE 1

Virus stocks used in the experiments.

| Virus Strain | Source | Propagated on | | Titrated on | |
|---|---|---|---|---|---|
| | | Cell line | Source | Cell line | Source |
| PRV | | | | | |
| Kaplan | Eberhard Karls University, Tübingen, Germany | Vero | ECACC[1] 84113001 | Vero | ECACC[1] 84113001 |
| HIV | | | | | |
| HIV-1 HIB | NIAID[2] #398 | H9 | ECACC[1] 85050301 | AA2 | NIAID[2] #135 |

ECACC[1] European Collection of Authenticated Cell Cultures, Public Health England Porton Down, Salisbury, SP4 0JG UK
NIAID[2] National Institute of Allergies and Infectious Diseases, 5601 Fishers Lane, MSC 9806, Bethesda MD 20892-9806 USA Virus stocks were characterized prior to use. This characterization included the determination of the virus titer by at least ten independent titrations and specification of an acceptance virus titer range for use as positive control, the determination of virus stock protein content, PCR tests for virus identity and contamination with other viruses and *mycoplasma* and tests for virus aggregation with filters not allowing the passage of large virus aggregates. Only virus stocks passing PCR identity/contamination tests with no significant aggregation, (i.e. difference in infectivity titers between virus stock and filtered stock was smaller than 1.0 log) were used.

Triton X-100 Reduced or Triton N-101 Reduced Reagent Mixes

The S/D components Polysorbate 80 (PS80, Crillet 4 HP, Tween 80) and Tri-n-butyl-phosphate (TnBP) were combined with the respective detergent (i.e. Triton X-100, Triton X-100 reduced or Triton N-101 reduced) in the following ratio (see Table 2 to Table 4):

TABLE 2

Amount of components for Triton X-100 S/D Reagent Mix

| S/D Reagent | Amount to be combined for S/D Reagent Mix [g] |
|---|---|
| Triton X-100 | 10.61 ± 0.11 |
| PS80 | 3.23 ± 0.03 |
| TnBP | 2.93 ± 0.03 |
| Resulting S/D reagent | 16.77 |

TABLE 3

Amount of components for Triton X-100 reduced S/D Reagent Mix

| S/D Reagent | Amount to be combined for S/D Reagent Mix [g] |
|---|---|
| Triton X-100 reduced | 10.61 ± 0.11 |
| PS80 | 3.23 ± 0.03 |
| TnBP | 2.93 ± 0.03 |
| Resulting S/D reagent | 16.77 |

TABLE 4

Amount of components for Triton N-101 reduced S/D Reagent Mix

| S/D Reagent | Amount to be combined for S/D Reagent Mix [g] |
|---|---|
| Triton N-101 reduced | 10.61 ± 0.11 |
| PS80 | 3.23 ± 0.03 |
| TnBP | 2.93 ± 0.03 |
| Resulting S/D reagent | 16.77 |

Each mixture was stirred for at least 15 minutes. The S/D reagent mixes were stored at room temperature for use within one year. Prior to use the respective S/D reagent mix was stirred again for at least 15 minutes to assure homogeneity.

Methods

The virus inactivation capacity and the robustness of the S/D treatment were evaluated under conditions unfavorable for virus inactivation, i.e. with short incubation times and at relatively low temperatures. As will be clear to a person skilled in the art, in commercial production processes such as biopharmaceutical production, longer incubation times and higher temperatures can be used, which will accelerate the kinetics of virus inactivation and may also increase the achieved LRV. Further, as already mentioned above, low concentrations of S/D components were used. As will be clear to a person skilled in the art, in commercial production processes such as biopharmaceutical production, higher concentrations of S/D components can be used, which will accelerate the kinetics of virus inactivation and may also increase the achieved LRV.

Since the protein concentration has no significant impact on virus inactivation during S/D treatment (see also Dichtelmüller et al., 2009), the robustness concerning protein content was not investigated.

The IVIG-containing liquid was thawed and all further steps took place in a biosafety class II cabinet. The IVIG-containing liquid was incubated under stirring at a temperature of +17° C.±1° C. using a double-walled vessel connected to a cryostat for incubation. The IVIG-containing liquid was then filtered through a 0.2 μm depth filter with an effective filter area of 25 cm² (Zeta Plus® VR06, Cuno/3M or equivalent) connected to a Sartorius (SM16249) stainless steel filter holder using pressurized nitrogen at a targeted pressure of 0.9 bar (limit: 0.5 bar-1.5 bar). For conditioning the filter material was pre-coated with 55 l/m² of the Hyflo Supercel suspension (5.0 g±0.05 g of Hyflo Supercel per L; conductivity adjusted to 3.5 mS/cm (specified range: 2.5-6.0 mS/cm) using 3 M NaCl) (at a pressure of ≤0.5 bar) prior to filtration of the liquid. During filtration the filter holder was cooled and the filtrate was collected at a targeted temperature of ≤18° C. using a double-walled vessel connected to a cryostat. The vessel for the filtrate was cooled. In case of filter clogging, fresh pre-conditioned filters were used for continuing filtration of the remaining liquid. After filtration, the temperature (target: ≤-18° C.) and the volume were measured.

After measuring the volume of the IVIG-containing liquid, it was adjusted under stirring with cold (+2° C. to +8° C.) dilution buffer (NaCl solution with target conductivity of 3.5 mS/cm (range: 2.5 mS/cm-6.0 mS/cm)) to a calculated target absorbance of 28.9 $AU_{280-320}$/cm (range: 14.5-72.3 $AU_{280-320}$/cm). Taking the later 1:31 virus spike into account, this resulted in a calculated target absorbance value of 28 $AU_{280-320}$/cm (range: 14-70 $AU_{280-320}$/cm) for incubation with S/D reagents after filtration.

The filtered and protein adjusted IVIG-containing liquid was again adjusted under stirring to +17° C.±1° C. using a double-walled vessel connected to a cryostat. This temperature range was maintained under stirring until the end of the incubation of the filtered IVIG-containing liquid with the S/D reagents and was recorded continuously. The determined volume of the filtered IVIG-containing liquid, transferred to a screw-cap flask of which the tare weight had been determined, was spiked with virus at a ratio of 1:31, e.g. 30 mL of liquid comprising IVIG were spiked with 1 mL of virus stock solution. The spiked IVIG-containing liquid was further incubated under continued stirring at 17° C.±1° C. Within 1-2 minutes after spiking, samples for virus titration (0.5 mL Spike Control, SC, and 2 mL Hold Control, HC) were taken.

After drawing, the Hold Control (HC) was kept at the same temperature, i.e. at +17° C.±1° C., as the spiked process material after addition of S/D reagents, i.e. it was stored in the same cooling circle as the vessel with the IVIG-containing liquid, until the end of S/D treatment. The temperature of the cooling liquid was determined before insertion of the Hold Control sample and, again, shortly before the Hold Control was removed for titration after S/D treatment.

The weight of the spiked IVIG-containing liquid was determined for calculation of the amount of the S/D reagent mix to be added. The weighed material was re-adjusted, if necessary, under stirring to +17° C.±1° C. The respective S/D reagent mix was added to the IVIG-containing liquid to give a final concentration of 0.05% of the respective polyoxyethylene ether detergent. The S/D reagent mix was added under stirring within 1 minute using a syringe, and the actual amount of S/D reagent mix added was determined by back-weighing the syringe. The spiked IVIG-containing liquid was further incubated with S/D reagents under continued stirring at +17° C.±1° C. for 59±1 minutes. During incubation, 1 mL samples for virus titration were taken after 1-2 min, 10±1 min, 30±1 min and 59±1 min. To prevent further inactivation of virus by the S/D reagents following sample drawing, the samples were diluted immediately 1:20 with cold (+2° C. to +8° C.) cell culture medium (i.e. 1 volume of sample plus 19 volumes of cell culture medium).

In order to titrate samples, serial 0.5 log dilutions of the samples were prepared in the appropriate tissue culture medium and 100 μL of each dilution were added to each of 8 wells of a microtiter plate seeded with the respective indicator cell line. The cells were incubated for 7 days at 36.0° C. (setpoint) before the cytopathic effect was evaluated by visual inspection under a microscope. Median tissue culture infectious doses (TCID$_{50}$) were calculated according to the Poisson distribution and expressed as log$_{10}$[TCID$_{50}$/mL].

The calculation of the virus clearance capacity was carried out according to the following formula:

$$R = \log\left(\frac{V_1 \times T_1}{V_2 \times T_2}\right)$$

where,

R=virus reduction factor $V_1$=volume of starting material [mL]

$T_1$=concentration of virus in starting material [TCID$_{50}$/mL]

$V_2$=volume of material after virus inactivation [mL]

$T_2$=concentration of virus after virus inactivation [TCID$_{50}$/mL]

The volumes and the titers of each spiked sample before and after treatment were used to calculate R. Whenever no virus was detected, the detection limit was taken as the virus titer for calculation.

Results

Figure 1:
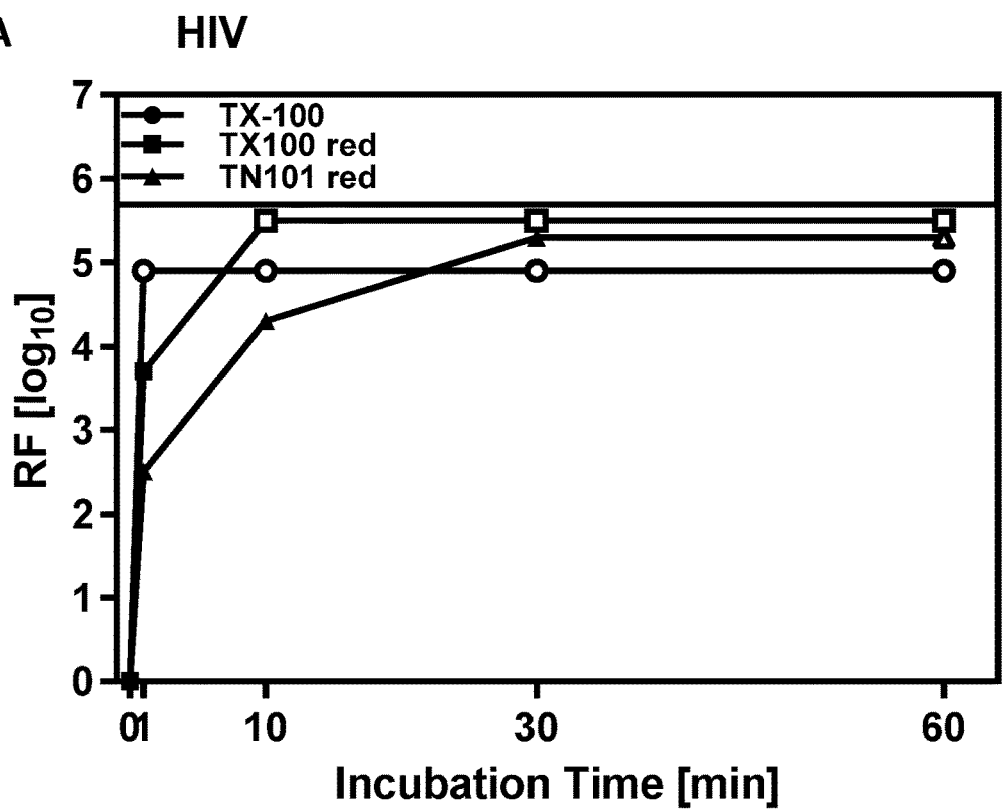
FIG. 1: Virus inactivation efficiency of low concentrations of Triton X-100 reduced or Triton N-101 reduced in S/D treatment of IVIG-containing liquid at 17° C.±1° C. A three-component mixture was used to give final concentrations of 0.04%-0.06% Triton X-100 reduced or Triton N-101 reduced, 0.01%-0.02% Polysorbate 80, 0.01%-0.02% TnBP (side-by-side comparison with same concentration of Triton X-100). Virus inactivation over time is indicated by the virus reduction factor (RF) for two runs with HIV (A and B, respectively). Virus inactivation of S/D treatment using Triton X-100 reduced ("TX-100 red.") or Triton N-101 reduced ("TN-101 red.") was compared to virus inactivation of S/D treatment using Triton X-100 ("TX-100").
Figure 1:
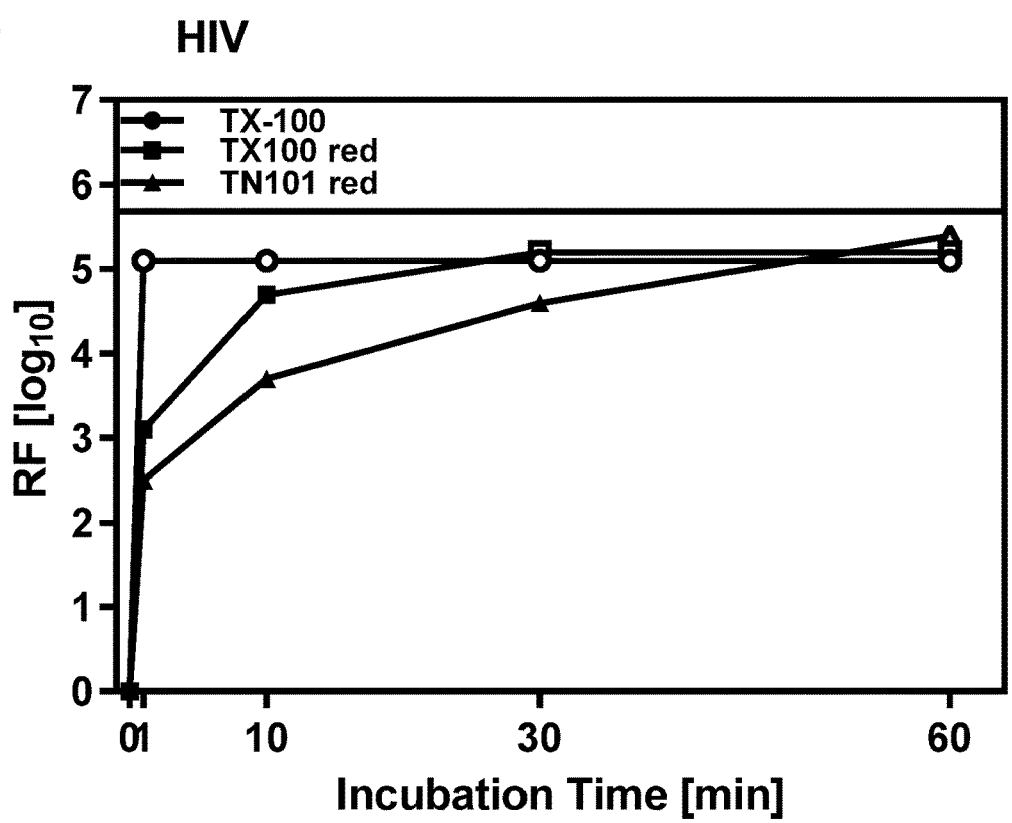

When S/D treatment of an IVIG-containing liquid was performed using a mixture of Triton X-100 reduced, PS80 and TnBP or a mixture of Triton N-101 reduced, PS80 and TnBP, HIV was inactivated by a virus reduction factor (RF) of at least 4 within 10 minutes (FIG. 1A). Similar results were obtained in a repeat experiment (FIG. 1B).

Figure 2:
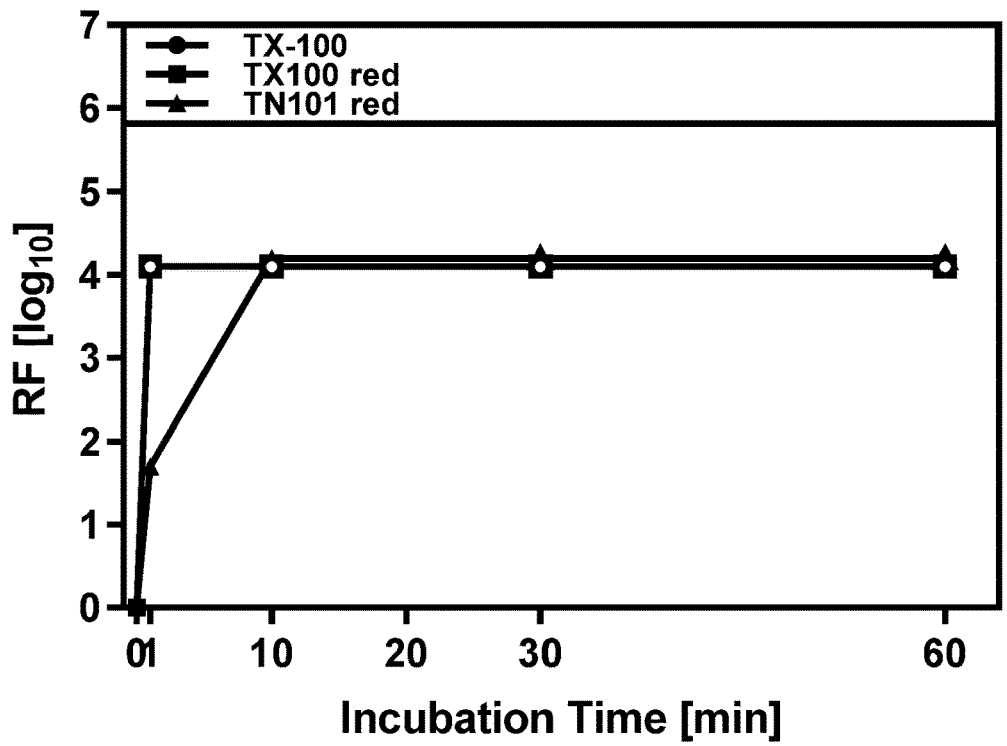
FIG. 2: Virus inactivation efficiency of low concentrations of Triton X-100 reduced or Triton N-101 reduced in S/D treatment of IVIG-containing liquid at 17° C.±1° C. A three-component mixture was used to give final concentrations of 0.04%-0.06% Triton X-100 reduced or Triton N-101 reduced, 0.01%-0.02% Polysorbate 80, 0.01%-0.02% TnBP (side-by-side comparison with same concentration of Triton X-100). Virus inactivation over time is indicated by the virus reduction factor (RF) for two runs with PRV (A and B, respectively). Virus inactivation of S/D treatment using Triton X-100 reduced ("TX-100 red.") or Triton N-101 reduced ("TN-101 red.") was compared to virus inactivation of S/D treatment using Triton X-100 ("TX-100").
Figure 2:
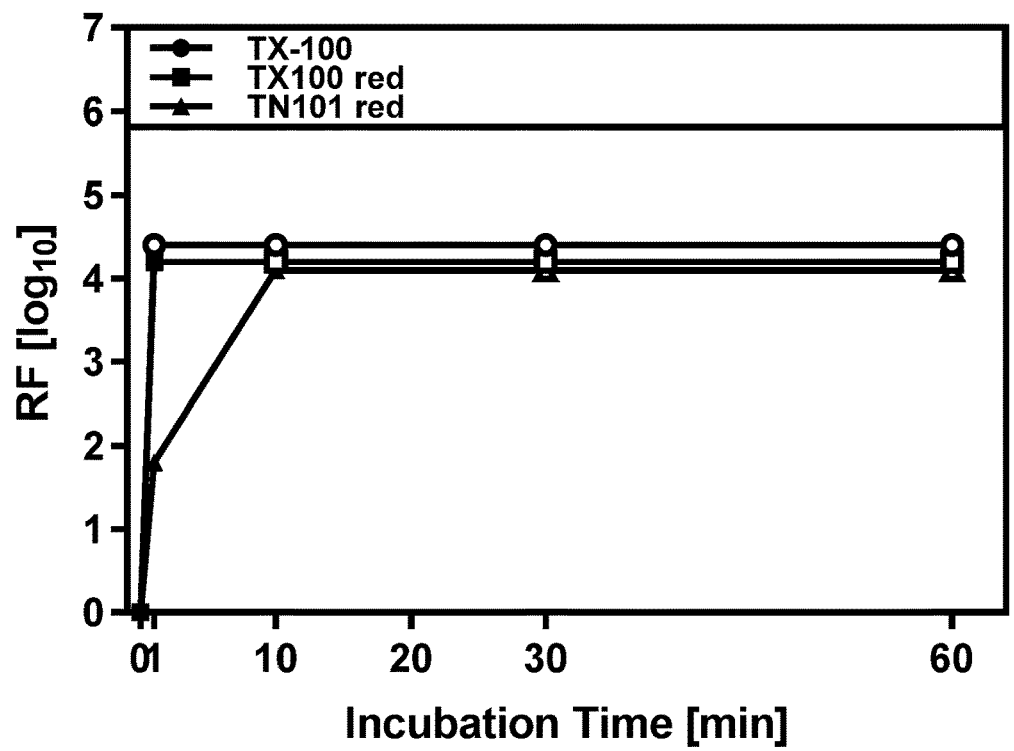

In additional experiments, when S/D treatment of an IVIG-containing liquid was performed using a mixture of Triton X-100 reduced, PS80 and TnBP or a mixture of Triton N-101 reduced, PS80 and TnBP, PRV was inactivated by a RF of around 4 within 10 minutes (FIG. 2A). Similar results were obtained in a repeat experiment (FIG. 2B).

These experiments show that replacing Triton X-100 by Triton X-100 reduced or Triton N-101 reduced for S/D treatment of biopharmaceutical drug-containing liquids results in efficient inactivation of lipid-enveloped viruses, even at low concentrations of the detergents.

Example 2: HIV, PRV and BVDV Inactivation Using Brij C10 in Liquids Comprising Intravenous Immunoglobulin Materials and Methods The experiments were performed as described for Example 1 above. However, for the S/D treatment an S/D mixture comprising Brij C10 was tested and compared to an S/D mixture comprising Triton X-100. The composition of the S/D mixture comprising Triton X-100 was prepared as described in Example 1 above. The composition of the S/D mixture comprising Brij C10 was prepared as follows.

The S/D components Polysorbate 80 (PS80, Crillet 4 HP, Tween 80) and Tri-n-butyl-phosphate (TnBP) were combined with the detergent Brij C10 in the following ratios (see Table 5):

TABLE 5

Amount of components for Brij C10 S/D Reagent Mix

| S/D Reagent | Amount to be combined for S/D Reagent Mix [g] |
| --- | --- |
| 20% (w/v) Brij C10 | 53.05 ± 0.53 |
| PS80 | 3.23 ± 0.03 |
| TnBP | 2.93 ± 0.03 |
| Resulting S/D reagent | 59.21 |

The mixture was stirred for at least 15 minutes. The S/D reagent mix was stored at room temperature for use within one year. Prior to use the S/D reagent mix was stirred again for at least 15 minutes to assure homogeneity.

The respective S/D reagent mixes were added to the IVIG-containing liquid to give a final concentration of 0.05% of the respective polyoxyethylene ether detergent.

Additionally, also inactivation of the virus BVDV was tested:

TABLE 6

Virus stocks used in the experiments.

| Virus Strain | Source | Propagated on Cell line | Source | Titrated on Cell line | Source |
| --- | --- | --- | --- | --- | --- |
| | | BVDV | | | |
| Nadl | ATCC[1] VR-1422 | MDBK | ATCC[1] CRL-22 | BT | ATCC[1] CRL-1390 |

Figure 3:
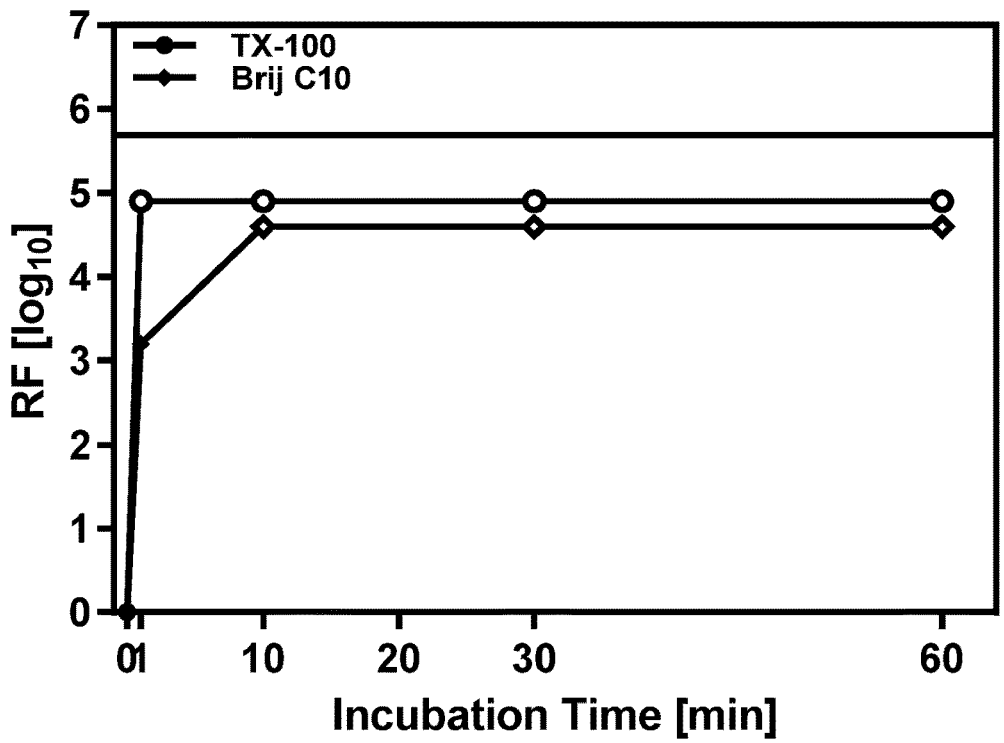
FIG. 3: Virus inactivation efficiency of low concentrations of Brij C10 in S/D treatment of IVIG-containing liquid at 17° C.±1° C. A three-component mixture was used to give final concentrations of 0.04%-0.06% Brij C10, 0.01%-
Figure 3:
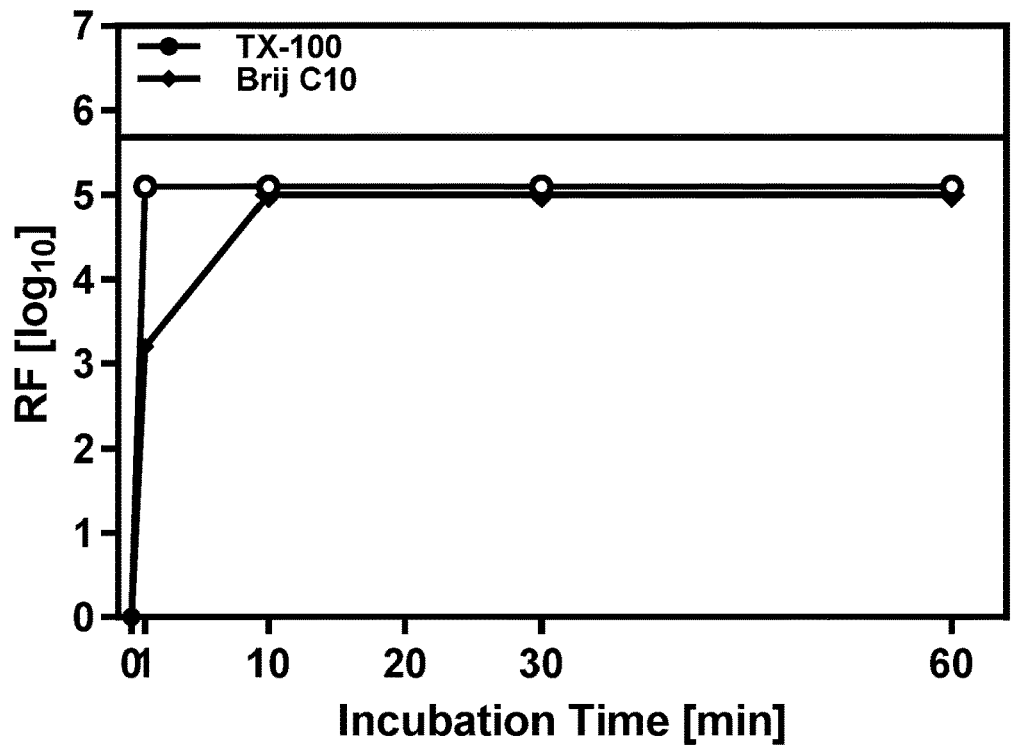

ATCC[1] American Type Culture Collection, 10801 University Boulevard, Manassas, VA 20110 USA Results When S/D treatment of an IVIG-containing liquid was performed using a mixture of Brij C10, PS80 and TnBP, HIV was inactivated by a virus reduction factor (RF) of over 4 within 10 minutes (FIG. 3A). Similar results were obtained in a repeat experiment (FIG. 3B).

In additional experiments, when S/D treatment of an IVIG-containing liquid was performed using a mixture of Brij C10, PS80 and TnBP, PRV was inactivated by a RF of around 4 within 10 minutes (FIG. 4A). Similar results were obtained in a repeat experiment (FIG. 4B).

In additional experiments, when S/D treatment of an IVIG-containing liquid was performed using a mixture of Brij C10, PS80 and TnBP, BVDV was inactivated by a RF of around 5 within 10 minutes (FIG. 5A). Similar results were obtained in a repeat experiment (FIG. 5B).

These experiments show that replacing Triton X-100 by Brij C10 for S/D treatment of biopharmaceutical drug-containing liquids results in efficient inactivation of lipid-enveloped viruses, even at low concentrations of detergent.

Example 3: X-MuLV and BVDV Inactivation Using Brij C10 in Liquids Comprising Human Serum Albumin The suitability of Brij C10 for S/D treatment to inactivate the lipid-enveloped viruses xenotropic murine leukemia virus (X-MuLV) and bovine viral diarrhea virus (BVDV) in liquids comprising human serum albumin (HSA) as a model protein for a biopharmaceutical drug was tested and compared to Triton X-100. To this end, virus was added to liquids comprising HSA. The virus-containing liquids comprising HSA were then incubated with S/D mixtures comprising low concentrations of Brij C10 for various time periods, and the remaining infectivity of the viruses was determined. Brij C10 was used at low concentrations in order to be able to evaluate the kinetics of virus inactions, i.e., the efficiency of virus inactivation (expressed by the RF) over time. As will be clear to a person skilled in the art, in commercial production processes such as biopharmaceutical production, Brij C10 can be used at significantly higher concentrations, which will accelerate the kinetics of virus inactivation and may also increase the achieved RF.

Materials

Liquid Comprising HSA

A human serum albumin (HSA)-containing liquid was used as a model for a liquid containing a biopharmaceutical drug.

Viruses

Xenotropic Murine Leukemia Virus (X-MuLV; Family Retroviridae; enveloped ssRNA virus; Ø=80-110 nm) was used as a model for endogenous retroviral particles and enveloped RNA viruses. Additionally, BVDV was used.

| | | Propagated on | | Titrated on | |
|---|---|---|---|---|---|
| Virus Strain | Source | Cell line | Source | Cell line | Source |
| X-MuLV | | | | | |
| pNFS Th-1 | ATCC[1] VR-1447 | M. dunni | ATCC[1] CRL-2017 | PG4 | ATCC[1] CRL-2032 |

ATCC[1] American Type Culture Collection, 10801 University Boulevard, Manassas, VA 20110 USA

TABLE 7

Virus stocks used in the experiments.

| | | Propagated on | | Titrated on | |
|---|---|---|---|---|---|
| Virus Strain | Source | Cell line | Source | Cell line | Source |
| BVDV | | | | | |
| NadI | ATCC[1] VR-1422 | MDBK | ATCC[1] CRL-22 | BT | ATCC[1] CRL-1390 |

ATCC[1] American Type Culture Collection, 10801 University Boulevard, Manassas, VA 20110 USA Virus stocks were characterized prior to use. This characterization included the determination of the virus titer by at least ten independent titrations and specification of an acceptance virus titer range for use as positive control, the determination of virus stock protein content, PCR tests for virus identity and contamination with other viruses and *mycoplasma* and tests for virus aggregation with filters not allowing the passage of large virus aggregates. Only virus stocks passing PCR identity/contamination tests with no significant aggregation, (i.e. difference in infectivity titers between virus stock and filtered stock was smaller than 1.0 log) were used.

Brij C10 Reagent Mix

The S/D components Polysorbate 80 (PS80, Crillet 4 HP, Tween 80) and Tri-n-butyl-phosphate (TnBP) were combined with the respective detergent (i.e. Triton X-100 or Brij C10) in the following ratio (see Table 8 to Table 9):

TABLE 8

Amount of components for Triton X-100 S/D Reagent Mix

| S/D Reagent | Amount to be combined for S/D Reagent Mix [g] |
|---|---|
| Triton X-100 | 10.5 ± 0.1 |
| PS80 | 3.2 ± 0.03 |
| TnBP | 2.9 ± 0.03 |
| Resulting S/D reagent | 16.6 |

TABLE 9

Amount of components for Brij C10 S/D Reagent Mix

| S/D Reagent | Amount to be combined for S/D Reagent Mix [g] |
|---|---|
| 20% (w/v) Brij C10 | 52.5 ± 0.5 |
| PS80 | 3.2 ± 0.03 |
| TnBP | 2.9 ± 0.03 |
| Resulting S/D reagent | 58.6 |

Each mixture was stirred for at least 15 minutes. The S/D reagent mixes were stored at room temperature for use within one year. Prior to use the respective S/D reagent mix were stirred again for at least 15 minutes to assure homogeneity.

Methods

The virus inactivation capacity and the robustness of the S/D treatment were evaluated under conditions unfavorable for virus inactivation, i.e. with short incubation times and at relatively low temperatures. As will be clear to a person skilled in the art, in commercial production processes such as biopharmaceutical production, longer incubation times and higher temperatures can be used, which will accelerate the kinetics of virus inactivation and may also increase the achieved LRV. Further, as already mentioned above, low concentrations of S/D components were used. As will be clear to a person skilled in the art, in commercial production processes such as biopharmaceutical production, higher concentrations of S/D components can be used, which will accelerate the kinetics of virus inactivation and may also increase the achieved LRV.

Since the protein concentration has no significant impact on virus inactivation during S/D treatment (see also Dichtelmüller et al., 2009), the robustness concerning protein content was not investigated.

All following steps took place in a biosafety class II cabinet. The starting material was incubated under stirring at a temperature of +1° C.±1° C. using a double-walled vessel connected to a cryostat for incubation. The HSA-containing liquid was then filtered through a 0.2 μm PVDF membrane syringe filter (a hydrophilic PVDF filter, Millipak 60 or equivalent). After filtration, the temperature and the volume were measured.

The filtered HSA-containing liquid was again adjusted under stirring to +1° C.±1° C. using a double-walled vessel connected to a cryostat. This temperature range was maintained under stirring until the end of the incubation of the filtered HSA-containing liquid with the S/D reagents and was recorded continuously. The determined volume of the filtered HSA-containing liquid, transferred to a screw-cap flask of which the tare weight has been determined, was spiked at a ratio of 1:31, e.g. 48 mL HSA-containing liquid were spiked with 1.6 mL of virus stock solution. The spiked HSA-containing liquid was further incubated under continued stirring at 1° C.±1° C. Within 1-2 minutes after spiking, samples for virus titration (0.5 mL Spike Control, SC, and 2 mL Hold Control, HC) were taken.

After drawing the Hold Control (HC) was kept at the same temperature, i.e. at +1° C.±1° C., as the spiked HSA-containing liquid after addition of S/D reagents, i.e. it was stored in the same cooling circle as the vessel with the HSA-containing liquid, until the end of S/D treatment. The temperature of the cooling liquid was determined before insertion of the Hold Control sample and, again, shortly before the Hold Control was removed for titration after S/D treatment.

The weight of the spiked HSA-containing liquid was determined for calculation of the amount of the S/D reagent mix to be added. The weighed material was re-adjusted, if necessary, under stirring to +1° C.±1° C. The respective S/D reagent mix was added to the HSA-containing liquid to give a final concentration of 0.08% to 0.1% (w/w) of the respective polyoxyethylene ether detergent. The S/D reagent mix was added under stirring within 1 minute using a syringe, and the actual amount of S/D reagent mix added was determined by back-weighing the syringe. The spiked HSA-containing liquid was further incubated with S/D reagents under continued stirring at +1° C.±1° C. for 59±1 minutes. During incubation, 1 mL samples for virus titration were taken after 1-2 min, 10±1 min, 30±1 min and 59±1 min. To prevent further inactivation of virus by the S/D reagents following sample drawing, the samples were diluted immediately 1:20 with cold (+2° C. to +8° C.) cell culture medium (i.e. 1 volume of sample plus 19 volumes of cell culture medium).

Titration of the samples and calculation of the virus clearance capacity was performed as described for Example 1 above.

Results

When S/D treatment of a HSA-containing liquid was performed at 1° C.±1° C. using a mixture of Brij C10, PS80 and TnBP, X-MuLV was inactivated by a virus reduction factor (RF) of over 2 within 60 minutes (FIG. 6A). Similar results were obtained in a repeat experiment (FIG. 6B).

In additional experiments, when S/D treatment of a HSA-containing liquid was performed at 1° C.±1° C. using a mixture of Brij C10, PS80 and TnBP, BVDV was inactivated by a virus reduction factor (RF) of around 4 within 10 minutes (FIG. 7A). Similar results were obtained in a repeat experiment (FIG. 7B).

Additional experiments were performed exactly as described in the Materials and Methods section of this Example, only that S/D treatment of the HSA-containing liquid was performed at 19° C.±1° C. instead of 1° C.±1° C. When S/D treatment of a HSA-containing liquid was performed at 19° C.±1° C. using a mixture of Brij C10, PS80 and TnBP (Brij C10), X-MuLV was inactivated by a virus reduction factor (RF) of over 3 within 10 minutes (FIG. 8A). Similar results were obtained in a repeat experiment (FIG. 8B).

These experiments show that replacing Triton X-100 by Brij C10 for S/D treatment of biopharmaceutical drug-containing liquids results in efficient inactivation of lipid-enveloped viruses at or around room temperature and at temperatures as low as 1° C.±1° C., even at low concentrations of the detergents.

Example 4: Synthesis of 4-tert-octylbenzyl alcohol polyethoxylate I (Method 1)

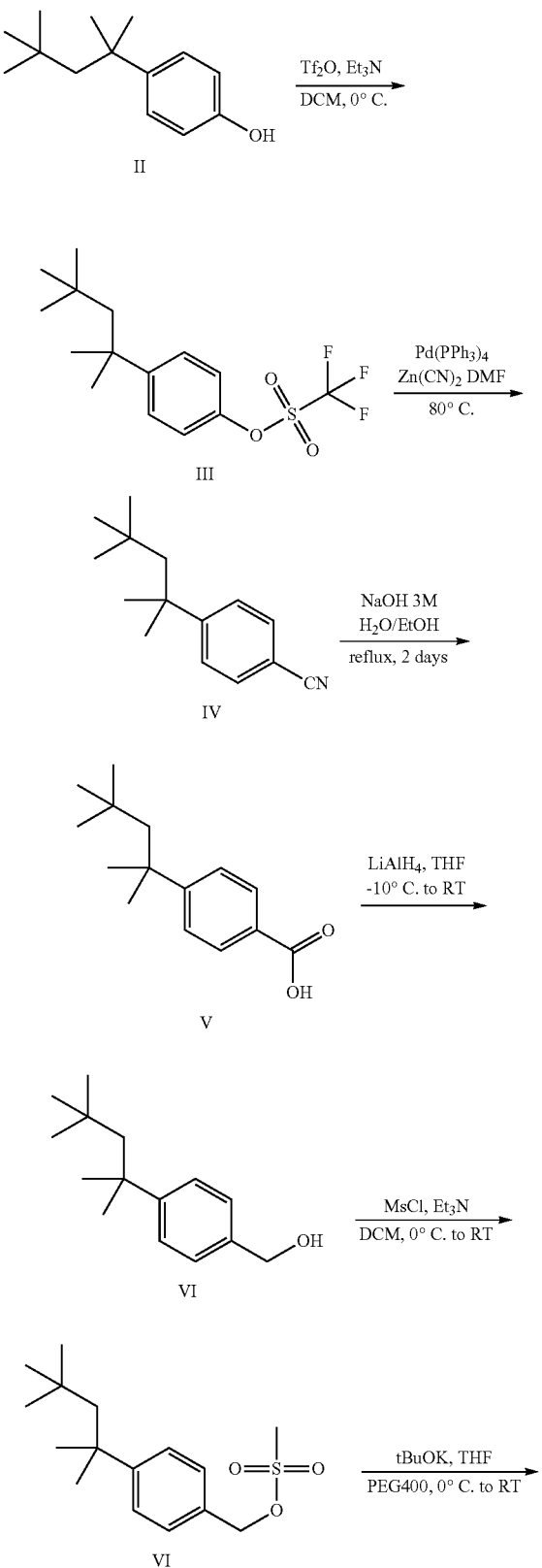

-continued

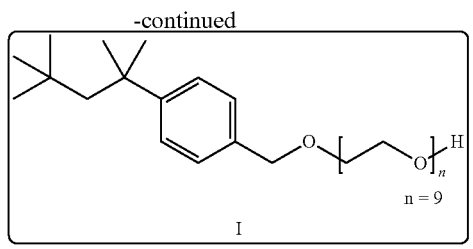

I

Synthesis of Intermediate III:

Phenol II (170.3 g, 800 mmol) was placed in a 3 neck 2 L flask equipped with an inner thermometer and stirring bar. Anhydrous $CH_2Cl_2$ (1000 mL) was added to the flask and stirring was started. After dissolution of the starting material the solution was cooled to 0° C. After total dissolution $NEt_3$ (225 mL, 1.6 mol) was added within 10 min. A solution $Tf_2O$ (256 g, 907 mmol) in $CH_2Cl_2$ (180 mL) was added at 0° C. to the reaction mixture over 120 min and the reaction was stirred overnight at room temperature. An aqueous saturated $NaHCO_3$ solution (400 mL) was added and the reaction mixture was extracted. The organic phase was washed repeatedly with water (2×400 mL) and brine (500 mL). The organic phase was then concentrated in vacuo. Toluene (300 mL) was added to the residue and the crude product was concentrated to yield 314 g of crude black liquid. This residue was charged on top of a $SiO_2$ plug and eluted with petroleum ether/EtOAc (0 to 2%). Concentration of the pure fractions yielded 269.5 g (Yield: 99.6%) of a clear colorless oil. $R_f$=0.74 (petroleum ether/EtOAc 5%).

Synthesis of Intermediate IV:

Triflate III (269 g, 795 mmol) was dissolved in anhydrous and degassed DMF (1.3 L) and $Zn(CN)_2$ (95.3 g, 795 mmol) and $Pd(PPh_3)_4$ (25 g, 21.5 mmol) were added sequentially. The reaction mixture was warmed to 80° C. for 3 hrs followed by removal of the DMF under vacuum. Toluene (300 mL) was added to the residue and the crude product was concentrated to yield 432 g of black residue. This crude product was charged on top of a $SiO_2$ plug and eluted with petroleum ether/EtOAc (0 to 10%). Concentration of the pure fractions yielded 128.1 g (Yield: 74.8%) of a clear colorless oil. $R_f$=0.23 (petroleum ether/EtOAc 2%).

Synthesis of Intermediate V:

Nitrile IV (127.6 g. 592.5 mmol) dissolved in MeOH (500 mL), aqueous NaOH 4M (750 mL) was added and the mixture was brought to reflux and kept at this temperature (80° C.) overnight. An additional aqueous NaOH 10M (150 mL) was added to the warm mixture and the solution was heated further for 20 hrs. After cooling to ambient temperature the content of the reaction vessel was transferred into a large Beaker and cooled in an ice bath. Aqueous HCl 4M (1.1 L) was added within 30 min, at this point the pH was acidic as indicated by pH paper and a white solid had precipitated. The precipitate was filtered and rinsed with water (500 mL). The wet cake was transferred to a 2 L flask and dried under vacuum for 3 days to yield 127.5 g (Yield: 91.9%) of a white powder. $R_f$=0.42 (petroleum ether/EtOAc 2:1).

Synthesis of Intermediate VI:

Carboxylic acid V (127 g, 542 mmol) was suspended in dried mTHF (1.2 L) and cooled to −10° C. A solution of $LiAH_4$ in THE (1 M, 575 mL, 575 mmol) was added over 60 min, then the reaction was warmed slowly to ambient temperature and further stirred overnight. The content of the reaction vessel was transferred into a large Beaker and the excess of hydride was carefully quenched with ice (15 g). Aqueous HCl 3M (500 mL) was added within 20 min, at this point the pH was acidic as indicated by pH paper. EtOAc (300 mL) was added to the crude mixture and the 2 phases were vigorously agitated. The aqueous phase was back extracted twice with EtOAc (300 mL and 500 mL). The combined organic phases were washed successively with an aqueous saturated $NaHCO_3$ solution (300 mL), water (300 mL) and brine (500 mL). The organic phase was then concentrated in vacuo. Toluene (300 mL) was added to the residue and the crude product was concentrated to yield 123.3 g of a clear yellowish oil. This residue was charged on top of a $SiO_2$ plug and eluted with petroleum ether/EtOAc (0 to 15%). Concentration of the pure fractions yielded 85.3 g (Yield: 71.4%) of an amorphous white solid. $R_f$=0.37 (petroleum ether/EtOAc 4:1).

Synthesis of Intermediate VII:

Benzyl alcohol VI (84.8 g, 385 mmol) was dissolved in anhydrous $CH_2Cl_2$ (1 L) and cooled in an ice/water bath. $NEt_3$ (110 mL, 770 mmol) was added followed by the slow addition of a solution of MsCl (45 mL, 577 mmol) in anhydrous $CH_2Cl_2$ (25 mL) over 60 min. The reaction warmed slowly to ambient temperature and was further stirred overnight. An aqueous saturated $NaHCO_3$ solution (420 mL) was added and the reaction mixture was agitated vigorously. The organic phase was washed repeatedly with water (2×500 mL) and brine (300 mL). The organic phase was then concentrated in vacuo. Toluene (200 mL) and $CH_2C2$ (100 mL) were added to the residue and the crude product was concentrated to yield 90 g (Yield: 78.4%) of an orange semi solid. $R_f$=0.71 (petroleum ether/EtOAc 4:1).

Synthesis of I:

PEG400 (360 g, 900 mmol) was dissolved in anhydrous THE (1 L) and tBuOK (90 g, 802 mmol) was added at ambient temperature portion wise over 15 min and the mixture was stirred 60 min at ambient temperature and cooled in an ice bath. In the meantime, Mesylate VII (89.5 g, 300 mmol) was suspended in THE (300 mL) and the milky orange solution was added to the cooled deprotonated PEG400 solution over 20 min. The reaction was warmed slowly to ambient temperature and further stirred overnight. Ice (500 g) was added as well as aqueous HCl 1M (820 mL). The THF was removed under vacuum and EtOAc (1 L) was added. The phases were agitated and the organic phase was washed successively with water (2×500 mL). Each aqueous phase was back extracted with EtOAc (300 mL). The combined organic phases were washed with water (500 ml) and concentrated in vacuuo. Toluene (250 mL) was added to the residue and the crude product was concentrated to yield 125.2 g of a clear yellowish oil. This residue was charged on top of a $SiO_2$ plug and eluted with $CH_2Cl_2$/MeOH (0 to 8%). Concentration of the pure fractions yielded 107.5 g (Yield: 59.5%) of a light brown clear oil. $R_f$=0.37-0.22 ($CH_2Cl_2$/MeOH 20:1). MS (ESI): m/z=$[M+H]^+$=573.5, 617.5 (100%), 661.6; $[M+Ac]^-$=631.4, 675.4 (100%), 719.5. $^1$H-NMR (600 MHz, $CDCl_3$): δ=7.33 (d, J=8.3 Hz, 2H), 7.23 (d, J=8.3 Hz, 2H), 4.52 (s, 2H), 3.72-3.58 (m, 33H), 2.54 (br s, 1H), 1.72 (s, 2H), 1.34 (s, 6H), 0.70 (s, 9H). $^{13}$C-NMR (150 MHz, $CDCl_3$): δ=149.7, 135.1, 127.4 (2C), 126.2 (2C), 73.2, 72.6, 70.7 (m), 70.5, 69.4, 61.9, 57.0, 38.6, 32.5, 31.9 (3C), 31.6 (2C).

Example 5a: Synthesis of 4-tert-octylbenzyl alcohol polyethoxylate I (Method 2)

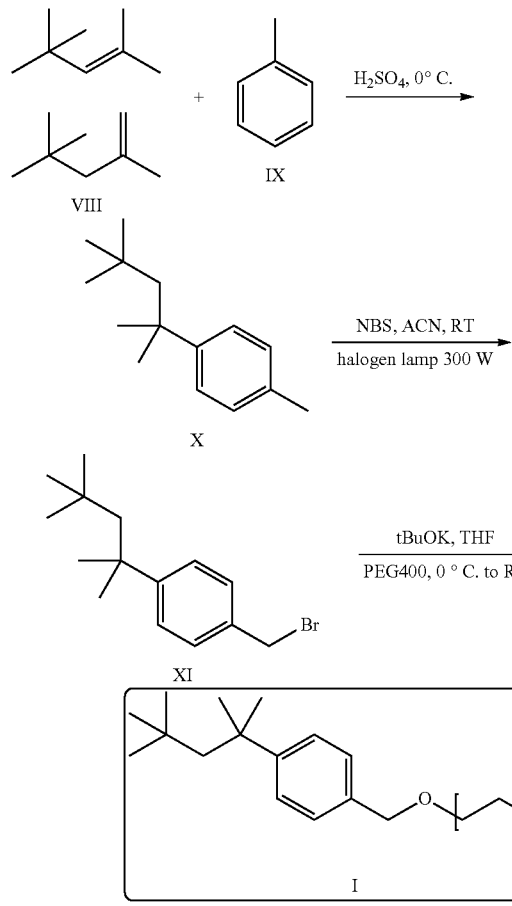

Toluene (35 mL, 328 mmol) and concentrated H$_2$SO$_4$ (10 mL) were cooled to 0° C. in a round bottom flask. A mixture of toluene (27 mL, 256 mmol) and Diisobutylene (as a mixture 3:1 2,4,4-trimethyl-1-pentene+2,4,4-trimethyl-2-pentene, 10 mL, 64 mmol) was added slowly to the reaction mixture over 2 hrs. The reaction was further stirred at 0° C. for 2 hrs. Water (100 mL) was added. After phase separation the organic phase was washed with an aqueous saturated NaHCO$_3$ solution (100 mL), dried over MgSO$_4$ and concentrated to yield 14 g of a clear colorless oil. The oil was placed in a 100 mL round bottom flask and distillated over a short path distillation apparatus (1·10$^{-1}$ mbar). The fraction (8.1 g, Yield 61.9%) that distillated between 62 and 70° C. was collected. R$_f$=0.65 (Petrol ether 40-60 100%).

p-Substituted toluene X (500 mg, 2.45 mmol) was dissolved in Acetonitrile (ACN) (5 mL). N-bromosuccinimide (NBS) (460 mg, 2.57 mmol) was added and after dissolution, the Duran 25 mL round bottom flask was placed 15 cm away from the halogen lamp (300 W). After 60 min of irradiation (Reaction temperature=45° C.) the solvent was removed. Petrol ether 40-60 (25 mL) was added and a solid precipitated. The liquid phase was washed with water (2×20 mL), dried over MgSO$_4$ and concentrated to yield 540 mg (Yield: 77.9%) of a crude yellowish oil. R$_f$=0.43 (Petrol ether 40-60100%).

PEG400 (2.25 g, 5.61 mmol) was dissolved in anhydrous THF (5 mL) at ambient temperature. tBuOK (420 mg, 3.74 mmol) was added portion wise over 1 min and the mixture was stirred 90 min and then cooled to 0° C. in an ice/water bath. In the meantime, the benzyl bromide intermediate XI (530 mg, 1.87 mmol) was suspended in THF (2 mL) and the solution was added to the cooled deprotonated PEG400 solution. The reaction was warmed slowly to ambient temperature and further stirred overnight. HCl (1M, 20 mL) was added to the reaction mixture as well as EtOAc (50 mL) and water (20 mL). The solution was transferred into a separatory funnel and extracted vigorously. After phase separation the organic phase was washed successively with water (5×15 mL) and finally dried over MgSO$_4$ to yield 0.8 g of crude oily residue. This residue was charged on top of a SiO$_2$ column and eluted with CH$_2$Cl$_2$/MeOH (0 to 8%). Concentration of the pure fractions yielded 588 mg (Yield: 52.2%) of a clear yellowish oil. R$_f$=0.37-0.22 (CH$_2$Cl$_2$/MeOH 20:1).

Example 5b: Synthesis of 4-tert-octylbenzyl alcohol polyethoxylate I (Method 2 Variants)

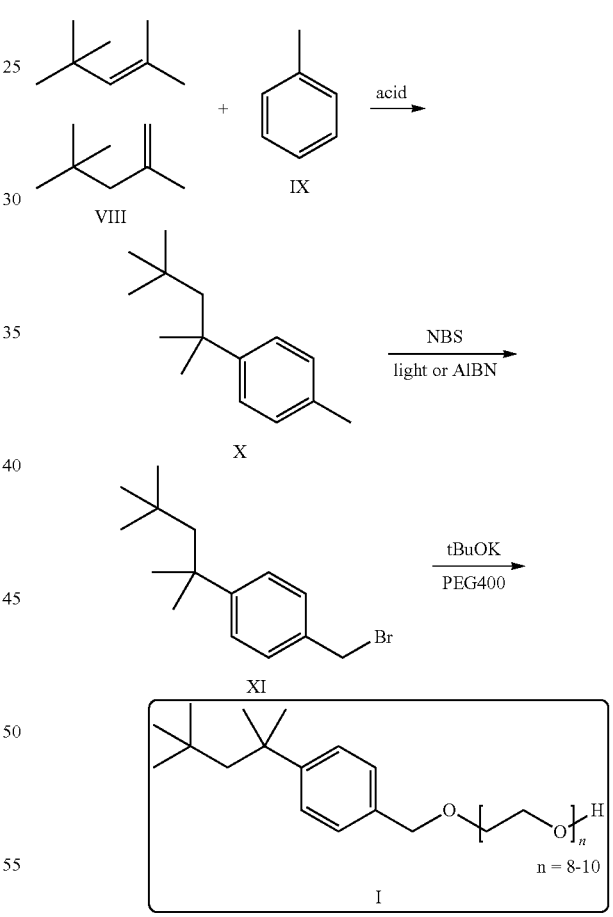

Step 1:

This step was carried out as follows:

Toluene (750 mL, 7.04 mol) and concentrated H$_2$SO$_4$ (20 mL, 0.375 mol) were cooled to 0° C. in a round bottom flask. A mixture of toluene (250 mL, 2.35 mol) and diisobutylene (as a mixture 3:1 2,4,4-trimethyl-1-pentene+2,4,4-tri methyl-2-pentene, 200 mL, 1.28 mol) was added slowly to the reaction mixture over 90 min. The reaction was further stirred at 0° C. and warmed to ambient temperature overnight. Ice (400 g) was added and the mixture was transferred to a separatory funnel. After phase separation the organic phase was washed successively with an aqueous saturated NaHCO₃ solution (300 mL) and water (2×250 mL). The organic phase was concentrated to yield 199.1 g of a clear colorless oil. The oil was placed in a 500 mL round bottom flask and distillated over a short path distillation apparatus (20 mbar). The fractions that distillated between 138° C. and 161° C. were collected (134.1 g, Yield 51.4%). $R_f$=0.65 (Petrol ether 40-60 100%). ¹H-NMR (600 MHz, CDCl₃): δ=7.28 (d, J=8.2 Hz, 2H), 7.10 (d, J=8.2 Hz, 2H), 2.34 (s, 3H), 1.75 (s, 2H), 1.38 (s, 6H), 0.75 (s, 9H). ¹³C-NMR (150 MHz, CDCl₃): δ=147.3, 134.7, 128.6 (2C), 126.1 (2C), 57.1, 38.4, 32.5, 31.9 (3C), 31.7 (2C), 21.0.

Alternatively, this step was carried out as follows:

Toluene (400 mL, 3.83 mol) and nonafluoro-1-butanesulfonic acid (4 mL, 24 mmol) were stirred at ambient temperature in a round bottom flask. A mixture of toluene (200 mL, 1.92 mol) and diisobutylene (as a mixture 3:1 2,4,4-trimethyl-1-pentene+2,4,4-trimethyl-2-pentene, 100 mL, 0.64 mol) was added slowly to the reaction mixture over 60 min. The reaction was further stirred at ambient temperature overnight. Aqueous saturated NaHCO₃ solution (200 mL) was added and the mixture was stirred for 20 min. The mixture was transferred to a separatory funnel and the aqueous phase was discarded. The organic phase was washed successively with water (3×300 mL). The organic phase was concentrated to yield 132.5 g of a clear colorless oil. The oil was placed in a 500 mL round bottom flask and distillated over a short path distillation apparatus (26-16 mbar). The fractions that distillated between 115° C. and 135° C. were collected (80.5 g, Yield 62%). $R_f$=0.65 (Petrol ether 40-60 100%). ¹H-NMR (600 MHz, CDCl₃): δ=7.28 (d, J=8.2 Hz, 2H), 7.10 (d, J=8.2 Hz, 2H), 2.34 (s, 3H), 1.75 (s, 2H), 1.38 (s, 6H), 0.75 (s, 9H). ¹³C-NMR (150 MHz, CDCl₃): δ=147.3, 134.7, 128.6 (2C), 126.1 (2C), 57.1, 38.4, 32.5, 31.9 (3C), 31.7 (2C), 21.0.

Step 2:

This step was carried out as follows:

p-Substituted toluene X (63.6 g, 311 mmol) was dissolved in Acetonitrile (ACN) (650 mL). N-bromosuccinimide (NBS) (58.2 g, 327 mmol) was added and after dissolution, the Duran 2 L round bottom flask was placed 5-25 cm away from the halogen lamp (300 W) while stirring (350 rpm). After 6 hrs of irradiation (Reaction temperature=up to 46° C.) the solvent was removed under vacuo. Petrol ether 40-60 (450 mL) was added and a dark solid precipitated. The liquid phase was concentrated to yield a dark brown residue (75 g). This residue was charged on top of a SiO₂ plug and eluted with petrol ether 40-60 (100%). Concentration of the pure fractions yielded 43.8 g (Yield: 49.7%) of an orange clear oil. $R_f$=0.43 (Petrol ether 40-60 100%). ¹H-NMR (600 MHz, CDCl₃): δ=7.34 (d, J=8.4 Hz, 2H), 7.30 (d, J=8.4 Hz, 2H), 4.50 (s, 2H), 1.74 (s, 2H), 1.36 (s, 6H), 0.72 (s, 9H). ¹³C-NMR (150 MHz, CDCl₃): δ=150.9, 134.8, 128.6 (2C), 126.7 (2C), 57.0, 38.7, 33.9, 32.5, 31.9 (3C), 31.6 (2C).

Alternatively, this step was carried out as follows:

p-Substituted toluene X (85.2 g, 417 mmol) was dissolved in Trifluorotoluene (830 mL). Other solvents such as esters or alkanes (EtOAc and hexane) are also effective. N-bromosuccinimide (NBS) (74.2 g, 417 mmol) was added as well as AIBN (Azobis(isobutyronitrile) (3.4 g, 21 mmol) while stirring (450 rpm). The mixture was heated to 80° C. for 5 hours. The solvent was removed under vacuo. Petrol ether 40-60 (350 mL) was added and a white solid precipitated. The liquid phase was concentrated to yield a clear orange residue (108 g). This residue was charged on top of a SiO₂ plug and eluted with petrol ether 40-60 (100%). Concentration of the pure fractions yielded 64.1 g (Yield: 54.3%) of a clear almost colorless oil that crystallized to form colorless needles, indicating high purity of the product. $R_f$=0.43 (Petrol ether 40-60 100%). 1H-NMR (600 MHz, CDCl₃): δ=7.34 (d, J=8.4 Hz, 2H), 7.30 (d, J=8.4 Hz, 2H), 4.50 (s, 2H), 1.74 (s, 2H), 1.36 (s, 6H), 0.72 (s, 9H). ¹³C-NMR (150 MHz, CDCl₃): δ=150.9, 134.8, 128.6 (2C), 126.7 (2C), 57.0, 38.7, 33.9, 32.5, 31.9 (3C), 31.6 (2C). It is expected that the use of AIBN (Azobis(isobutyronitrile) as a radical initiator contributes to the high purity of the product which is obtained in this reaction step.

Step 3:

This step was carried out as follows:

PEG400 (184.1 g, 460 mmol) was dissolved in anhydrous THE (550 mL) at ambient temperature. tBuOK (27.2 g, 245 mmol) was added portionwise over 15 min and the mixture was stirred 90 min. In the meantime, the benzyl bromide intermediate XI (43.5 g, 153 mmol) was suspended in THE (300 mL) and the solution was added to the cooled deprotonated PEG400 solution. The reaction was stirred overnight at ambient temperature. HCl (1M, 270 mL) was added to the reaction mixture. Volatiles were removed and EtOAc (600 mL) was added. The solution was transferred into a separatory funnel and extracted vigorously. After phase separation the aqueous phase was further extracted with EtOAc (300 mL). The combined organic phases were washed successively with water/brine (1:1, 3×300 mL) and finally concentrated to yield 90.4 g of crude orange oily residue. This residue was charged on top of a SiO₂ column and eluted with CH₂Cl₂/MeOH (0 to 8%). Concentration of the pure fractions yielded 82.2 g (Yield: 89.0%) of a clear light brown oil. $R_f$=0.37-0.22 (CH₂C2/MeOH 20:1). MS (ESI): m/z= [M+H]⁺=573.5, 617.5 (100%), 661.6; [M+Ac]⁻=631.4, 675.4 (100%), 719.5. ¹H-NMR (600 MHz, CDCl₃): δ=7.33 (d, J=8.3 Hz, 2H), 7.23 (d, J=8.3 Hz, 2H), 4.52 (s, 2H), 3.72-3.58 (m, 33H), 2.54 (br s, 1H), 1.72 (s, 2H), 1.34 (s, 6H), 0.70 (s, 9H). ¹³C-NMR (150 MHz, CDCl₃): δ=149.7, 135.1, 127.4 (2C), 126.2 (2C), 73.2, 72.6, 70.7 (m), 70.5, 69.4, 61.9, 57.0, 38.6, 32.5, 31.9 (3C), 31.6 (2C).

Alternatively, this step was carried out as follows:

PEG400 (475 g, 1.19 mol) was dissolved in TBME (methyl-tert-butylether) (1.0 L) at ambient temperature. tBuOK (43.2 g, 385 mmol) was added portion wise over 20 min and the mixture was stirred 90 min. In the meantime, the benzyl bromide intermediate XI (84 g, 297 mmol) was suspended in TBME (250 mL) and the solution was added to the deprotonated PEG400 solution at ambient temperature. The reaction was stirred 3 hrs at ambient temperature. Ice (200 g) and HCl (1M, 400 mL) were added to the reaction mixture. The solution was transferred into a separatory funnel and EtOAc (1 L) and water (500 mL) were added and extracted vigorously. After phase separation the organic phase was washed successively with water/brine (1:1, 3×500 mL) and finally concentrated to yield 165 g of crude orange oily residue. This residue was charged on top of a SiO₂ column and eluted with CH₂Cl₂/MeOH (0 to 10%). Concentration of the pure fractions yielded 151.7 g (Yield: 84.9%) of a clear light brown oil. $R_f$=0.37-0.22 (CH₂Cl₂/MeOH 20:1). MS (ESI): m/z=[M+H]+=573.5, 617.5 (100%), 661.6; [M+Ac]⁻=631.4, 675.4 (100%), 719.5. ¹H-NMR (600 MHz, CDCl₃): δ=7.33 (d, J=8.3 Hz, 2H), 7.23 (d, J=8.3 Hz, 2H), 4.52 (s, 2H), 3.72-3.58 (m, 33H), 2.54 (br s, 1H), 1.72 (s, 2H), 1.34 (s, 6H), 0.70 (s, 9H). ¹³C-NMR (150 MHz, CDCl₃): δ=149.7, 135.1, 127.4 (2C), 126.2 (2C), 73.2, 72.6, 70.7 (m), 70.5, 69.4, 61.9, 57.0, 38.6, 32.5, 31.9 (3C), 31.6 (2C). It is expected that the use of TBME (methyl-tert-butylether) as a solvent, the moderate reaction time of 3 hours (which is expected to minimize reaction side products), the larger manufacturing scale and the purity of the starting material (i.e. the benzyl bromide intermediate XI) all contribute to the high yield observed in this reaction step.

Example 6: PRV Inactivation Using 4-Tert-Octylbenzyl Alcohol Polyethoxylate in Liquids Comprising Intravenous Immunoglobulin Materials and Methods The experiments were performed as described for Example 1 above. However, for the S/D treatment an S/D mixture comprising the 4-tert-octylbenzyl alcohol polyethoxylate produced in Example 5a was tested and compared to an S/D mixture comprising Triton X-100. The composition of the S/D mixture comprising Triton X-100 was prepared as described in Example 1 above. The composition of the S/D mixture comprising 4-tert-octylbenzyl alcohol polyethoxylate was prepared as follows.

The S/D components Polysorbate 80 (PS80, Crillet 4 HP, Tween 80) and Tri-n-butyl-phosphate (TnBP) were combined with the detergent 4-tert-octylbenzyl alcohol polyethoxylate produced in Example 5a in the following ratios (see Table 10):

TABLE 10

Amount of components for 4-tert-octylbenzyl alcohol polyethoxylate (abbreviated as "4-TOBAPE") S/D Reagent Mix

| S/D Reagent | Amount to be combined for S/D Reagent Mix [g] |
|---|---|
| 4-TOBAPE | 10.61 ± 0.11 |
| PS80 | 3.23 ± 0.03 |
| TnBP | 2.93 ± 0.03 |
| Resulting S/D reagent | 16.77 |

T|4-TOBAPE as stirred for at least 15 minutes. The S/D reagent mix was stored at room temperature for use within one year. Prior to use the S/D reagent mix was stirred again for at least 15 minutes to assure homogeneity.

The respective S/D reagent mixes were added to the IVIG-containing liquid to give a final concentration of 0.05% w/w of the respective polyoxyethylene ether detergent.

Only inactivation of the virus PRV was tested.

Results

When S/D treatment of an IVIG-containing liquid was performed using a mixture of 4-tert-octylbenzyl alcohol polyethoxylate, PS80 and TnBP, PRV was inactivated by a virus reduction factor (RF) of around 4 within 1-2 minutes (FIG. 9A). Similar results were obtained in a repeat experiment (FIG. 9B).

These experiments show that replacing Triton X-100 by 4-tert-octylbenzyl alcohol polyethoxylate for S/D treatment of biopharmaceutical drug-containing liquids results in efficient inactivation of lipid-enveloped viruses, even at low concentrations of detergent.

Example 7: X-MuLV Inactivation Using 4-Tert-Octylbenzyl Alcohol Polyethoxylate in Liquids Comprising Human Serum Albumin Materials and Methods The experiments were performed as described for Example 3 above. However, for the S/D treatment an S/D mixture comprising 4-tert-octylbenzyl alcohol polyethoxylate was tested and compared to an S/D mixture comprising Triton X-100. The composition of the S/D mixture comprising Triton X-100 was prepared as described in Example 3 above. The composition of the S/D mixture comprising 4-tert-octylbenzyl alcohol polyethoxylate was prepared as follows.

The S/D components Polysorbate 80 (PS80, Crillet 4 HP, Tween 80) and Tri-n-butyl-phosphate (TnBP) were combined with the detergent 4-tert-octylbenzyl alcohol polyethoxylate in the following ratios (see Table 11):

TABLE 11

Amount of components for 4-tert-octylbenzyl alcohol polyethoxylate (abbreviated as "4-TOBAPE") S/D Reagent Mix

| S/D Reagent | Amount to be combined for S/D Reagent Mix [g] |
|---|---|
| 4-TOBAPE | 10.5 ± 0.1 |
| PS80 | 3.2 ± 0.03 |
| TnBP | 2.9 ± 0.03 |
| Resulting S/D reagent | 16.6 |

The mixture was stirred for at least 15 minutes. The S/D reagent mix was stored at room temperature for use within one year. Prior to use the S/D reagent mix was stirred again for at least 15 minutes to assure homogeneity.

The respective S/D reagent mixes were added to the HSA-containing liquid to give a final concentration of 0.1% of the respective polyoxyethylene ether detergent.

Only inactivation of the virus X-MuLV was tested.

Results

When S/D treatment of a HSA-containing liquid was performed at 1° C.±1° C. using a mixture of for 4-tert-octylbenzyl alcohol polyethoxylate, PS80 and TnBP, X-MuLV was inactivated by a virus reduction factor (RF) of over 2 within 10 minutes (FIG. 10A). Similar results were obtained in a repeat experiment (FIG. 10B).

Additional experiments were performed exactly as described in the Materials and Methods section of this Example, only that S/D treatment of the HSA-containing liquid was performed at 19° C.±1° C. instead of 1° C.±1° C. When S/D treatment of a HSA-containing liquid was performed at 19° C.±1° C. using a mixture of for 4-tert-octylbenzyl alcohol polyethoxylate, PS80 and TnBP, X-MuLV was inactivated by a virus reduction factor (RF) of over 2 within 10 minutes (FIG. 11A), and by a RF of around 4 within 30 min. Similar results were obtained in a repeat experiment (FIG. 11B).

These experiments show that replacing Triton X-100 by for 4-tert-octylbenzyl alcohol polyethoxylate for S/D treatment of biopharmaceutical drug-containing liquids results in efficient inactivation of lipid-enveloped viruses at or around room temperature and at temperatures as low as 1° C.±1° C., even at low concentrations of the detergents.

Example 8: BVDV Inactivation Using 4-Tert-Octylbenzyl Alcohol Polyethoxylate, Triton X-100 Reduced or Brij C10 in Buffer Containing HSA The suitability of 4-tert-octylbenzyl alcohol polyethoxylate, Triton X-100 reduced or Brij C10 for single-detergent treatment to inactivate the lipid-enveloped virus bovine viral diarrhea virus (BVDV) in a buffer containing human serum albumin (HSA) as a model protein for a therapeutic antibody was tested and compared to Triton X-100. To this end, low concentrations of the respective detergent were added to a buffer containing HSA, and the mixture was then spiked with virus. Following incubation for various time periods the remaining infectivity of the virus was determined. The respective detergents were used at low concentrations in order to be able to evaluate the kinetics of virus inactivation, i.e., the efficiency of virus inactivation (expressed by the RF) over time. As will be clear to a person skilled in the art, in commercial production processes such as biopharmaceutical production, the detergents of the invention can be used at significantly higher concentrations, which will accelerate the kinetics of virus inactivation and may also increase the achieved RF.

Materials

Buffer Containing HSA

A buffer containing human serum albumin (HSA) was used as a model for a therapeutic antibody.

TABLE 12

Virus stock used in the experiments.

| | | Propagated on | | Titrated on | |
|---|---|---|---|---|---|
| Virus Strain | Source | Cell line | Source | Cell line | Source |
| BVDV | | | | | |
| Nadl | ATCC[1] VR-1422 | MDBK | ATCC[1] CRL-22 | BT | ATCC[1] CRL-1390 |

ATCC[1] American Type Culture Collection, 10801 University Boulevard, Manassas, VA 20110 USA Virus stocks were characterized prior to use. This characterization included the determination of the virus titer by at least ten independent titrations and specification of an acceptance virus titer range for use as positive control, the determination of virus stock protein content, PCR tests for virus identity and contamination with other viruses and *mycoplasma* and tests for virus aggregation with filters not allowing the passage of large virus aggregates. Only virus stocks passing PCR identity/contamination tests with no significant aggregation, (i.e. difference in infectivity titers between virus stock and filtered stock was smaller than 1.0 log) were used.

Detergents

Prior to use the respective detergent, or a 1:10 dilution thereof (i.e. 1 g±2% of the respective detergent plus 9 g±2% of Aqua dest.), was stirred for at least 15 minutes to assure homogeneity.

Methods

The virus inactivation capacity and the robustness of the single-detergent treatment were evaluated under conditions unfavorable for virus inactivation, i.e. with short incubation times and at relatively low temperatures. As will be clear to a person skilled in the art, in commercial production processes such as biopharmaceutical production, longer incubation times and higher temperatures can be used, which will accelerate the kinetics of virus inactivation and may also increase the achieved LRV. Further, as already mentioned above, low concentrations of the respective detergents were used. As will be clear to a person skilled in the art, in commercial production processes such as biopharmaceutical production, higher concentrations of the respective detergents can be used, which will accelerate the kinetics of virus inactivation and may also increase the achieved LRV.

Since the protein concentration has no significant impact on virus inactivation (see also Dichtelmüller et al., 2009), the robustness concerning protein content was not investigated.

All following steps took place in a biosafety class II cabinet. The starting material was incubated under stirring at a temperature of +14° C.±1° C. using a double-walled vessel connected to a cryostat for incubation.

The buffer containing HSA was transferred to a screw-cap flask of which the tare weight had been determined. The weight of the buffer containing HSA (in the closed flask) was determined for calculation of the amount of the single detergent to be added. The needed amount of detergent ([mg]), or the respective amount of a 1:10 dilution thereof, was added per g of buffer containing HSA to yield the following final concentrations of the respective detergent: 0.1%±0.01% (w/w) or 0.03%±0.01% (w/w). The detergent was added under stirring within 1 minute using a syringe, and the actual amount added was determined by back-weighing the syringe. The buffer containing HSA was stirred further after completed detergent addition for at least 10 minutes. The buffer containing HSA mixed with the detergent was filtered through a 0.2 μm Supor syringe membrane filter (or equivalent) and the filtrate was collected at a targeted temperature of 14° C.±1° C. using a double-walled vessel connected to a cryostat. The vessel for the filtrate was cooled. In case of filter clogging, fresh filters were used for continuing filtration of the buffer containing HSA. After filtration, the temperature (target: 14° C.±1° C.) and the volume were measured.

The filtered buffer containing HSA with the respective detergent was adjusted under stirring to 14° C.±1° C. using a double-walled vessel connected to a cryostat. This temperature range was maintained under stirring until the end of the incubation of the buffer containing HSA with the detergent and was recorded continuously. The determined volume of the buffer containing HSA with detergent was spiked at a ratio of 1:31, e.g. 48 mL buffer containing HSA were spiked with 1.6 ml of virus stock solution. The spiked buffer containing HSA was further incubated under continued stirring at 14° C.±1° C. for 59±1 minutes. During incubation, samples for virus titration were taken at 1-2 min, 5±1 min, 29±1 min and 59±1 min. To prevent further inactivation of virus by the detergent following sample drawing, the samples were diluted immediately 1:20 with the respective cold (+2° C. to +8° C.) cell culture medium (i.e. 1 volume of sample plus 19 volumes of cell culture medium).

Spike- and Hold Controls were performed on the same day: Buffer containing HSA was filtered as described above, but without prior addition of detergent. Then the filtrate was adjusted to 14° C.±1° C. under stirring as described above. The buffer containing HSA was spiked at a ratio of 1:31 and further incubated at 14° C.±1° C. for 59±1 minutes as described above. Within 1-2 minutes after spiking, a sample for virus titration (Spike Control) was taken. After incubation for 59±1 minutes a sample for virus titration (i.e. the Hold Control sample) was taken (HC).

Titration of the samples and calculation of the virus clearance capacity was performed as described for Example 1 above.

Results

When single-detergent treatment of a buffer containing HSA was performed at 14° C.±1° C. using 0.1%±0.01% Triton X-100, Brij C10, 4-tert-octylbenzyl alcohol polyethoxylate or Triton X-100 reduced, BVDV was inactivated by a virus reduction factor (RF) of around 5 within 5 minutes (FIG. 12A). When single-detergent treatment of a buffer containing HSA was performed at 14° C.±1° C. using 0.03%±0.01% Triton X-100, 4-tert-octylbenzyl alcohol polyethoxylate or Triton X-100 reduced, BVDV was inactivated by a virus reduction factor (RF) of over 3 within 5 minutes, and of over 4 within 29 minutes (FIG. 12B).

These experiments indicate that single-detergent treatment of biopharmaceutical drug-containing liquids using Triton X-100, Brij C10, 4-tert-octylbenzyl alcohol polyethoxylate or Triton X-100 reduced results in efficient inactivation of lipid-enveloped viruses, even at low concentrations of the detergents.

Example 9: BVDV Inactivation Using 4-Tert-Octylbenzyl Alcohol Polyethoxylate or Triton X-100 Reduced in IVIG-Containing Liquid The suitability of 4-tert-octylbenzyl alcohol polyethoxylate or Triton X-100 reduced for single-detergent treatment to inactivate the lipid-enveloped virus bovine viral diarrhea virus (BVDV) in liquids comprising intravenous immunoglobulin (IVIG) was tested and compared to Triton X-100. To this end, virus was added to liquids comprising IVIG. The virus-containing liquids comprising IVIG were then incubated with low concentrations of Triton X-100 reduced, 4-tert-octylbenzyl alcohol polyethoxylate or Triton X-100 for various time periods, and the remaining infectivity of the viruses was determined. Triton X-100 reduced, 4-tert-octylbenzyl alcohol polyethoxylate and Triton X-100 were used at low concentrations in order to evaluate the kinetics of virus inactivation, i.e., the efficiency of virus inactivation (expressed by the RF) over time. As will be clear to a person skilled in the art, in commercial production processes such as biopharmaceutical production, the detergents of the invention including Triton X-100 reduced or 4-tert-octylbenzyl alcohol polyethoxylate can be used at significantly higher concentrations, which will accelerate the kinetics of virus inactivation and is also expected to increase the achieved LRV.

Materials
Liquid Comprising IVIG

A liquid comprising IVIG (IVIG-containing liquid) was frozen on dry ice and stored at ≤−60° C. until use within one year after the date of collection.

TABLE 13

Virus stock used in the experiments.

| Viruses | | | | | |
|---|---|---|---|---|---|
| | | Propagated on | | Titrated on | |
| Virus Strain | Source | Cell line | Source | Cell line | Source |
| BVDV | | | | | |
| Nadl | ATCC[1] VR-1422 | MDBK | ATCC[1] CRL-22 | BT | ATCC[1] CRL-1390 |

ATCC[1] American Type Culture Collection, 10801 University Boulevard, Manassas, VA 20110 USA Virus stocks were characterized prior to use. This characterization included the determination of the virus titer by at least ten independent titrations and specification of an acceptance virus titer range for use as positive control, the determination of virus stock protein content, PCR tests for virus identity and contamination with other viruses and *mycoplasma* and tests for virus aggregation with filters not allowing the passage of large virus aggregates. Only virus stocks passing PCR identity/contamination tests with no significant aggregation, (i.e. difference in infectivity titers between virus stock and filtered stock was smaller than 1.0 log) were used.

Detergents

Prior to use the respective detergent, or a 1:10 dilution thereof (i.e. 1 g±2% of the respective detergent plus 9 g±2% of Aqua dest.), was stirred for at least 15 minutes to assure homogeneity.

Methods

The virus inactivation capacity and the robustness of the single-detergent treatment were evaluated under conditions unfavorable for virus inactivation, i.e. with short incubation times and at relatively low temperatures. As will be clear to a person skilled in the art, in commercial production processes such as biopharmaceutical production, longer incubation times and higher temperatures can be used, which will accelerate the kinetics of virus inactivation and may also increase the achieved LRV. Further, as already mentioned above, low concentrations of the respective detergents were used. As will be clear to a person skilled in the art, in commercial production processes such as biopharmaceutical production, higher concentrations of the respective detergents can be used, which will accelerate the kinetics of virus inactivation and may also increase the achieved LRV.

Since the protein concentration has no significant impact on virus inactivation (see also Dichtelmüller et al., 2009), the robustness concerning protein content was not investigated.

The IVIG-containing liquid was thawed and all further steps took place in a biosafety class II cabinet. The IVIG-containing liquid was incubated under stirring at a temperature of +17° C.±1° C. using a double-walled vessel connected to a cryostat for incubation. The IVIG-containing liquid was then filtered through a 0.2 μm depth filter with an effective filter area of 25 cm$^2$ (Cuno VR06 or equivalent) connected to a Sartorius (SM16249) stainless steel filter holder using pressurized nitrogen at a targeted pressure of 0.9 bar (limit: 0.5 bar-1.5 bar). For conditioning the filter material was pre-coated with 55 L/m$^2$ of the Hyflo Supercel suspension (5.0 g±0.05 g of Hyflo Supercel per L; conductivity adjusted to 3.5 mS/cm (specified range: 2.5-6.0 mS/cm) using 3 M NaCl) (at a pressure of ≤0.5 bar) prior to filtration of the liquid. During filtration the filter holder was cooled and the filtrate was collected at a targeted temperature of +17° C.±1° C. using a double-walled vessel connected to a cryostat. The vessel for the filtrate was cooled. In case of filter clogging, fresh pre-conditioned filters were used for continuing filtration of the remaining liquid. After filtration the volume was measured.

After measuring the volume of the IVIG-containing liquid, it was adjusted under stirring with cold (+2° C. to +8° C.) dilution buffer (NaCl solution with target conductivity of 3.5 mS/cm (range: 2.5 mS/cm-6.0 mS/cm)) to a calculated target absorbance of 28.9 $AU_{280-320}$/cm (range: 14.5-72.3 $AU_{280-320}$/cm). Taking the later 1:31 virus spike into account, this resulted in a calculated target absorbance value of 28 $AU_{280-320}$/cm (range: 14-70 $AU_{280-320}$/cm) for incubation with the detergent after filtration.

The filtered and protein adjusted IVIG-containing liquid was again adjusted under stirring to +17° C.±1° C. using a double-walled vessel connected to a cryostat. This temperature range was maintained under stirring until the end of the incubation of the filtered IVIG-containing liquid with the detergent and was recorded continuously. The determined volume of the filtered IVIG-containing liquid, transferred to a screw-cap flask of which the tare weight had been determined, was spiked with virus at a ratio of 1:31, e.g. 30 mL of IVIG-containing liquid were spiked with 1 mL of virus stock solution. The spiked IVIG-containing liquid was further incubated under continued stirring at 17° C.±1° C. Within 1-2 minutes after spiking, samples for virus titration (Spike Control, SC, and Hold Control, HC) were taken.

After drawing, the Hold Control (HC) was kept at the same temperature, i.e. at +17° C.±1° C., as the spiked IVIG-containing liquid after addition of detergent, i.e. it was stored in the same cooling circle as the vessel with the IVIG-containing liquid, until the end of detergent treatment. The temperature of the cooling liquid was determined before insertion of the Hold Control sample and, again, shortly before the Hold Control was removed for titration after detergent treatment.

The weight of the spiked IVIG-containing liquid was determined for calculation of the amount of the detergent to be added. The weighed material was re-adjusted, if necessary, under stirring to +17° C.±1° C. The needed amount of detergent ([mg]), or the respective amount of a 1:10 dilution thereof, was added per g of IVIG-containing liquid to yield the following final concentrations of the respective detergent: 0.1%±0.01% (w/w) or 0.03%±0.01% (w/w). The detergent was added under stirring within 1 minute using a syringe, and the actual amount of detergent added was determined by back-weighing the syringe. The spiked IVIG-containing liquid was further incubated with the respective detergent under continued stirring at +17° C.±1° C. for 59±1 minutes. During incubation, 1 mL samples for virus titration were taken after 1-2 min, 10±1 min, 30±1 min and 59±1 min. To prevent further inactivation of virus by the S/D reagents following sample drawing, the samples were diluted immediately 1:20 with cold (+2° C. to +8° C.) cell culture medium (i.e. 1 volume of sample plus 19 volumes of cell culture medium).

Titration of the samples and calculation of the virus clearance capacity was performed as described for Example 1 above.

Results

When single-detergent treatment of IVIG-containing liquid was performed at 17° C.±1° C. using 0.1%±0.01% Triton X-100, 4-tert-octylbenzyl alcohol polyethoxylate or Triton X-100 reduced, BVDV was inactivated by a virus reduction factor (RF) of around 5 within 10 minutes (FIG. 13A). When single-detergent treatment of IVIG-containing liquid was performed at 17° C.±1° C. using 0.03%±0.01% Triton X-100, 4-tert-octylbenzyl alcohol polyethoxylate or Triton X-100 reduced, BVDV was inactivated by a virus reduction factor (RF) of over 3 within 10 minutes, and of over 4 within 30 minutes (FIG. 13B).

These experiments confirm that single-detergent treatment of biopharmaceutical drug-containing liquids using Triton X-100, 4-tert-octylbenzyl alcohol polyethoxylate or Triton X-100 reduced results in efficient inactivation of lipid-enveloped viruses, even at low concentrations of the detergents.

Example 10: BVDV Inactivation Using 4-Tert-Octylbenzyl Alcohol Polyethoxylate or Triton X-100 Reduced in FVIII-Containing Liquid The suitability of 4-tert-octylbenzyl alcohol polyethoxylate or Triton X-100 reduced for single-detergent treatment to inactivate the lipid-enveloped virus bovine viral diarrhea virus (BVDV) in liquids comprising plasma-derived Factor VIII (pdFVIII) was tested and compared to Triton X-100. To this end, virus was added to liquids comprising pdFVIII. The virus-containing liquids comprising pdFVIII were then incubated with low concentrations of Triton X-100 reduced, 4-tert-octylbenzyl alcohol polyethoxylate or Triton X-100 for various time periods, and the remaining infectivity of the viruses was determined. Triton X-100 reduced, 4-tert-octylbenzyl alcohol polyethoxylate and Triton X-100 were used at low concentrations in order to evaluate the kinetics of virus inactivation, i.e., the efficiency of virus inactivation (expressed by the RF) over time. As will be clear to a person skilled in the art, in commercial production processes such as biopharmaceutical production, the detergents of the invention including Triton X-100 reduced or 4-tert-octylbenzyl alcohol polyethoxylate can be used at significantly higher concentrations, which will accelerate the kinetics of virus inactivation and is also expected to increase the achieved LRV.

Materials

Liquid Comprising pdFVIII

A liquid comprising pdFVIII (pdFVIII-containing liquid) was frozen on dry ice and stored at ≤−60° C. until use within one year after the date of collection.

TABLE 14

Virus stock used in the experiments.

| | | Propagated on | | Titrated on | |
|---|---|---|---|---|---|
| Virus Strain | Source | Cell line | Source | Cell line | Source |
| BVDV | | | | | |
| NadI | ATCC[1] VR-1422 | MDBK | ATCC[1] CRL-22 | BT | ATCC[1] CRL-1390 |

ATCC[1] American Type Culture Collection, 10801 University Boulevard, Manassas, VA 20110 USA Virus stocks were characterized prior to use. This characterization included the determination of the virus titer by at least ten independent titrations and specification of an acceptance virus titer range for use as positive control, the determination of virus stock protein content, PCR tests for virus identity and contamination with other viruses and *mycoplasma* and tests for virus aggregation with filters not allowing the passage of large virus aggregates. Only virus stocks passing PCR identity/contamination tests with no significant aggregation, (i.e. difference in infectivity titers between virus stock and filtered stock was smaller than 1.0 log) were used.

Detergents

Prior to use the respective detergent, or a 1:10 dilution thereof (i.e. 1 g±2% of the respective detergent plus 9 g±2% of Aqua dest.), was stirred for at least 15 minutes to assure homogeneity.

Methods

The virus inactivation capacity and the robustness of the single-detergent treatment were evaluated under conditions unfavorable for virus inactivation, i.e. with short incubation times. As will be clear to a person skilled in the art, in commercial production processes such as biopharmaceutical production, longer incubation times can be used, which will accelerate the kinetics of virus inactivation and may also increase the achieved LRV. Further, as already mentioned above, low concentrations of the respective detergents were used. As will be clear to a person skilled in the art, in commercial production processes such as biopharmaceutical production, higher concentrations of the respective detergents can be used, which will accelerate the kinetics of virus inactivation and may also increase the achieved LRV.

Since the protein concentration has no significant impact on virus inactivation (see also Dichtelmüller et al., 2009), the robustness concerning protein content was not investigated.

The pdFVIII-containing liquid was thawed and all further steps took place in a biosafety class II cabinet. To remove possible gross aggregates the pdFVIII-containing liquid was filtered through a 0.45 µm membrane filter (e.g. Sartorius SartoScale Sartobran or equivalent). The pdFVIII-containing liquid was transferred to a screw-cap flask of which the tare weight had been determined and adjusted under stirring to a targeted temperature of +23° C.±1° C. using a double-walled vessel connected to a cryostat. The determined volume of the pdFVIII-containing liquid was spiked at a ratio of 1:31, e.g. 48 mL of the pdFVIII-containing liquid were spiked with 1.6 mL of virus stock solution. Subsequently, a sample each for virus titration (Spike Control, SC) and for the Hold Control (HC) were taken.

The Hold Control was kept at the same temperature, i.e. at +23° C.±1° C., as the spiked pdFVIII-containing liquid after addition of detergent, i.e. it was stored in the same cooling circle as the vessel with the pdFVIII-containing liquid, until the end of detergent treatment. The temperature of the cooling liquid was determined before insertion of the Hold Control sample and, again, shortly before the Hold Control was removed for titration after detergent treatment.

The weight of the spiked pdFVIII-containing liquid was determined for calculation of the amount of detergent to be added. The weighed material was adjusted under stirring to +23° C.±1° C. using a double-walled vessel connected to a cryostat. This temperature range was maintained under stirring until the end of the incubation of the spiked pdFVIII-containing liquid with the detergent and was recorded continuously. The needed amount of detergent ([mg]), or the respective amount of a 1:10 dilution thereof, was added per g of pdFVIII-containing liquid to yield a final detergent concentration of 0.1%±0.01% (w/w). The detergent was added under stirring within 1 minute using a syringe, and the actual amount of detergent added was determined by back-weighing the syringe. After the addition of the detergent had been completed, the spiked pdFVIII-containing liquid was further incubated under continued stirring at +23° C.±1° C. for 59±1 minutes. During incubation, 1 mL samples for virus titration were taken after 1-2 min, 5±1 min, 30±1 min and 59±1 min. To prevent further inactivation of virus by the detergent following sample drawing, the samples were diluted immediately 1:20 with the respective cold (+2 to +8° C.) cell culture medium (i.e. 1 volume of sample plus 19 volumes of cell culture medium).

Titration of the samples and calculation of the virus clearance capacity was performed as described for Example 1 above.

Results

When single-detergent treatment of pdFVIII-containing liquid was performed at 23° C.±1° C. using 0.1%±0.01% Triton X-100, 4-tert-octylbenzyl alcohol polyethoxylate or Triton X-100 reduced, BVDV was inactivated by a virus reduction factor (RF) of around 5 within 5 minutes (FIG. 14).

These experiments confirm that single-detergent treatment of biopharmaceutical drug-containing liquids using Triton X-100, 4-tert-octylbenzyl alcohol polyethoxylate or Triton X-100 reduced results in efficient inactivation of lipid-enveloped viruses, even at low concentrations of the detergents.

Example 11: Toxicology Tests

Based on in silico data, for none of the detergents according to the invention any evidence has been found to be active as endocrine disruptors.

INDUSTRIAL APPLICABILITY

The methods, processes and products of the invention are commercially useful, e.g. for environmentally compatible inactivation of lipid-enveloped viruses in industrial manufacturing processes. For example, the invention can be used in the industrial production of biopharmaceuticals. Thus, the invention is industrially applicable.

REFERENCES

Dichtelmüller et al. (2009): Robustness of solvent/detergent treatment of plasma derivatives: a data collection from Plasma Protein Therapeutics Association member companies. Transfusion 49(9): 1931-1943.

Di Serio et al. (2005): Comparison of Different Reactor Types Used in the Manufacture of Ethoxylated, Propoxylated Products. Ind. Eng. Chem. Res. 44(25): 9482-9489.

ECHA Support document for identification of 4-(1,1,3,3-tetramethylbutyl)phenol, ethoxylated as substances of very high concern because, due to their degradation to a substance of very high concern (4-(1,1,3,3-tetramethylbutyl)phenol) with endocrine disrupting properties, they cause probable serious effects to the environment which give rise to an equivalent level of concern to those of CMRs and PBTs/vPvBs, adopted on 12 Dec. 2012

Brochure "Global Assessment of the Sate-of-the-Science of Endocrine Disruptors" (WHO/PCS/EDC/02.2), published by the International Programme on Chemical Safety of the World Health Organisation Simons et al. (1973): Solubilization of the membrane proteins from Semliki Forest virus with Triton X100. J Mol Biol. 80(1):119-133.

U.S. Pat. No. 1,970,578

Vogel's Textbook of Practical Organic Chemistry ((5th Edition, 1989, A. I. Vogel, A. R. Tatchell, B. S. Furnis, A. J. Hannaford, P. W. G. Smith)

Bioorganic & Medicinal Chemistry, 16(9), 4883-4907; 2008: Effects of modifications of the linker in a series of phenylpropanoic acid derivatives: Synthesis, evaluation as PPARα/γ dual agonists, and X-ray crystallographic studies; Casimiro-Garcia, Agustin; Bigge, Christopher F.; Davis, Jo Ann; Padalino, Teresa; Pulaski, James; Ohren, Jeffrey F.; McConnell, Patrick; Kane, Christopher D.; Royer, Lori J.; Stevens, Kimberly A.; Auerbach, Bruce J.; Collard, Wendy T.; McGregor, Christine; Fakhoury, Stephen A.; Schaum, Robert P.; Zhou, Hairong. DOI: 10.1016/j.bmc.2008.03.

Chemistry—A European Journal, 23(60), 15133-15142; 2017: Solid Phase Stepwise Synthesis of Polyethylene Glycols; Khanal, Ashok; Fang, Shiyue.DOI:10.1002/chem.201703004

Journal of Medicinal Chemistry, 48(10), 3586-3604; 2005: Synthesis and Structure-Activity Relationships of Novel Selective Factor Xa Inhibitors with a Tetrahydroisoquinoline Ring; Ueno, Hiroshi; Yokota, Katsuyuki; Hoshi, Jun-Ichi; Yasue, Katsutaka; Hayashi, Mikio; Hase, Yasunori; Uchida, Itsuo; Aisaka, Kazuo; Katoh, Susumu; Cho, Hidetsura. DOI:10.1021/jm058160e Journal of Nanoparticle Research, 15(11), 2025/1-2025/12, 12 pp.; 2013: Magnetic nanoparticles conjugated to chiral imidazolidinone as recoverable catalyst; Mondini, Sara; Puglisi, Alessandra; Benaglia, Maurizio; Ramella, Daniela; Drago, Carmelo; Ferretti, Anna M.; Ponti, Alessandro. DOI:10.1007/s11051-013-2025-3

Journal of Organic Chemistry, 79(1), 223-229; 2014: A Scalable Procedure for Light-Induced Benzylic Brominations in Continuous Flow; Cantillo, David; de Frutos, Oscar; Rincon, Juan A.; Mateos, Carlos; Kappe, C. Oliver. DOI:10.1021/jo402409k Journal of Physical Chemistry B, 107(31), 7896-7902; 2003: Anellated hemicyanine dyes with large symmetrical solvatochromism of absorption and fluorescence; Huebener, Gerd; Lambacher, Armin; Fromherz, Peter. DOI:10.1021/jp0345809

PCT Int. Appl., 2005016240, 24 Feb. 2005: Preparation of aryl carbamate oligomers for hydrolyzable prodrugs and prodrugs comprising same; Ekwuribe, Nnochiri N.; Odenbaugh, Amy L. WO 2004-US15004, May 6, 2004

Russian Journal of Applied Chemistry, 82(6), 1029-1032; 2009: Relative activity of alkenyl-gem-dichlorocyclopropanes in the reactions of hydrogenation and alkylation; Brusentsova, E. A.; Zlotskii, S. S.; Kutepov, B. I.; Khazipova, A. N. DOI:10.1134/S1070427209060196

Russian Journal of Organic Chemistry, 51(11), 1545-1550; 2015: Alkylation of aromatic compounds with 1-bromoadamantane in the presence of metal complex catalysts; Khusnutdinov, R. I.; Shchadneva, N. A.; Khisamova, L. F.

The invention claimed is:

1. A compound which is the following compound:

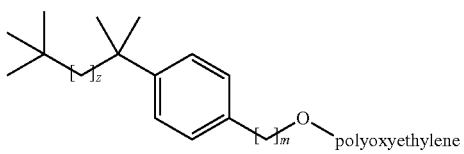

wherein m equals 1 and z is an integer selected from the following group:
z=1 to 5.

2. The compound of claim 1, wherein the compound is:

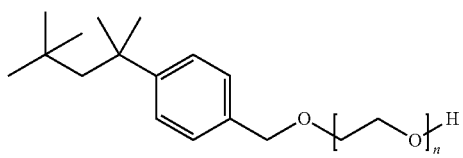

wherein n is an integer between 4 and 16.

3. A method for inactivating a virus having a lipid envelope, the method comprising the following steps:
   a) adding a detergent to a liquid to prepare a mixture of said detergent and said liquid; and
   b) incubating said mixture to inactivate said virus,
   wherein said detergent is a polyoxyethylene ether, wherein said detergent is a non-phenolic detergent, and wherein the detergent is the compound of claim 1.

4. The method of claim 3, wherein said detergent is environmentally compatible.

5. The method of claim 3, wherein step a) further comprises adding a solvent to said liquid, and wherein in step a), a solvent/detergent mixture for inactivation of said virus is prepared by adding said detergent and said solvent to said liquid.

6. The method of claim 5, wherein said solvent is an organic solvent.

7. The method of claim 3, wherein said liquid comprises a biological medicinal product and/or a biopharmaceutical drug.

8. The method of claim 7, wherein said biopharmaceutical drug is a therapeutic protein.

9. The method of claim 3, wherein:
   (a) prior to step a) or between step a) and step b), said method further comprises a step of filtering said liquid or mixture with a depth filter;
   (b) in step b), said mixture is incubated for at least 1 hour; and/or
   (c) in step b), said mixture is incubated at a temperature of between 0° C. and 10° C., or
   wherein said mixture is incubated at a temperature of between 16° C. and 25° C.

10. The method of claim 7, further comprising, after step b), a step of
   c) purifying said biopharmaceutical drug; and wherein:
   (i) said purifying comprises separating said biopharmaceutical drug from said detergent; and/or
   (ii) said purifying of said biopharmaceutical drug comprises purifying said biopharmaceutical drug by at least one chromatographic purification.

11. A method for preparing a biopharmaceutical drug, said method comprising the method according to claim 7, wherein said biopharmaceutical drug is as defined in claim 7.

12. The method of claim 11, further comprising a step of preparing a pharmaceutical formulation comprising said biopharmaceutical drug.

13. A composition comprising a detergent, wherein the detergent is the compound of claim 1.

14. The composition of claim 13 further comprising an organic solvent.

15. A method for synthesizing a compound of the following general Formula (VIII),

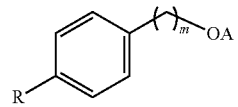

Formula (VIII)

wherein
R represents a hydrocarbon group having a linear chain of 2 to 12 carbon atoms and one or more methyl groups as substituents on said linear chain,
m equals 1, and
A represents a polyoxyethylene residue,
wherein the method comprises the steps of
   A) Converting a phenol of the following general Formula (IX) wherein R is as defined above

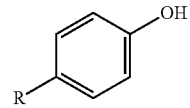

Formula (IX)

into an alcohol of the of the following general Formula (X) wherein R and m are as defined above

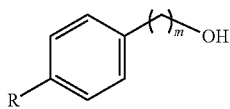

Formula (X)

and (B) converting the alcohol of the general Formula (X) into a polyoxyethylene ether of the general Formula (VIII) as defined above;

wherein the compound of Formula (VIII) is the following compound:

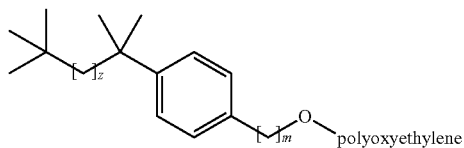

wherein m equals 1 and z is an integer selected from the following group:

z=1 to 5.

16. A method for synthesizing a compound of the following general Formula (VIII),

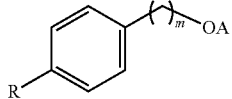

Formula (VIII)

Wherein

R represents a hydrocarbon group having a linear chain of 2 to 12 carbon atoms and one or more methyl groups as substituents on said linear chain, m equals 1, and A represents a polyoxyethylene residue, wherein the method comprises the steps of (1) reacting toluene so as to obtain a substituted toluene of the following general Formula (XI) wherein R is as defined above

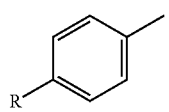

Formula (XI)

(2) converting the substituted toluene of the general Formula (XI) into a compound of the following general Formula (XII), wherein R and m are as defined above and X is selected from the group comprising a hydroxyl group, a bromine atom, an iodine atom and a chlorine atom

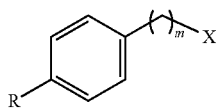

Formula (XII)

and (3) converting the compound of the general Formula (XII) into a polyoxyethylene ether of the general Formula (VIII) as defined above;

wherein the compound of Formula (VIII) is the following compound:

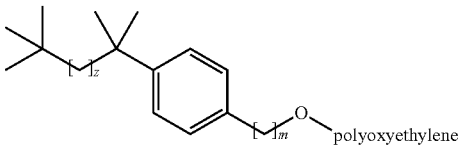

wherein m equals 1 and z is an integer selected from the following group:

z=1 to 5.

17. A method for synthesizing a compound of the following general Formula (VIIIa),

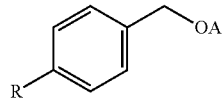

Formula (VIIIa)

wherein

R represents a hydrocarbon group having a linear chain of 2 to 12 carbon atoms and one or more methyl groups as substituents on said linear chain, and A represents a polyoxyethylene residue, wherein the method comprises the steps of (I) converting benzyl alcohol into a compound of the following general Formula (XIII), wherein R is as defined above

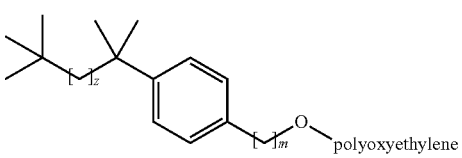

Formula (XIII)

and (II) converting the compound of the general Formula (XIII) into a polyoxyethylene ether of the general Formula (VIIIa) as defined above;

wherein the compound of Formula (VIIIa) is the following compound:

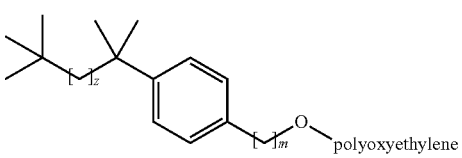

wherein m equals 1 and z is an integer selected from the following group:

z=1 to 5.

18. The method of claim 15, wherein the compound of Formula (VIII) is the following compound:

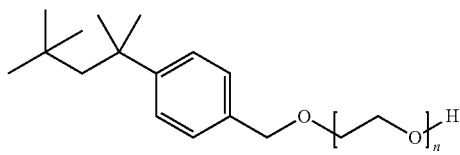

wherein n is an integer between 4 and 16.

19. The method of claim 16, wherein:
(i) the converting in step (2) is a radical reaction using AIBN (Azobis(isobutyronitrile)) as a radical initiator; and/or
(ii) X is a bromine atom.

20. The method of claim 16, wherein:
(a) the converting in step (2) uses N-bromosuccinimide (NBS) as a reagent;
(b) the converting in step (3) uses TBME (methyl-tert-butylether) as a solvent;
(c) the converting in step (3) takes place for at least 2 hours;
(d) the converting in step (3) takes place for not more than 5 hours; and/or
(e) the converting in step (3) takes place for 3 hours.

21. The compound of claim 2, wherein n is equal to 9 or 10.

22. The method of claim 6, wherein said solvent is Tri-n-butyl phosphate.

23. The method of claim 8, wherein said therapeutic protein is a blood factor, an immunoglobulin, a replacement enzyme, a vaccine, a gene therapy vector, a growth factor, or a growth factor receptor.

24. The method of claim 23, wherein said immunoglobulin is a monoclonal antibody.

25. The method of claim 23, wherein said blood factor is selected from the group consisting of factor I (fibrinogen), factor II (prothrom-bin), Tissue factor, factor V, factor VII or VIIa, factor VIII, factor IX, factor X, factor XI, factor XII, factor XIII, von Willebrand Factor (VWF), prekallikrein, high-molecular-weight kininogen (HMWK), fibronectin, antithrombin III, heparin cofactor II, protein C, protein S, protein Z, plasminogen, alpha 2-antiplasmin, tissue plasminogen activator (tPA), urokinase, plasminogen activator inhibitor-1 (PAI1), and plasminogen activator inhibitor-2 (PAI2).

26. The method of claim 25, wherein the factor VIII is recombinant human factor VIII.

27. The method of claim 10, wherein said at least one chromatographic purification is by anion exchange chromatography and/or by cation exchange chromatography.

28. The composition of claim 14, wherein said solvent is Tri-n-butyl phosphate.

29. The method of claim 18, wherein n is equal to 9 or 10.

30. The method of claim 20, wherein the converting in step (3) takes place for at least 2 hours at ambient temperature.

31. The method of claim 20, wherein the converting in step (3) takes place for not more than 5 hours at ambient temperature.

32. The method of claim 20, wherein the converting in step (3) takes place for 3 hours at ambient temperature.

* * * * *